US011584916B2

(12) United States Patent
Wells et al.

(10) Patent No.: US 11,584,916 B2
(45) Date of Patent: Feb. 21, 2023

(54) METHOD OF MAKING IN VIVO HUMAN SMALL INTESTINE ORGANOIDS FROM PLURIPOTENT STEM CELLS

(71) Applicant: Children's Hospital Medical Center, Cincinnati, OH (US)

(72) Inventors: James M. Wells, Cincinnati, OH (US); Carey Lane Watson, Cincinnati, OH (US); Jorge Orlando Munera, Cincinnati, OH (US); Maxime Mickael Mahe, Cincinnati, OH (US); Michael A. Helmrath, Cincinnati, OH (US); Michael J. Workman, Santa Monica, CA (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/515,840

(22) PCT Filed: Oct. 16, 2015

(86) PCT No.: PCT/US2015/055956
§ 371 (c)(1),
(2) Date: Mar. 30, 2017

(87) PCT Pub. No.: WO2016/061464
PCT Pub. Date: Apr. 21, 2016

(65) Prior Publication Data
US 2017/0292116 A1 Oct. 12, 2017

Related U.S. Application Data

(60) Provisional application No. 62/065,131, filed on Oct. 17, 2014.

(51) Int. Cl.
| | |
|---|---|
| *C12N 5/00* | (2006.01) |
| *C12N 5/071* | (2010.01) |
| *G01N 33/50* | (2006.01) |
| *A01K 67/027* | (2006.01) |

(52) U.S. Cl.
CPC ........ *C12N 5/0679* (2013.01); *A01K 67/0271* (2013.01); *C12N 5/0697* (2013.01); *G01N 33/5073* (2013.01); *A01K 2227/105* (2013.01); *A01K 2227/30* (2013.01); *A01K 2267/03* (2013.01); *C12N 2501/10* (2013.01); *C12N 2501/11* (2013.01); *C12N 2501/119* (2013.01); *C12N 2501/155* (2013.01); *C12N 2501/16* (2013.01); *C12N 2501/345* (2013.01); *C12N 2501/385* (2013.01); *C12N 2501/415* (2013.01); *C12N 2501/727* (2013.01); *C12N 2502/08* (2013.01); *C12N 2502/23* (2013.01); *C12N 2503/00* (2013.01); *C12N 2506/02* (2013.01); *C12N 2506/45* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 5,912,227 | A | 6/1999 | Croom, Jr. et al. |
| 5,942,435 | A | 8/1999 | Wheeler |
| 6,607,501 | B2 | 8/2003 | Gorsuch |
| 7,160,719 | B2 | 1/2007 | Nyberg |
| 7,291,626 | B1 | 11/2007 | Beachy et al. |
| 7,326,572 | B2 | 2/2008 | Fisk et al. |
| 7,510,876 | B2 | 3/2009 | D'Amour et al. |
| 7,514,185 | B2 | 4/2009 | Fukushima et al. |
| 7,541,185 | B2 | 6/2009 | D'Amour et al. |
| 7,625,753 | B2 | 12/2009 | Kelly et al. |
| 7,695,958 | B2 | 4/2010 | Funatsu et al. |
| 7,704,738 | B2 | 4/2010 | D'Amour et al. |
| 7,727,998 | B2 | 6/2010 | Moriya et al. |
| 7,776,592 | B2 | 8/2010 | Wandinger-Ness et al. |
| 7,927,869 | B2 | 4/2011 | Rosero |
| 7,985,585 | B2 | 7/2011 | D'Amour et al. |
| 7,993,916 | B2 | 8/2011 | Agulnick et al. |
| 8,187,878 | B2 | 5/2012 | Dalton et al. |
| 8,216,826 | B2 | 7/2012 | Lee et al. |
| 8,216,836 | B2 | 7/2012 | D'Amour et al. |
| 8,298,822 | B2 | 10/2012 | Kruse et al. |
| 8,318,492 | B2 | 11/2012 | Choo et al. |

(Continued)

FOREIGN PATENT DOCUMENTS

| | | |
|---|---|---|
| CN | 103154237 A | 6/2013 |
| CN | 103561751 A | 2/2014 |
| CN | 105985395 A | 10/2016 |
| EP | 2393917 A2 | 12/2011 |
| EP | 2393917 B1 | 4/2016 |
| EP | 3228306 A1 | 10/2017 |
| JP | 2003-521673 A | 7/2003 |
| JP | 2008-503203 A | 2/2008 |
| JP | 2008-505638 A | 2/2008 |

(Continued)

OTHER PUBLICATIONS

Merker etal (Developmental Biology, 420: 239-250, 2016) (Year: 2016).*
Lee etal, (Nature Biotechnology, 25(12): 1468-1475, 2007); (Year: 2007).*
Barlow etal, (Development, 135: 1681-1691, 2008); (Year: 2008).*
Avansino etal, (Surgery, 140:423-34, 2006). (Year: 2006).*

(Continued)

*Primary Examiner* — Anoop K Singh
*Assistant Examiner* — Magdalene K Sgagias
(74) *Attorney, Agent, or Firm* — Knobbe Martens Olson & Bear LLP

(57) ABSTRACT

Disclosed are methods for making a vascularized hollow organ derived from human intestinal organoid (HIOs). The HIOs may be obtained from human embryonic stem cells (ESC's) and/or induced pluripotent stem cells (iPSCs), such that the HIO forms mature intestinal tissue. Also disclosed are methods for making a human intestinal tissue containing a functional enteric nervous system (ENS).

9 Claims, 25 Drawing Sheets

Specification includes a Sequence Listing.

(56) References Cited

U.S. PATENT DOCUMENTS

| | | |
|---|---|---|
| 8,501,476 B2 | 8/2013 | Morgan et al. |
| 8,586,357 B2 | 11/2013 | D'Amour et al. |
| 8,603,809 B2 | 12/2013 | Kruse |
| 8,609,406 B2 | 12/2013 | Subramanian et al. |
| 8,609,413 B2 | 12/2013 | Suter et al. |
| 8,623,645 B2 | 1/2014 | D'Amour et al. |
| 8,632,645 B2 | 1/2014 | Daitou et al. |
| 8,633,024 B2 | 1/2014 | D'Amour et al. |
| 8,642,339 B2 | 2/2014 | Sato et al. |
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rajagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,000,740 B2 | 6/2018 | Vallier et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 10,668,108 B2 | 6/2020 | Takebe et al. |
| 10,781,425 B2 | 9/2020 | Wells et al. |
| 11,053,477 B2 | 7/2021 | Wells et al. |
| 11,066,650 B2 | 7/2021 | Wells et al. |
| 2003/0129751 A1 | 7/2003 | Grikscheit et al. |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0151564 A1 | 6/2011 | Menu et al. |
| 2011/0218512 A1 | 9/2011 | Tullis et al. |
| 2011/0294735 A1 | 12/2011 | Marsh et al. |
| 2012/0009086 A1 | 1/2012 | Nyberg et al. |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1* | 8/2012 | Mezghanni ........ G01N 33/5005 435/5 |
| 2012/0196312 A1 | 8/2012 | Sato et al. |
| 2012/0264209 A1 | 10/2012 | Odorico et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2014/0038279 A1 | 2/2014 | Ingber et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0336282 A1 | 11/2014 | Ewald et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0273071 A1 | 10/2015 | Green et al. |
| 2015/0273127 A1 | 10/2015 | Flieg et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |

(56) References Cited

U.S. PATENT DOCUMENTS

| | | |
|---|---|---|
| 2016/0184387 A1 | 6/2016 | Charmot et al. |
| 2016/0186140 A1 | 6/2016 | Dalton et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0244724 A1 | 8/2016 | Ferro |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0202885 A1 | 7/2017 | Agulnick |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0043357 A1 | 2/2018 | Bocchi et al. |
| 2018/0059119 A1 | 3/2018 | Takats et al. |
| 2018/0112187 A1 | 4/2018 | Smith et al. |
| 2018/0250410 A1 | 9/2018 | Borros Gomez et al. |
| 2018/0258400 A1 | 9/2018 | Ng et al. |
| 2019/0031992 A1 | 1/2019 | Kerns et al. |
| 2019/0078055 A1 | 3/2019 | Wells et al. |
| 2019/0093076 A1 | 3/2019 | Schulz |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |
| 2020/0040309 A1 | 2/2020 | Takebe et al. |
| 2020/0056157 A1 | 2/2020 | Takebe et al. |
| 2020/0190478 A1 | 6/2020 | Wells et al. |
| 2020/0199537 A1 | 6/2020 | Takebe et al. |
| 2021/0008123 A1 | 1/2021 | Takebe et al. |
| 2021/0096126 A1 | 4/2021 | Takebe et al. |
| 2021/0115366 A1 | 4/2021 | Mahe et al. |
| 2021/0180026 A1 | 6/2021 | Takebe et al. |
| 2021/0189349 A1 | 6/2021 | Wells et al. |
| 2021/0292714 A1 | 9/2021 | Takebe et al. |
| 2021/0324334 A1 | 10/2021 | Takebe et al. |
| 2022/0056420 A1 | 2/2022 | Wells et al. |
| 2022/0090011 A1 | 3/2022 | Ngan et al. |

FOREIGN PATENT DOCUMENTS

| | | | |
|---|---|---|---|
| JP | 2013-066414 A | 4/2013 | |
| KR | 10-2006-0114355 A | 11/2006 | |
| WO | WO 92/07615 | 5/1992 | |
| WO | WO 98/21312 | 5/1998 | |
| WO | WO 2003/082201 A2 | 10/2003 | |
| WO | WO 2005/001072 A1 | 1/2005 | |
| WO | WO 2005/081970 A2 | 9/2005 | |
| WO | WO 2005/097974 A2 | 10/2005 | |
| WO | WO 2005/113747 A2 | 12/2005 | |
| WO | WO 2006/126236 A1 | 11/2006 | |
| WO | WO 2008/075339 A2 | 6/2008 | |
| WO | WO 2009/022907 A2 | 2/2009 | |
| WO | WO-2009086596 A1 | 7/2009 | |
| WO | WO 2009/146911 A2 | 12/2009 | |
| WO | WO 2010/008905 A2 | 1/2010 | |
| WO | WO 2010/090513 A2 | 8/2010 | |
| WO | WO 2010/094694 A1 | 8/2010 | |
| WO | WO 2010/127399 A1 | 11/2010 | |
| WO | WO 2010/143747 A1 | 12/2010 | |
| WO | WO-2011116930 A1 | 9/2011 | |
| WO | WO 2011/139628 A1 | 11/2011 | |
| WO | WO 2011/140441 A2 | 11/2011 | |
| WO | WO-2011140441 A2 * | 11/2011 | ........... C12N 5/0661 |
| WO | WO 2012/014076 A2 | 2/2012 | |
| WO | WO 2012/027474 A1 | 3/2012 | |
| WO | WO 2012/089669 A1 | 7/2012 | |
| WO | WO 2012/118799 A2 | 9/2012 | |
| WO | WO 2012/154834 A1 | 11/2012 | |
| WO | WO 2012/155110 A1 | 11/2012 | |
| WO | WO 2012/166903 A1 | 12/2012 | |
| WO | WO 2012/168930 A2 | 12/2012 | |
| WO | WO 2012/178215 A1 | 12/2012 | |
| WO | WO 2013/040087 A2 | 3/2013 | |
| WO | WO 2013/067498 A1 | 5/2013 | |
| WO | WO 2013/086486 A1 | 6/2013 | |
| WO | WO 2013/086502 A1 | 6/2013 | |
| WO | WO 2013/093812 A2 | 6/2013 | |
| WO | WO 2013096741 A2 | 6/2013 | |
| WO | WO 2013/127921 A1 | 9/2013 | |
| WO | WO 2013/155060 A1 | 10/2013 | |
| WO | WO 2013/174794 A1 | 11/2013 | |
| WO | WO 2013/192290 A1 | 12/2013 | |
| WO | WO 2014/013334 A2 | 1/2014 | |
| WO | WO-2014018691 A1 | 1/2014 | |
| WO | WO 2014/048637 A1 | 4/2014 | |
| WO | WO 2014/053596 A1 | 4/2014 | |
| WO | WO 2014/082096 A1 | 5/2014 | |
| WO | WO 2014/090993 A1 | 6/2014 | |
| WO | WO 2014/127170 A1 | 8/2014 | |
| WO | WO 2014/151921 A1 | 9/2014 | |
| WO | WO 2014/153230 A1 | 9/2014 | |
| WO | WO 2014/153294 A1 | 9/2014 | |
| WO | WO 2014/159356 | 10/2014 | |
| WO | WO 2014/173907 A1 | 10/2014 | |
| WO | WO 2014/182885 A2 | 11/2014 | |

(56) References Cited

FOREIGN PATENT DOCUMENTS

| | | |
|---|---|---|
| WO | WO 2014/197934 A1 | 12/2014 |
| WO | WO 2014/199622 A1 | 12/2014 |
| WO | WO 2015/021358 A2 | 2/2015 |
| WO | WO 2015/060790 A1 | 4/2015 |
| WO | WO 2015/075175 A1 | 5/2015 |
| WO | WO 2015/076388 A1 | 5/2015 |
| WO | WO 2015/108893 A1 | 7/2015 |
| WO | WO 2015/123183 A1 | 8/2015 |
| WO | WO 2015/129822 A1 | 9/2015 |
| WO | WO 2015/130919 A1 | 9/2015 |
| WO | WO 2015/135893 A1 | 9/2015 |
| WO | WO 2015/138032 A2 | 9/2015 |
| WO | WO 2015/152954 A1 | 10/2015 |
| WO | WO 2015/156929 A1 | 10/2015 |
| WO | WO 2015/157163 A1 | 10/2015 |
| WO | WO 2015/168022 A1 | 11/2015 |
| WO | WO 2015/0173425 A1 | 11/2015 |
| WO | WO 2015/183920 A2 | 12/2015 |
| WO | WO 2015/184273 A1 | 12/2015 |
| WO | WO 2015/184375 A2 | 12/2015 |
| WO | WO 2015/185714 A1 | 12/2015 |
| WO | WO 2015/196012 A1 | 12/2015 |
| WO | WO 2015/200901 A1 | 12/2015 |
| WO | WO 2016/011377 | 1/2016 |
| WO | WO 2016/015158 A1 | 2/2016 |
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO-2016056999 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/121512 A1 | 8/2016 |
| WO | WO 2016/140716 A1 | 9/2016 |
| WO | WO 2016/141137 A1 | 9/2016 |
| WO | WO 2016/144769 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 | 12/2016 |
| WO | WO 2017/009263 A1 | 1/2017 |
| WO | WO 2017/036533 | 3/2017 |
| WO | WO 2017/037295 A1 | 3/2017 |
| WO | WO 2017/041041 A1 | 3/2017 |
| WO | WO 2017/048193 A1 | 3/2017 |
| WO | WO 2017/048322 | 3/2017 |
| WO | WO 2017049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO-2017070337 A1 | 4/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO 2017/096192 A1 | 6/2017 |
| WO | WO 2017/096282 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 | 10/2017 |
| WO | WO 2017/174609 A1 | 10/2017 |
| WO | WO 2017/176810 A1 | 10/2017 |
| WO | WO 2017/184586 | 10/2017 |
| WO | WO-2017175876 A1 | 10/2017 |
| WO | WO 2017/192997 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/094522 A1 | 5/2018 |
| WO | WO-2018085622 A1 | 5/2018 |
| WO | WO-2018085623 A1 | 5/2018 |
| WO | WO 2018/106628 A1 | 6/2018 |
| WO | WO-2018115852 A1 | 6/2018 |
| WO | WO-2018191673 A1 | 10/2018 |
| WO | WO 2018/197544 A1 | 11/2018 |
| WO | WO-2018200481 A1 | 11/2018 |
| WO | WO-2018226267 A1 | 12/2018 |
| WO | WO 2019/074793 A1 | 4/2019 |
| WO | WO-2019126626 A1 | 6/2019 |
| WO | WO-2020023245 A1 | 1/2020 |
| WO | WO-2020056158 A1 | 3/2020 |
| WO | WO-2020069285 A1 | 4/2020 |

OTHER PUBLICATIONS

Lindley etal, (Gastroenterology, 135: 205-216, 2008). (Year: 2008).*
Burns etal (Development, 129: 2785-96, 2002). (Year: 2002).*
Mosheretal, (Dev Biol, 303(1): 1-15, 2007); (Year: 2007).*
Fu et al, (Developmental Dynamics, 228: 1-10, 2003). (Year: 2003).*
Kawaguchi et al (Development 137: 693-704, 2010). (Year: 2010).*
Huang (Biochemical and Biophysical Research Communications 351 (2006) 321-327) (Year: 2006).*
Okada (Developmental Biology 275 (2004) 124-142) (Year: 2004).*
Brevini et al., 2010, Theriogenology, vol. 74, pp. 544-550 (Year: 2010).*
Simkin (PLoS ONE 8(5): e64077 pp. 1-12, 2013); (Year: 2013).*
Bain (Developmental Biology, 168: 842-357 (1995 (Year: 1995).*
Goldstein, (Mechanisms of Development, 122: 821-833, 2005 (Year: 2005).*
Lui (Gastroenterology, 134: 1104-1115, 2008), (Year: 2008).*
Burns (The Anatomical Record, 262: 16-28, 2001). (Year: 2001).*
McCamm (Neurogastroenterol Motil, 30: e13369, p. 1-9, 2018) (Year: 2018).*
Alessi, D.R., et al., "LKB1-Dependent Signaling Pathways," Annu. Rev. Biochem., 2006, 75:137-63, 30 pgs.
Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.

(56) References Cited

OTHER PUBLICATIONS

Amieva, M.R., et al. "*Helicobacter pylori* enter and survive within multivesicular vacuoles of epithelial cells," Cell. Microbiol., 2002, 4(10):677-690, 15 pgs.

Andrews, P.W., et al., "Embryonic stem (ES) cells and embryonal carcinoma (EC) cells: opposite sides of the same coin," Biochem Soc Trans, 2005, 33(part 6):1526-1530, 5 pgs.

Ang, S-L, et al., "The formation and maintenance of the definitive endoderm lineage in the mouse: involvement of HMF3/*forkhead* proteins," Development, 1993, 119:1301-1315, 15 pgs.

Bansal, D., et al., "An ex-vivo human intestinal model to study *Entamoeba histolytica* Pathogenesis," PLoS Neglected Tropical Diseases, Nov. 2009, 3(11):e551.

Barker, N., et al., "Lgr5$^{+ve}$Stem Cells Drive Self-Renewal in the Stomach and Build Long-Lived Gastric Units In Vitro," Cell Stem Cell, 2010, 6:25-36, 12 pgs.

Bastide, P., et al. "Sox9 regulates cell proliferation and is required for Paneth cell differentiation in the intestinal epithelium," JCB, 2007, 178(4), pp. 635-648, 14 pages.

Beck, F., et al., "Expression of *Cdx-2* in the mouse embryo and placenta: possible tole in patterning of the extra-embroyonic membranes," Dev Dyn, 1995, 204:219-227.

Brevini, T.A.L., et al., "No shortcuts to pig embryonic stem cells," Theriogenology, 2010, 74:544-550, 7 pgs.

Chen, C., et al., "*Pdx1* inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.

Churin, Y., et al., "*Helicobacter pylori* CagA protein targets the c-Met receptor and enhances the motogenic response," J. Cell Biol., 2003, 161:249-255, 7 pgs.

Coghlan, M.P., et al., "Selective small molecule inhibitors of glycogen synthase kinase-3 modulate glycogen metabolism and gene transcription," Chem. Biol., 2000, 7(10):793-803, 11 pgs.

Couzin. J., "Small RNAs Make Big Splash." Science. 2002, 298:2296-2297, 2 pgs.

Covacci. A., et al., "Molecular characterization of the 128-kDa immunodominant antigen of *Helicobacter pylori* associated with cytotoxicity and duodenal ulcer," Proc Natl Acad SciUSA, Jun. 1993, 90:5791-5795, 5 pgs.

D'Amour, K.A., et al., "Production of pancreatic hormone-expressing endocrine cells from human embiyonic stem cells," Nat Biotechnol, 2006, 24:1392-1401, 10 pgs.

De Santa Barbara, P., et al., "Development and differentiation of the intestinal epithelium," Cell Mol Life Sci, 2003, 60(7):1322-1332, 12 pgs.

Dessimoz, J., et al., "FGF signaling is necessary for establishing gut tube domains along the anterior-posterior axis in vivo," Mech Dev, 2006, 123:42-55, 14 pgs.

Elbashir, S.M., et al., "Functional anatomy of siRNAs for mediating efficient RNAi in *Drosophila melanogaster* embryo lysate," EMBO J., 2001, 20(23):6877-6888, 12 pgs.

Evans, M.J., et al., "Establishment in culture of pluripotent cells from mouse embryos," Nature, 1981, 292:154-156, 3 pgs.

Gracz, A.D., et al., "*Sox9* Expression Marks a Subset of CD24-expressing Small Intestinve Epithelial Stem Cells the Form Organoids in vitro," Am J Physiol Gastrointest Liver Physiol, 2010, 298:G590-600.

Gradwohl, G., et al., "*neurogenin3* is required for the development of the four endocrine cell lineages of the pancreas," Proc Natl Acad Sci USA, 2000, 97:1607-1611, 5 pgs.

Gregorieff, A., et al., "Wnt signaling in the intestinal epithelium: from endoderm to cancer," Genes & Dev., 2005, 19:877-890, 15 pgs.

Grosse, A.S., et al., "Cell dynamics in fetal intestinal epithelium: implications for intestinal growth and morphogenesis," Development, 2011, 138:4423-4432, 10 pgs.

Hannon. G.J.. "RNA interference." Nature. 2002. 418:244-251, 8 pgs.

Haveri, H., et al., "Transcription factors GATA-4 and GATA-6 in normal and neoplastic human gastrointestinal mucosa," BMC Gastroenterlology, 2008, 8:9.

Hutvagner, G., et al., "A microRNA in a Multiple-Turnover RNAi Enzyme Complex," Science, Sep. 20, 2002, 297:2056-2060, 6 pgs.

Jenny, M., et al., "Neurogenin3 is differentially required for endocrine cell fate specification in the intestinal and gastric epithelium," EMBO J, 2002, 21(23):6338-6347, 10 pgs.

Johannesson, M., et al., "FGF4 and Retinoic Acid Direct Differentiation of hESCs into PDX1-Expressing Foregut Endoderm in a Time- and Concentration-Dependent Manner," PLoS One, Mar. 2009, 4(3):1-13, 13 pgs.

Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pgs.

Johnson, L.R., et al., "Stimulation of rat oxyntic gland mucosal growth by epidermal growth factor," Am. J. Physiol., 1980, 23 8:G45-49, 5 pgs.

Kaji, K., et al., "Virus-free induction of pluripotency and subsequent excision of reprogramming factors," Nature, Apr. 2009, 458:771-775, 6 pgs.

Kawaguchi, Y., et al., "The role of the transcriptional regulator Ptfla in converting intestinal to pancreatic progenitors," Nat Genet, 2002, 32:128-134, 7 pgs.

Klimanskaya, I., et al., "Human embryonic stem cells derived without feeder cells," Lancet, 2005, 365:1636-1641, 6 pgs.

Koo, B-K, et al., "Controlled gene expression in primary *Lgr5* organoid cultures," Nature Methods, Jan. 1, 2012, 9(1):81-83, XP055225249, 5 pgs.

Kubo, A., et al., "Development of definitive endoderm from embryonic stem cells in culture," Development, 2004, 131:1651-1662, 12 pgs.

Kumar, M., et al., "Signals from lateral plate mesoderm instruct endoderm toward a pancreatic fate," Dev Biol, 2003, 259:109-122, 14 pgs.

Lambert, P.F., et al., "Using an immortalized cell line to study the HPV life cycle in organotypic 'raft' cultures," Methods in Molecular Medicine, 2005, 119:141-155.

Lavial, F., et al., "Chicken embryonic stem cells as a non-mammalian embryonic stem cell model," Develop. Growth Diff., 2010, 52:101-114, 14 pgs.

Lee, C. S., et al., "*Neurogenin 3* is essential for the proper specification of gastric enteroendocrine cells and the maintenance of gastric epithelial cell identity," Genes Dev, 2002, 16:1488-1497, 11 pgs.

Liu, J., et al., "A Small-Molecule Agonist of the Wnt Signaling Pathway," Angew Chem Int Ed Engl., 2005, 44(13): 1987-1990, 4 pgs.

Logan, C.Y., et al., "The Wnt Signaling Pathway in Development and Disease," Annu. Rev. Cell Dev. Biol., 2004, 20:781-810, 32 pgs.

Longmire, T.A., et al., "Efficient Derivation of Purified Lung and Thyroid Progenitors from Embryonic Stem Cells," Stem Cell, 2012, 10:398-411, 14 pgs.

López-Díaz, L., et al., "Intestinal Neurogenin 3 directs differentiation of a bipotential secretory progenitor to endocrine cell rather than goblet cell fate," Dev Biol. 2007, 309:298-305, 8 pgs.

Ludwig, T.E., et al., "Derivation of human embryonic stem cells in defined conditions," Nat Biotechnol, 2006, 24:185-187, 3 pgs.

Ludwig, T.E., et al., "Feeder-independent culture of human embryonic stem cells," Nat Methods, 2006, 3:637-646, 10 pgs.

Mahe, M.M., et al., "Establishment of gastrointestinal epithelial organoids," Current Protocols in Mouse Biology, 2013, 3(4):217-240, XP002750112, 31 pgs.

Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.

Martin, G.R., "Teratocarcinomas and mammalian embryogenesis," Science, 1980, 209:768-776, 9pgs.

Martín, M., et al., "Dorsal pancreas agenesis in retinoic acid-deficient *Raldh2* mutant mice," Dev Biol., 2005, 284:399-411, 13 pgs.

(56) References Cited

OTHER PUBLICATIONS

McCracken, K. W., et al., "Modelling human development and disease in pluripotent stem-cell-derived gastric organoids," Nature, Oct. 29, 2014, 516(7531):400-404, XP055210509, 30 pgs.
McLin, V.A., et al., "Repression of Wnt/β-catenin signaling in the anterior endoderm is essential for liver and pancreas development," Development, 2007, 134:2207-2217, 11 pgs.
McManus, M.T., et al., "Gene Silencing in Mammals by Small Interfering RNAs," Nat. Rev. Genet., Oct. 2002, 3:737-747, 13 pgs.
Meerbrey, K.L., et al., "The pINDUCER lentiviral toolkit for inducible RNA interference in vitro and in vivo," Proc Natl Acad Sci USA, 2011, 108:3665-3670, 6 pgs.
Mills, J.C., et al., "Gastric Epithelial Stem Cells," Gastroenterology, 2011, 140:412-424, 13 pgs.
Miyabayashi, T., et al., "Wnt/β-catenin/CBP signaling maintains long-term murine embryonic stem cell pluripotency," Proc Natl Acad Sci USA, 2007, 104(13):5668-5673, 6 pgs.
Molotkov, A., et al., "Retinoic Acid Generated by *Raldh2* in Mesoderm is Required for Mouse Dorsal Endodermal Pancreas Development," Dev Dyn, 2005, 232:950-957, 8 pgs.
Mou, H., et al., "Generation of Multipotent Lung and Airway Progenitors from Mouse ESCs and Patient-Specific Cystic Fibrosis iPSCs," Stem Cell, 2012, 10:385-397, 13 pgs.
Muñoz, M., et al., "Conventional pluripotency markers are unspecific for bovine embiyonic-derived cell-lines," Theriogenology, 2008, 69:1159-1164, 6 pgs.
Neiiendam, J.L., et al., "An NCAM-derived FGF-receptor agonist, the FGL-peptide, induces neurite outgrowth and neuronal survival in primary rat neurons," J. Neurochem., 2004, 91(4):920-935, 17 pgs.
Noguchi, T-A.K., et al., "Generation of stomach tissue from mouse embryonic stem cells," Nature Cell Biology, 2015, 17(8):984-993, XP055225165, 20 pgs.
Okita, K., et al., "Generation of Mouse Induced Pluripotent Stem Cells Without Viral Vectors," Science, 2008, 322(59031:949-953, 6 pgs.
Okita, K., et al., "An Efficient Nonviral Method to Generate Integration-Free Human-Induced Pluripotent Stem Cells from Cord Blood and Peripheral Blood Cells," Stem Cells, 2013, 31:458-466, 9 pgs.
Olbe, L., et al., "A Mechanism by Which *Helicobacter pylori* Infection of the antrum Contributes to the Development of Duodenal Ulcer," Gastroenterology, 2001, 110:1386-1394, 9 pgs.
Ootani, A. et al., "Sustained in vitro intestinal epithelial culture within a Wnt-dependent stem cell niche," Nat Med, 2009, 15:701-706, 14 pgs.
Paddison, P.J., et al., "RNA interference: the new somatic cell genetics?", Cancer Cell, 2002, 2:17-23, 7 pgs.
Pai, R., et al., "Deoxycholic Acid Activates β-Catenin Signaling Pathway and Increases Colon Cell Cancer Growth and Invasiveness," Mol Biol Cell., 2004, 15(5):2156-2163, 8 pgs.
Paris, D.B.B.P., et al., "Equine embryos and embryonic stem cells: Defining reliable markers of pluripotency," Theriogenology, 2010, 74:516-524, 9 pgs.
Parkin, D.M., "The global health burden of infection-associated cancers in the year 2002," Int. J. Cancer, 2006, 118:3030-3044, 15 pgs.
Peek, R.M., Jr., et al., "*Helicobacter pylori* cagA+ Strains and Dissociation of Gastric Epithelial Cell Proliferation From Apoptosis," J. Natl. Cancer Inst, 1997, 89:863-868, 7 pgs.
Peek, R.M., Jr., "*Helicobacter pylori* infection and disease: from humans to animal models," Dis Model Mech, 2008, 1:50-55, 6 pgs.
Petitte, J.N., et al., "Avian pluripotent stem cells," Mech, of Develop., 2004, 121:1159-1168, 10 pgs.
Richards, M., et al., "The Transcriptome Profile of Human Embryonic Stem Cells as Defined by SAGE," Stem Cells, 2004, 22:51-64, 14 pgs.
Rohrschneider, M.R., et al., "Polarity and cell fate specification in the control of *C. elegans* gastrulation," Dev. Dyn., 2009, 238(4):789-796, 15 pgs.
Sancho, E., et al., "Signaling Pathways in Intestinal Development and Cancer," Annu. Rev. Cell Dev. Biol., 2004, 20:695-723, 31 pgs.
Sato, T., et al., "Single Lgr5 stem cells build crypt-villus structures in vitro without a mesenchymal niche," Nature, 2009, 459:262-265, 5 pgs.
Schonhoff, S.E., et al., "*Neurogenin 3*-expressing progenitor cells in the gastrointestinal tract differentiate into both endocrine and non-endocrine cell types," Dev Biol, 2004, 270:443-454, 12 pgs.
Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Shan, J., et al., "Identification of a Specific Inhibitor of the Dishevelled PDZ Domain," Biochemistry, 2005, 44(47):15495-15503, 9 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Spear, P.C., et al., "Interkinetic nuclear migration: A mysterious process in search of a function," Develop. Growth Differ., 2012, 54:306-316, 12 pgs.
Speer, M.D., A.L., et al., "Murine Tissue-Engineered Stomach Demonstrates Epithelial Differentiation," Journal of Surgical Research, Mar. 22, 2011, 171(1):6-14, XP028317226, 9 pgs.
Spence, J.R., et al., "Translational Embryology: Using Embryonic Principles to Generate Pancreatic Endocrine Cells from Embryonic Stem Cells," Developmental Dynamics, 2007, 236:3218-3227, 10 pgs.
Stadtfeld, M., et al., "Induced pluripotent stem cells generated without viral integration," Science, 2008, 322(5903):945-949, 12 pgs.
Taipale, J., et al., "The Hedgehog and Wnt signalling pathways in cancer," Nature, 2001, 411:349-354, 8 pgs.
Takahashi, K. et al., "Induction of Pluripotent Stem Cells from Adult Human Fibroblasts by Defined Factors," Cell, 2007, 131:861-872, 12 pgs.
Takahashi, K., et al., "Induction of Pluripotent Stem Cells from Mouse Embryonic and Adult Fibroblast Cultures by Defined Factors," Cell, 2006, 126:663-676, 14 pgs.
Teo, A.K.K., et al., "Activin and BMP4 Synergistically Promote Formation of Definitive Endoderm in Human Embryonic Stem Cells," Stem Cells, 2012, 30:631-642, 12 pgs.
Thomson, J. A., et al., "Embryonic Stem Cell Lines Derived from Human Blastocysts," Science, 1998, 282(5391):1145-1147, 4 pgs.
Tiso, N., et al., "BMP signalling regulates anteroposterior endoderm patterning in zebrafish," Mech Dev, 2002, 118:29-37, 9 pgs.
Tuschl, T., et al., "Targeted mRNA degradation by double-stranded RNA in vitro," Genes Dev., 1999, 13:3191-3197, 8 pgs.
Van Breemen, R.B., et al., "Caco-2 cell permeability assays to measure drug absorption," Expert Opin. Drug Metab. Toxicol., Aug. 2005, 1(2):175-185, 11 pgs.
Verzi, M.P., et al., "Role of the Homeodomain Transcription Factor Bapx1 in Mouse Distal Stomach Development," Gastroenterology, 2009, 136:1701-1710, 10 pgs.
Wang, J., et al., "Mutant Neurogenin-3 in Congenital Malabsorptive Diarrhea," New England Journal of Medicine, 2006, 355:270-280, 11 pgs.
Wang, Z., et al., "Retinoic acid regulates morphogenesis and patterning of posterior foregut derivatives," Dev Biol, 2006, 297:433-445.
Wells, J.M., et al., "Early mouse endoderm is patterned by soluble factors from adjacent germ layers," Development, 2000, 127:1563-1572, 10 pgs.
Wen, S. et al., "*Helicobacter pylori* virulence factors in gastric carcinogenesis," Cancer Lett., 2009, 282:1-8, 8 pgs.
Woltjen, K., et al., "*piggyBac* transposition reprograms fibroblasts to induced pluripotent stem cells," Nature, 2009, 458:766-770, 8 pgs.
Xia, H.H-X., et al. "Antral-Type Mucosa in the Gastric Incisura, Body, and Fundus (Antralization): A Link Between *Helicobacter pylori* Infection and Intestinal Metaplasia?", Am. J. Gastroenterol., 2000, 95:114-121, 8 ps.

(56) References Cited

OTHER PUBLICATIONS

Yamada, S., et al. "Differentiation of immature enterocytes into enteroendocrine cells by *Pdx1* overexpression," Am. J. Physiol. Gastrointest. Liver Pyshiol., 2001, 281:G229-G236, 8 pgs.

Yuan, Y., et al., "Peptic ulcer disease today," Nat Clin Pract Gastroenterol Hepatol, 2006, 3:80-89 10 pgs.

Zhang, Q, et al., "Small-molecule synergist of the Wnt/β-catenin signaling pathway," Proc Natl Acad Sci USA, 2007, 104(18):7444-7448, 6 pgs.

Zhou, H., et al., "Generation of Induced Pluripotent Stem Cells Using Recombinant Proteins," Cell Stem Cell, 2009, 4(5):381-384, 4 pgs.

Zhou, Q., et al., "In vivo reprogramming of adult pancreatic exocrine cells to β-cells," Nature, 2008, 455: 627-632, 6 pgs.

European Exam Report dated Sep. 28, 2017 for Application No. EP 15728704.6. 4 pgs.

International Search Report dated Feb. 9, 2012 for Application No. PCT/US2011/035518. 7 pgs.

International Preliminary Report on Patentability and Written Opinion dated Nov. 6, 2012 for Application No. PCT/US2011/035518, 5 pgs.

International Search Report and Written Opinion dated Dec. 15, 2015 for Application No. PCT/US2015/032626, 19 pgs.

International Search Report and Written Opinion dated Jan. 19, 2017 for Application No. PCT/US2016/058864, 11 pgs.

International Search Report and Written Opinion dated Aug. 14, 2017 for Application No. PCT/US2017/013109, 17 pgs.

U.S. Appl. No. 15/312,939, filed Nov. 21, 2016, Wells et al.
U.S. Appl. No. 15/627,588, filed Jun. 20, 2017, Wells et al.
U.S. Appl. No. 61/332,178, filed May 6, 2010.
U.S. Appl. No. 62/003,719, filed May 28, 2014.

European Exam Report dated May 18, 2018 for Application No. EP 15791404.5, 3 pgs.

International Search Report and Written Opinion dated Jun. 14, 2018 for Application No. PCT/US2018/018585, 14 pgs.

Ader. M., et al., "Modeling human development in 3D culture," Current Opinion in Cell Biology, 2014, 31:23-28, 6 pgs.

Aurora, M., et al., "hPSC-derived lung and intestinal organoids as models of human fetal tissue," Developmental Biology, 2016, 420:230-238, 9 pgs.

Baptista, P.M., et al., "The Use of Whole Organ Decellularization for the Generation of a Vascularized Liver Organoid," Hepatology, 2011, 53(2):604-617, 14 pgs.

Barker, N., et al., "Tissue-Resident Adult Stem Cell Populations of Rapidly Self-Renewing Organs," Cell Stem Cell, Dec. 2010, 7:656-670, 15 pgs.

Bartfeld, S., et al., "Stem cell-derived organoids and their application for medical research and patient treatment," J Mol Med, 2017, 95:729-738, 10 pgs.

Baumann, K., "Colonic organoids for drug testing and colorectal disease modelling," Nature Reviews Molecular Cell Biology, Jul. 2017, 1 pg.

Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.

Bruens, L., et al., "Expanding the Tissue Toolbox: Deriving Colon Tissue from Human Pluripotent Stem Cells," Cell Stem Cell, Jul. 2017, 21(1):3-5, 3 pgs.

Brugmann, S.A., et al., "Building additional complexity to in vitro-AQmQA intestinal tissues," Stem Cell Research & Therapy, 2013, 4(Suppl 1):S1, 5 pgs.

Cao, L., et al., "Development of Intestinal Organoids as Tissue Surrogates: Cell Composition and the Epigenetic Control of Differentiation," Molecular Carcinogenesis, 2015, 54:189-202, 14 pgs.

Cieslar-Pobuda, A., et al., The expression pattern of PFKFB3 enzyme distinguishes between induced-pluripotent stem cells and cancer stem cells, Oncotarget, 6(30):29753-29770, 18 pgs.

Clevers, H., "Modeling Development and Disease with Organoids," Cell, Jun. 2016, 165:1586-1597, 12 pgs.

Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.

Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.

Dedhia, P.H., et al., "Organoid Models of Human Gastrointestinal Development and Disease," Gastroenterology, 2016, 150:1098-1112, 15 pgs.

Ezashi, T., et al., "Low $O_2$ tensions and the prevention of differentiation of hES cells," PNAS, Mar. 2005, 102(13):4783-4788, 6 pgs.

Fatehullah, A., et al., "Organoids as an in vitro model of human development and disease," Nature CellBiology, Mar. 2106, 18(3):246-254, 9 pgs.

Finkbeiner, S.R., et al., "A Gutsy Task: Generating Intestinal Tissue from Human Pluripotent Stem Cells," Dig Dis Sci, 2013, 58:1176-1184, 9 pgs.

Finkbeiner, S.R., et al., "Stem Cell-Derived Human Intestinal Organoids as an Infection Model for Rotaviruses," mBio, Jul./Aug. 2012, 3(4):e00159-12, 6 pgs.

Gessner, R.C., et al., "Functional ultrasound imaging for assessment of extracellular matrix scaffolds used for liver organoid formation," Biomaterials, 2013, 34:9341-9351, 11 pgs.

Gouon-Evans, V., et al., "BMP-4 is required for hepatic specification of mouse embryonic stem cell-derived definitive endodeim," Nature Biotechnology, Nov. 2006, 24(11):1402-1411, 10 pgs.

Han, M-E., et al., "Gastric stem cells and gastric cancer stem cells," Anatomy & Cell Biology, 2013, 46:8-18, 11 pgs.

Howell, J.C., et al., "Generating intestinal tissue from stem cells: potential for research and therapy," Regen Med., 6(6):743-755, 22 pgs.

Huch, M., et al., "Lgr5$^+$ liver stem cells, hepatic organoids and regenerative medicine," Regen. Med., 2013, 8(4):385-387, 3 pgs.

Huch, M., et al., "Modeling mouse and human development using organoid cultures," Development, 2015, 142:3113-3125, 13 pgs.

Kostrzewski, T., et al., "Three-dimensional perfused human in vitro model of non-alcoholic fatty liver disease," World J Gastroenterol, 2017, 23(2):204-215, 13 pgs.

Kretzschmar, K., et al., "Organoids: Modeling Development and the Stem Cell Niche in a Dish," Developmental Cell, Sep. 2016, 38:590-600, 11 pgs.

Kuratnik, A., et al., "Intestinal organoids as tissue surrogates for toxicological and pharmacological studies," Biochemical Pharmacology, 2013, 85:1721-1726, 6 pgs.

Li, Y., et al., "In vitro organogenesis from pluripotent stem cells," Organogenesis, Jun. 2014, 10(2):159-163, 5 pgs.

Lu, Y., et al., "A Novel 3D Liver Organoid System for Elucidation of Hepatic Glucose Metabolism," Biotechnol Bioeng., Feb. 2012, 109(2):595-604, 21 pgs.

McCracken, K.W., "Mechanisms of endoderm patterning and directed differentiation of human stem cells into foregut tissues," Dissertation, Graduate School of the University of Cincinnati, Jun. 19, 2014, 185 pgs.

Ogaki, S et al., "Wnt and Notch Signals Guide Embryonic Stem Cell Differentiation into the Intestinal Lineages," Stem Cells, 2013, 31:1086-1096, 11 pgs.

Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.

Pastula, A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pgs.

Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).

(56) References Cited

OTHER PUBLICATIONS

Ramachandran, S.D., et al., "In Vitro Generation of Functional Liver Organoid-Like Structures Using Adult Human Cells," Plos One, Oct. 2015, 14 pgs.
Ray, K., "Engineering human intestinal organoids with a functional ENS," Nature Reviews Gastroenterology & Hepatology, Nov. 2016, 1 pg.
Saito, M., et al., "Reconstruction of liver organoid using a bioreactor," World J Gastroenterol, Mar. 2006, 12(12):1881-1888, 8 pgs.
Sampaziotis, F., et al., "Potential of Human Induced Pluripotent Stem Cells in Studies of Liver Disease," Hepatology, Jul. 2015, 62(1):303-311, 9 pgs.
Sasai, Y., "Next-Generation Regenerative Medicine: Organogenesis from Stem Cells in 3D Culture," Cell Stem Cell, May 2013, 12:520-530, 11 pgs.
Schlieve, C.R., et al., "Created of Warm Blood and Nerves: Restoring an Enteric Nervous System in Organoids," Cell Stem Cell, Jan. 2017, 20:5-7, 3 pgs.
Shah, S.B., et al., "Cellular self-assembly and biomaterials-based organoid models of development and diseases," Acta Biomaterialia, 2017, 53:29-45, 17 pgs.
Sinagoga, K.L., et al., "Generating human intestinal tissues from pluripotent stem cells to study development and disease," The EMBO Journal, 2015, 34(9):1149-1163, 15 pgs.
Snykers, S., et al., "In Vitro Differentiation of Embryonic and Adult Stem Cells into Hepatocytes: State of the Art," Stem Cells, 2009, 27:577-605, 29 pgs.
Soto-Gutierrez, A., et al., "Engineering of an Hepatic Organoid to Develop Liver Assist Devices," Cell Transplant, 2010, 19(6):815-822, 12 pgs.
Sugawara, T., et al., "Organoids recapitulate organs?," Stem Cell Investig, 2018, vol. 5, Iss. 3, 4 pgs.
Sui, L., et al., "Signaling pathways during maintenance and definitive endoderm differentiation of embiyonic stem cells," Int J Dev Bio, 2013, 57:1-12, 12 pgs.
Sun, Y., et al., "Genome engineering of stem cell organoids for disease modeling," Protein Cell, 2017, 8(5):315-327, 13 pgs.
Tamminen, K., et al., "Intestinal Commitment and Maturation of Human Pluripotent Stem Cells is Independent fo Exogenous FGF4 and R-spondin1," PLOS One, Jul. 2015, 10(7):e0134551, 19 pgs.
Toivonen, S., et al., "Activin A and Wnt-dependent specification of human definitive endoderm cells," Experimental Cell Research, 2013, 319:2535-2544, 10 pgs.
Tsakmaki, A., et al., "3D intestinal organoids in metabolic research: virtual reality in a dish," Current Opinion in Pharmacology, 2017, 37:51-58, 8 pgs.
Wang, A., et al., "Generating cells of the gastrointestinal system: current approaches and applications for the differentiation of human pluripotent stem cells," J Mol Med, 2012, 90:763-771, 9 pgs.
Workman, M.J., "Generating 3D human intestinal organoids with an enteric nervous system," Thesis, Graduate School of the University of Cincinnati, Oct. 2014, 61 pgs.
Xinaris, C., et al., "Organoid Models and Applications in Biomedical Research," Nephron, 2015, 130:191-199, 9 pgs.
Yin, C., et al., "Hepatic stellate cells in liver development, regeneration, and cancer," The Journal of Clinical Investigation, May 2013, 123(5):1902-1910, 9 pgs.
Adorini, L., et al., "Farnesoid X receptor targeting to treat nonalcoholic steatohepatitis," Drug Discovery Today, Sep. 2012, 17(17/18):988-997, 10 pgs.
Altman, G.H., et al., "Cell differentiation by mechanical stress," The FASEB Journal, 2001, 16(2):270-272, 13 pgs.
Bohorquez, D.V., et al., "An Enteroendocrine Cell—Enteric Glia Connection Revealed by 3D Electron Microscopy," PLOS One, Feb. 2014, 9(2):e89881, 13 pgs.
Cabezas, J., et al., "Nonalcoholic Fatty Liver Disease: A Pathological View," Liver Biopsy—Indications, Procedures, Results, Chapter 8, InTech, 2012, pp. 161-188, 29 pgs.

Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484, 16 pgs.
Date, S., et al., "Mini-Gut Organoids: Reconstitution of the Stem Cell Niche," Annual Review of Cell and Developmental Biology, Nov. 2015, 31:269-289.
Discher, D.E., et al., "Growth Factors, Matrices, and Forces Combine and Control Stem Cells," Science, Jun. 2009, 324:1673-1677, 5 pgs.
Eicher, A.K., et al., "Translating Developmental Principles to Generate Human Gastric Organoids," Cellular and Molecular Gastroenterology and Hepatology, 2018, 5(3):353-363, 11 pgs.
Gori, M., et al., "Investigating nonalcoholic Fatty Liver Disease in a Liver-on-a-Chip Microfluidic Device," PLOS One, Jul. 2016, 11(7):e0159729, 15 pgs.
Green, M.D., et al., "Generation of anterior foregut endoderm from human embryonic and induced pluripotent stem cells," Nature Biotechnology, Mar. 2011, 29(3):267-272, 7 pgs.
Guilak, F., et al., "Control of Stem Cell Fate by Physical Interactions with the Extracellular Matrix," Cell Stem Cell, Jul. 2009, 5:17-26, 10 pgs.
Hannon, N.R.F., et al., "Generation of Multipotent Foregut Stem Cells from Human Pluripotent Stem Cells," Stem Cell Reports, Oct. 2013, 1:293-306, 14 pgs.
Hardy, T., et al., "Nonalcoholic fatty liver disease: new treatments," Curr Opin Gastroenterol, May 2015, 31(3): 175-183, 9 pgs.
Katoh, M., "WNT Signaling in Stem Cell Biology and Regenerative Medicine," Current Drug Targets, 2008, 9(7):565-570, 6 pgs.
Kim, T-H., et al., "Stomach development, stem cells and disease," Development, 2016, 143:554-565, 12 pgs.
Koike, M., et al., "Effects of mechanical strain on proliferation and differentiation of bone marrow stromal cell line ST2," J Bone Miner Metab, 2005, 23:219-225, 7 pgs.
Kolahchi, A.R., et al., "Microfluidic-Bases Multi-Organ Platforms for Drag Discovery," Micromachines, 2016, 7(162): 1-33, 33 pgs.
Lin, C., et al., "The application of engineered liver tissues for novel drag discovery," Expert Opinion on Drag Discoveiy, 2015, 10(5):519-540.
Luo, X., et al., "Generation of endoderm lineages from pluripotent stem cells," Regenerative Medicine, 2017, 12(1):77-89, 13 pgs.
McCracken, K.W., et al., "Mechanisms of embryonic stomach development," Seminars in Cell & Development Biology, 2017, 66:36-42, 7 pgs.
Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.
Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.
Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.
Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 10 pgs.
Park, H.R., et al., "Lipotoxicity of Palmaitic Acid on Neural Progenitor Cells and Hippocampal Neurogenesis," Toxicol Res, 2011, 27(2):103-110, 8pgs.
Park, J.S., et al., "Differential Effects of Equiaxial and Uniaxial Strain on Mesenchymal Stem Cells," Biotechnology and Bioengineering, Nov. 2004, 88(3):359-368, 10 pgs.
Park, J..S., et al., "The effect of matrix stiffness on the differentiation of mesenhymal stem cells in response to TGF-β," Biomaterials, 2011, 32:3921-3930, 10 pgs.
Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.

(56) References Cited

OTHER PUBLICATIONS

Pompaiah, M., et al., "Gastric Organoids: An Emerging Model System to Study *Helicobacter pylori* Pathogenesis," Molecular Pathogenesis and Signal Transduction by Helicobacter pylori, Current Topics in Microbiology and Immunology, N. Tegtmeyer, et al., (eds.), 2017, pp. 149-168.
Qi, M-C., et al., "Mechanical strain induces osteogenic differentiation: Cbfa1 and Ets-1 expression in stretched rat mesenchymal stem cells," Int J Oral Maxillofac Surg, 2008, 37:453-458, 6 pgs.
Reilly, G.C., et al., "Intrinsic extracellular matrix properties regulate stem cell differentiation," Journal of Biomechanics, 2010, 43:55-62, 8 pgs.
Rennert, K., et al., "A microfluidically perfused three dimensional human liver model," Biomaterials, 2015, 71:119-131, 13 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saha, S., et al., "Inhibition of Human Embryonic Stem Cell Differentiation by Medical Strain," Journal of Cellular Physiology, 2006, 206:126-137, 12 pgs.
Schmelter, M., et al., "Embryonic stem cells utilize reactive oxygen species as transducers of mechanical strain-induced cardiovascular differentiation," The FASEB Journal, Jun. 2006, 20(8):1182-1184, 16 pgs.
Schuppan, D., et al., "Non-alcoholic steatohepatitis: Pathogenesis and novel therapeutic approaches," Journal of Gastroenterology and Hepatology, 2013, 28(Suppl 1):68-76, 9 pgs.
Shimizu, N., et al., "Cyclic strain induces mouse embryonic stem cell differentiation into vascular smooth muscle cells by activating PDGF receptorβ," J Appl Physiol, 2008, 104:766-772, 7 pgs.
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.
Skardal, A., et al., "Organoid-on-a-chip and body-on-a-chip systems for drug screening and disease modeling," Drug Discovery Today, Sep. 2016, 21(9):1399-1411, 13 pgs.
Snoeck, H-W., "Generation of Anterior Foregut Derivatives from Pluripotent Stem Cells," Stem Cells Handbook, S. Sell (ed.), 2013, pp. 161-175.
Sonntag, F., et al., "Design and prototyping of a chip-based multi-micro-organoid culture system for substance testing, predictive to human (substance) exposure," Journal of Biotechnology, 2010, 148:70-75, 6 pgs.
Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.
Willet, S.G., et al., "Stomach Organ and Cell Lineage Differentiation: From Embryogenesis to Adult Homeostasis," Cellular and Molecular Gastroenterology and Hepatology, 2016, 2(5):546-559, 14 pgs.
Zhang, W., et al., "Elastomeric Free-Form Blood Vessels for Interconnecting Organs on Chip Systems," Lab Chip, Apr. 2016, 16(9):1579-1586, 19 pgs.
Zhang, Y.S., et al., "Multisensor-integrated organs-on-chips platforms for automated and continual in situ monitoring of organoid behaviors," PNAS Early Edition, 2017, 10 pgs.
Zhang, Y.S., et al., "Seeking the right context for evaluating nanomedicine: from tissue models in petri dishes to microfluidic organs-on-a-chip," Nanomedicine (Lond.), 2015, 10(5):685-688, 4 pgs.
Zhou, J., et al., "The Potential for Gut Organoid Derived Interstitial Cells of Cajal in Replacement Therapy," International Journal of Molecular Sciences, Sep. 2017, 18:1-17, 17 pgs.
International Search Report and Written Opinion dated Jan. 18, 2018 for Application No. PCT/US2017/059865, 12 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
Agopian, V.G., et al., "Intestinal stem cell organoid transplantation generates neomucosa in dogs," J. Gastrointest. Surg., Jan. 23, 2009, 13:971-982, 12 pgs.
Anderson, G., et al., "Loss of enteric dopaminergic neurons and associated changes in colon motility in an MPTP mouse model of Parkinson's disease," Exp Neurol, Sep. 2007, 207:4-12, 16 pgs.
Anlauf, M., et al., "Chemical coding of the human gastrointestinal nervous system: cholinergic, VIPergic, and catecholaminergic phenotypes," The Journal of Comparative Neurology, 2003, 459:90-111, 22 pgs.
Avansino, J.R., et al., "Orthotopic transplantation of intestinal mucosal organoids in rodents," Surgery, Sep. 2006, 140:423-434, 12 pgs.
Baetge, G., et al., "Transient catecholaminergic (TC) cells in the vagus nerves and bowel of fetal mice: relationship to the development of enteric neurons," Developmental Biology, 1989, 132:189-211, 23 pgs.
Bajpai, R., et al., "CHD7 cooperates with PBAF to control multipotent neural crest formation," Nature, Feb. 18, 2010, 463:958-962, 7 pgs.
Bergner, A. J., et al., "Birthdating of myenteric neuron subtypes in the small intestine of the mouse," The Journal of Comparative Neurology, 2014, 522:514-527, 14 pgs.
Blaugrund, E., et al., "Distinct subpopulations of enteric neuronal progenitors defined by time of development, sympathoadrenal lineage markers and *Mash-1*-dependence," Development 122, 1996, 309-320, 12 pgs.
Burns, A.J., et al., "Neural stem cell therapies for enteric nervous system disorders," Nature Reviews/Gastroenterology & Hepatology, May 2014, 11:317-328, 12 pgs.
Campbell, F.C., et al., "Transplantation of cultured small bowel enterocytes," Gut, 1993, 34:1153-1155, 4pgs.
Chen, T-W., et al., "Ultrasensitive fluorescent proteins for imaging neuronal activity," Nature, Jul. 18, 2013, 499:295-300, 8 pgs.
Cheng, X., et al., "Self-renewing endodermal progenitor lines generated from human pluripotent stem cells," Cell Stem Cell, Apr. 6, 2012, 10:371-384, 14 pgs.
Costa, M., et al., "A method for genetic modification of human embryonic stem cells using electroporation," Nature Protocols, Apr. 5, 2007, 2:792-796, 5 pgs.
Curchoe, C.L., et al., "Early acquisition of neural crest competence during hESCs neuralization," PloS One, Nov. 2010, 5:1-17, 17 pgs.
D'Amour, K.A., et al., "Efficient differentiation of human embryonic stem cells to definitive endoderm," Nature Biotechnology, Dec. 2005, 23:1534-1541, 8 pgs.
Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.
Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.
Fordham, R.P., et al., "Transplantation of expanded fetal intestinal progenitors contributes to colon regeneration after injury," Cell Stem Cell, Dec. 5, 2013, 13:734-744, 11 pgs.
Fu, M., et al., "*HOXB5* expression is spatially and temporarily regulated in human embryonic gut during neural crest cell colonization and differentiation of enteric neuroblasts," Developmental Dynamics, 2003, 228:1-10, 10 pgs.
Fu, M., et al., "Embryonic development of the ganglion plexuses and the concentric layer structure of human gut: a topographical study," Anatomy and Embryology, Feb. 27, 2004, 208:33-41, 10 pgs.
Furness, J.B., "The enteric nervous system and neurogastroenterology," Nature Reviews/Gastroenterology & Hepatology, May 2012, 9:286-294, 9 pgs.

(56) References Cited

OTHER PUBLICATIONS

Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.
Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.
Hao, M.M., et al., "Development of enteric neuron diversity," J. Cell. Mol. Med., 2009 13:1193-1210, 18 pgs.
Hockemeyer, D., et al., "Genetic engineering of human ES and iPS cells using TALE nucleases," Nat Biotechnol., 2012, 29:731-734, 8 pgs.
Huebsch, N., et al., "Automated video-based analysis of contractility and calcium flux in human-induced pluripotent stem cell-derived cardiomyocytes cultured over different spatial scales," Tissue Engineering: Part C, 2015, 21:467-479, 15 pgs.
Jung, P., et al., "Isolation and in vitro expansion of human colonic stem cells," Nature Medicine, Oct. 2011, 17:1225-1227, 3 pgs.
Juno, R.J., et al., "A serum factor after intestinal resection stimulates epidermal growth factor receptor signaling and proliferation in intestinal epithelial cells," Surgery, Aug. 2002, 132:377-383, 7 pgs.
Juno, R.J., et al., "A serum factor(s) after small bowel resection induces intestinal epithelial cell proliferation: effects of timing, site, and extent of resection," Journal of Pediatric Surgery, Jun. 2003, 38:868-874, 7 pgs.
Kabouridis, P.S., et ah, "Microbiota controls the homeostasis of glial cells in the gut lamina propria," Neuron, Jan. 21, 2015, 85:289-295, 8 pgs.
Kosinski, C., et al., "Indian hedgehog regulates intestinal stem cell fate through epithelial-mesenchymal interactions during development," Gastroenterology, Sep. 2010, 139:893-903, 17 pgs.
Kovalenko, P.L., et al., "The correlation between the expression of differentiation markers in rat small intestinal mucosa and the transcript levels of schlafen 3," JAMA Surg., Sep. 4, 2013, 148:1013-1019, 7 pgs.
Kroon, E., et al., "Pancreatic endoderm derived from human embryonic stem cells generates glucose-responsive insulin-secreting cells in vivo," Nature Biotechnology, Apr. 2008, 26:443-452, 10 pgs.
Kudoh, T., et al., "Distinct roles for Fgf, Wnt and retinoic acid in posteriorizing the neural ectoderm," Development, 2002, 129:4335-4346,12 pgs.
Lahar, N., et al., "Intestinal suhepithelial myofibroblasts support in vitro and in vivo growth of human small intestinal epithelium," PLoS One, Nov. 2011, 6:e26898, 9 pgs.
Lancaster, M.A., et al., "Organogenesis in a dish: modeling development and disease using organoid technologies," Science, Jul. 18, 2014, 345:283 & 1247125-1-9, 11 pgs.
Le Douarjn, N.M., et al., "Neural crest cell plasticity and its limits," Development 131, 2004, 4637-4650, 14 pgs.
Lee, G., et al., "Isolation and directed differentiation of neural crest stem cells derived from human embryonic stem cells," Nature Biotechnology, Dec. 2007, 25:1468-1475, 9 pgs.
Levin, D.E., et al., "Human tissue-engineered small intestine forms from postnatal progenitor cells," Journal of Pediatric Surgery, 2013, 48:129-137, 9 pgs.
Lindley, R. M., et al., "Human and Mouse Enteric Nervous System Neurosphere Transplants Regulate the Function of Aganglionic Embryonic Distal Colon," Gastroenterology, Jul. 2008, 135:205-216, 18 pgs.
Lui, V.C., et al., "Perturbation of hoxb5 signaling in vagal neural crests down-regulates ret leading to intestinal hypoganglionosis in mice," Gastroenterology, 2008, 134:1104-1115, 12 pgs.
McCracken, K. W., "Generating human intestinal tissue from pluripotent stem cells in vitro," Nat Protoc., 2011, 6:1920-1928, 18 pgs.
McKeown, S.J., et al., "Hirschsprung disease: a developmental disorder of the enteric nervous system," Wiley Interdisciplinary Reviews Developmental Biology, Jan./Feb. 2013, 2:113-129, 17 pgs.

McLin, V.A., et al., "The role of the visceral mesoderm in the development of the gastrointestinal tract," Gastroenterology, Jun. 2009, 136:2074-2091, 18 pgs.
Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.
Obermayr, F., et al., "Development and developmental disorders of the enteric nervous system," Nature Reviews/Gastroenterology & Hepatology, Jan. 2013, 10:43-57, 15 pgs.
Saffrey, M.J., "Cellular changes in the enteric nervous system during ageing," Developmental Biology, 2013, 382:344-355, 12 pgs.
Sasselli, V., et al., "The enteric nervous system," Developmental Biology, Jan. 2012, 366:64-73, 10 pgs.
Sato, T., et al., "Long-term expansion of epithelial organoids from human colon, adenoma, adenocarcinoma, and Barrett's epithelium," Gastroenterology, Nov. 2011, 141:1762-1772, 11 pgs.
Simon-Assmann, P., et al., "In vitro models of intestinal epithelial cell differentiation," Cell Biol Toxicol, 2007, 23:241-256, 17 pgs.
Spence, J.R., et al., "Directed differentiation of human pluripotent stem cells into intestinal tissue in vitro," Nature, Feb. 3, 2011, 470:105-109, 6 pgs.
Tait, I.S., et al., "Colonic mucosal replacement by syngeneic small intestinal stem cell transplantation," The American Journal of Surgery, Jan. 1994, 167:67-72, 6 pgs.
Tait, I.S., et al., "Generation of neomucosa in vivo by transplantation of dissociated rat postnatal small intestinal epithelium," Differentiation, 1994 56:91-100, 10 pgs.
Takaki, M., et al., "In vitro formation of enteric neural network structure in a gut-like organ differentiated from mouse embryonic stem cells," Stem Cells, 2006, 24:1414-1422, 9 pgs.
Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.
Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.
Wang, F., et al., "Isolation and characterization of intestinal stem cells based on surface marker combinations and colony-formation assay," Gastroenterology, 2013, 145:383-395.el-e21, 34 pgs.
Warlich, E., et al., "Lentiviral vector design and imaging approaches to visualize the early stages of cellular reprogramming," Mol. Ther., Apr. 2011, 19:782-789, 9 pgs.
Watson, C.L., et al., "An in vivo model of human small intestine using pluripotent stem cells," Nature Medicine, Nov. 2014, 20:1310-1314, 7 pgs.
Wells, J.M., et al., "How to make an intestine," Development, 2014, 141:752-760, 9 pgs.
Williamson, R.C.N., et al., "Humoral stimulation of cell proliferation in small bowel after transection and resection in rats," Gastroenterology, 1978, 75:249-254, 6 pgs.
Young, H.M., et al., "Expression of Ret-, p75NTR-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M., et al., "GDNF is a chemoattractant for enteric neural cells," Developmental biology, Dec. 19, 2000, 229:503-516, 14 pgs.
Yui, S., et al., "Functional engraftment of colon epithelium expanded in vitro from a single adult Lgr5(+) stem cell," Nature Medicine, Apr. 2012, 18:618-623, 8 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
Zorn, A.M., et al., "Vertebrate endoderm development and organ formation," Annu. Rev. Cell Dev. Biol., 2009, 25:221-251, 36 pgs.
International Search Report and Written Opinion dated Jan. 25, 2016 for Application No. PCT/US2015/055956, 16 pgs.

(56) References Cited

OTHER PUBLICATIONS

International Preliminary Report on Patentability dated Apr. 18, 2017 for Application No. PCT/US2015/055956, 8 pgs.
U.S. Appl. No. 62/065,131, filed Oct. 17, 2014.
Arora, N., et al., "A process engineering approach to increase organoid yield," Development, 2017, 144:1128-1136, 9pgs.
Asai, A., et al., "Paracrine signals regulate human liver organoid maturation from induced pluripotent stem cells," Development, 2017, 144:1056-1064, 9 pgs.
Eberhard, J., et al., "A cohort study of the prognostic and treatment predictive value of SATB2 expression in colorectal cancer," British Journal of Cancer, 2012, 106:931-938, 8 pgs.
Li, Z., et al., "SATB2 is a sensitive marker for lower gastrointestinal well-differentiated neuroendocrine tumors," Int J Clin Exp Pathol, 2015, 8(6):7072-7082, 11 pgs.
McCauley, H. A., et al., "Pluripotent stem cell-derived organoids: using principles of developmental biology to grow human tissues in a dish," Development, 2017, 144:958-962, 5 pgs.
McCracken, K.W., et al., "Wnt/β-catenin promotes gastric fundus specification in mice and humans," Nature, Jan. 2017, 541(7636): 182-187, 31 pgs.
Munera, J.O., et al., "Generation of Gastrointestinal Organoids from Human Pluripotent Stem Cells," Organ Regeneration, In: Tsuji, T., (eds), Organ Regeneration. Methods in Molecular Biology, vo. 1597, Humana Press, New York, NY, 2017, 11 pgs.
Munera, J.O., et al., "Differentiation of Human Pluripotent Stem Cells into Colonic Organoids via Transient Activation of BMP Signaling," Cell Stem Cell, Jul. 2017, 21(1):51-64.e6, 21 pgs.
Rankin, S.A., et al., "Timing is everything: Reiterative Wnt, BMP and RA signaling regulate developmental competence during endoderm organogenesis," Developmental Biology, Feb. 1, 2018, 434(1):121-132, 12 pgs.
Workman, M.J., et al., "Engineered human pluripotent-stem-cell-derived intestinal tissues with a functional enteric nervous system," Nat Med, Jan. 2017, 23(1):49-59, 29 pgs.
Zachos, N.C., et al., "Human Enteroids/Colonoids and Intestinal Organoids Functionally Recapitulate Normal Intestinal Physiology and Pathophysiology," The Journal of Biological Chemistiy, Feb. 2016, 291(8):3759-3766, 8 pgs.
International Search Report and Written Opinion dated Feb. 21, 2018 for Application No. PCT/US2017/064600, 15 pgs.
Singaporean Written Opinion dated Oct. 19, 2017 for Application No. SG11201609953X, 8 pgs.
Stark, R., et al., "Development of an endoluminal intestinal lengthening capsule," Journal of Pediatric Surgery, 2012, 47:136-141, 6 pgs.
European Exam Report dated Jul. 4, 2018 for Application No. EP 15728704.6. 3 pgs.
International Searching Authority Invitation to Pay Additional Fees and, Where Applicable, Protest Fee, dated Jun. 27, 2018 for Application No. PCT/US/2018/029083, 3 pgs.
Buta, C., et al., "Reconsidering pluripotency tests: Do we still need teratoma assays?" Stem Cell Research, 2013, 11:552-562, 11 pgs.
Fon Tacer, K., et al., "Research Resource: Comprehensive Expression Atlas of the Fibroblast Growth Factor System in Adult Mouse," Mol Endocrinol, Oct. 2010, 24(10):2050-2064, 15 pgs.
Gomez, M.C., et al., "Derivation of cat embryonic stem-like cells from in vitro-produced blastocysts on homologous and heterologous feeder cells," Theriogenology, 2010, 74:498-515, 18 pgs.
Jean, C., et al., "Pluripotent genes in avian stem cells," Develop Growth Differ, 2013, 55:41-51, 11 pgs.
Ornitz, D.M., et al., "The Fibroblast Growth Factor signaling pathway," WIREs Dev Biol, 2015, 4:215-266, 52 pgs.
Prakash, R., "Regulation of WNT Genes in Stem Cells Development and Organogenesis," IJP, Jun. 2014, 1(6):366-372, 7 pgs.
International Search Report and Written Opinion dated Sep. 28, 2018 for Application No. PCT/US2018/029083, 14 pgs.
An, W.F., et al., "Discovery of Potent and Highly Selective Inhibitors of GSK3b," Molecular Libraries, Probe Report, May 2014, 115 pgs.
Chang, H-M., et al., "BMP15 Suppresses Progesterone production by Down-Regulating StAR via ALK3 in Human Granulosa Cells," Molecular Endocrinology, 2013, 27:2093-2104, 12 pgs.
Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. Reference unavailable.
Deng, H., et al., "Effects of all-trans retinoic acid on the differentiation of neural stem cells and the expression of c-myc gene," Chinese Journal of Tissue Engineering Research, Mar. 18, 2007, 11(11):2039-2042. Reference unavailable.
Krausova, M., et al., "Wnt signaling in adult intestinal stem cells and cancer," Cellular Signalling, 2014, 26:570-579, 10 pgs.
Lim, D.A., et al., "Noggin Antagonizes BMP Signaling to Create a Niche for Adult Neurogenesis," Neuron, Dec. 2000, 28:713-726, 14 pgs.
McMahon, J.A., et al., "Noggin-mediated antagonism of BMP signaling is required for growth and patterning of the neural tube and somite," Genes & Development, May 1998, 12:1438-1452, 15 pgs.
Ornitz, D.M., et al., "FGF signaling pathways in endochondral and intramembranous bone development and human genetic disease," Genes & Development, Jun. 2002, 16:1446-1465, 21 pgs.
Pan, Q., *Physiology*, University of Science and Technology of China Press, Jan. 31, 2014, pp. 149-150. Reference unavailable.
Que, J., et al., "Morphogenesis of the trachea and esophagus: current players and new roles for noggin and Bmps," Differentiation, 2006, 74:422-437, 16 pgs.
Raju, R., et al., "A Network Map of FGF-1/FGFR Signaling System," Journal of Signal Transduction, Apr. 2014, 2014:1-16, Article ID 962962, 16 pgs.
Su, N., et al., "Role of FGF/FGFR signaling in skeletal development and homeostasis: learning from mouse models," Bone Research, 2014, 2:14003, 24 pgs.
Wan, W., et al., "The Role of Wnt Signaling in the Development of Alzheimer's Disease: A Potential Therapeutic Target?", BioMed Research International, 2014, 2014:1-9, Article ID 301575, 9 pgs.
Yanagita, M., "Modulator of bone morphogenetic protein activity in the progression of kidney diseases," Kidney International, 2006, 70:989-993, 5 pgs.
Yu, Y., *Chinese Studies on Disease Signaling Pathway and Targeted Therapy*, Anhui Science and Technology Press, May 31, 2013, p. 363. Reference unavailable
Chinese Office Action, and Preliminary Search Report, dated Jan. 30, 2019 for Application No. CN 201580034910.4, 11 pgs.
Israeli Office Action dated Nov. 29, 2018 for Application No. IL 249253, 8 pgs.
Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.
Trisno, S.L., et al., "Esophageal Organoids from Human Pluripotent Stem Cells Delineate Sox2 Functions during Esophageal Specification," Cell Stem Cell, 2018, 23:501-515, 23 pgs.
International Search Report and Written Opinion dated Jan. 8, 2019 for Application No. PCT/US2018/054635, 16 pgs.
Ahnfelt-Ronne, J., et al., "An improved method for three-dimensional reconstruction of protein expression patterns in intact mouse and chicken embryos and organs," J. Histochem. Cytochem., 2007, 55:925-930, 6 pgs.
Aronson, B.E., et al., "GATA4 represses an ileal program of gene expression in the proximal small intestine by inhibiting the acetylation of histone H3, lysine 27," Biochim, Biophys. Acta, 2014, 1839(11): 1273-1282, 31 pgs.
Bartfeld, S., et al., "In Vitro Expansion of Human Gastric Epithelial Stem Cells and Their Responses to Bacterial Infection," Gastroenterology, Jan. 2015, 148(1):126-136, 22 pgs.
Battle, M.A., et al., "GATA4 is essential for jejunal function in mice," Gastroenterology, 2008, 135:1676-1686, 17 pgs.
Bernstein, B.E., et al., "The NIH Roadmap Epigenomics Mapping Consortium," Nat Biotechnol. 2010; 28(10):1045-1048, 9 pgs.

(56) References Cited

OTHER PUBLICATIONS

Beuling, E., et al., "Co-Localization of Gata4 and Hnf1α in the Gastrointestinal Tract is Restricted to the Distal Stomach and Proximal Small Intestine," Gastroenterology, AGA Abstracts, Abstract T1933, 2007a, 132:A586, 1 pg.

Beuling, E., et al., "Conditional Gata4 deletion in mice induces bile acid absorption in the proximal small intestine," Gut, 2010, 59(7):888-895, 19 pgs.

Beuling, E., et al., "Fog Cofactors Partially Mediate Gata4 Function in the Adult Mouse Small Intestine," Gastroenterology, AGA Abstracts, Abstract W1467, 2007b, 132:A692-A693, 2 pgs.

Beuling, E., et al., "GATA4 mediates gene repression in the mature mouse small intestine through interactions with Friend of GATA (FOG) cofactors," Dev Biol, 2008a, 322(1):179-189, 23 pgs.

Beuling, E., et al., "The Absence of GATA4 in the Distal Small Intestine Defines the Ileal Phenotype," Gastroenterology, ABA Abstract, Abstract 602, 2008b, 134:A83-A84, 2 pgs.

Bonilla-Claudio, M., et al., "Bmp signaling regulates a dose-dependent transcriptional program to control facial skeletal development," Development, 2012, 139:709-719, 11 pgs.

Bosse, T., et al., "Gata4 and Hnf1α are partially required for the expression of specific intestinal genes during development," Am J Physiol Gastrointest Liver Physiol, 2007, 292:G1302-G1314, 13 pgs.

Bouchi, R., et al., "FOXO1 Inhibition Yields Functional Insulin-Producing Cells in Human Gut Organoid Cultures," Nat Commun, 2014, 5:4242, 24 pgs.

Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.

Choi, E., et al., "Cell lineage distribution atlas of the human stomach reveals heterogeneous gland populations in the gastric antrum," Gut, 2014, 63(11): 1711-1720, 20 pgs.

Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.

De Santa Barbara, P., et al., "Bone Morphogenetic Protein Signaling Pathway Plays Multiple Roles During Gastrointestinal Tract Development," Developmental Dynamics, 2005, 234:312-322, 11 pgs.

Dobreva, G., et al., "SATB2 Is a Multifunctional Determinant of Craniofacial Patterning and Osteoblast Differentiation," Cell, 2006, 125:971-986, 16 pgs.

Driver, I., et al., "Specification of regional intestinal stem cell identity during Drosophila metamorphosis," Development, 2014, 141:1848-1856, 9pgs.

Duluc, I., et al., "Fetal Endoderm Primarily Holds the Temporal and Positional Infoimation Required for Mammalian Intestinal Development," The Journal of Cell Biology, 1994, 126(1):211-221, 11 pgs.

Fagerberg, L., et al., "Analysis of the Human Tissue-specific Expression by Genome-wide Integration of Transcriptomics and Antibody-based Proteomics," Mol Cell Proteomics, 2014, 13:397-406, 10 pgs.

Finkbeiner, S.R., et al., "Transcriptome-wide Analysis Reveals Hallmarks of Human Intestine Development and Maturation In Vitro and In Vivo," Stem Cell Reports, 2015, 4:1140-1155, 16 pgs.

Fitzpatrick, D.R., et al., "Identification of SATB2 as the cleft palate gene on 2q32-q33," Human Molecular Genetics, 2003, 12(19):2491-2501, 11 pgs.

Genthe, J.R., et al., "Ventromorphins: A new class of small molecule activators of the canonical BMP signaling pathway," ACS Chem Biol, 2017, 12(9):2436-2447, 21 pgs.

Georgas, K.M., et al., "An illustrated anatomical ontology of the developing mouse lower urogenital tract," Development, 2015, 142:1893-1908, 16 pgs.

Ginestet, C., Book Review in the Journal of the Royal Statistical Society. Series A (Statistics in Society) (2011), of ggplot2: Elegant Graphics for Data Analysis, by H. Wickham, 2009; 174(1):245, 2 pgs.

Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6pgs.

Goldenring, J.R., et al., "Overexpression of Transforming Growth Factor-α Alters Differentiation of Gastric Cell Lineages," Dig. Dis. Sci., 1996, 41(4):773-784, 12 pgs.

Guo, Z., et al., "Injury-induced BMP signaling negatively regulates Drosophila midgut homeostasis," J Cell Biol., 2013, 201(6):945-961, 17 pgs.

Gyorgy, A.B., et al., "SATB2 interacts with chromatin-remodeling molecules in differentiating cortical neurons" European Journal of Neuroscience, 2008, 27:865-873, 9 pgs.

Haramis, A.-P.G., et al., "De Novo Crypt Formation and Juvenile Polyposis on BMP Inhibition in Mouse Intestine," Science, 2004, 303:1684-1686, 4 pgs.

Hardwick, J.C.H., et al., "Bone Morphogenetic Protein 2 is Expressed by, and Acts Upon, Mature Epithelial Cells in the Colon," Gastroenterology, 2004,126:111-121, 11 pgs.

He, X.C., et al., "BMP signaling inhibits intestinal stem cell self-renewal through suppression of Wnt-β-catenin signaling," Nature Genetics, 2004, 36(10): 1117-1121, 5 pgs.

Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.

Hoffmann, W., "Current Status on Stem Cells and Cancers of the Gastric Epithelium," Int. J. Mol. Sci., 2015, 16:19153-19169, 17 pgs.

Holland, P.W.H., et al., "Classification and nomenclature of all human homeobox genes," BMC Biology, 2007, 5:47, 29 pgs.

Huh, W.J., et al., "Ménétrier's Disease: Its Mimickers and Pathogenesis," Journal of Pathology and Translational Medicine, 2016; 50:10-16, 7 pgs.

Jeejeebhoy, K.N., "Short bowel syndrome: a nutritional and medical approach," CMAJ, 2002, 166(10):1297-1302, 6 pgs.

Johnston, T.B., et al., "Extroversion of the Bladder, Complicated by the Presence of Intestinal Openings on the Surface of the Extroverted Area," J Anat Physiol, 1913, 48(Pt 1):89-106, 18 pgs.

Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.

Kim, B-M., et al., "Regulation of mouse stomach development and Barx1 expression by specific microRNAs," Development, 2011, 138:1081-1086, 6 pgs.

Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.

Kohlnhofer, B.M., et al., "GATA4 Regulates Epithelial Cell Proliferation to Control Intestinal Growth and Development in Mice," Cellular and Molecular Gastroenterology and Hepatology, 2016, 2(2):189-209, 21 pgs.

Kraus, M.R.C., et al., "Patterning and shaping the endoderm in vivo and in culture," Current Opinion Genetics & Development., 2012, 22:347-353, 7 pgs.

Lambrecht, N.W.G., et al., "Identification of the K efflux channel coupled to the gastric H-K-ATPase during acid secretion," Physiological Genomics, 2005, 21:81-91, 11 pgs.

Lameris, A.L., et al., "Expression profiling of claudins in the human gastrointestinal tract in health and during inflammatory bowel disease," Scandinavian Journal of Gastroenterology, 2013, 48:58-69, 12 pgs.

Langmead, G., et al., "Ultrafast and memory-efficient alignment of short DNA sequences to the human genome," Genome Biology, 2009, 10:R25, 10 pgs.

Lennerz, J.K.M., et al., "The Transcription Factor MIST1 is a Novel Human Gastric Chief Cell Marker Whose Expression is Lost in Metaplasia, Dysplasia, and Carcinoma," The American Journal of Pathology, 2010, 177(3):1514-1533, 20 pgs.

Li, H., et al., "TreeFam: a curated database of phylogenetic trees of animal gene families," Nucleic Acids Research, 2006, 34:D572-D580, 9 pgs.

(56) References Cited

OTHER PUBLICATIONS

Li, L., "BMP Signaling Inhibits Intestinal Stem Cell Self-Renewal Through Antagonizing Wnt Signaling," Gastroenterology, AASLD Abstracts, Abstract S1223, 2005, 128:A702, 1 pg.
McGovern, D.P.B., et al., "Genome-wide association identifies multiple ulcerative colitis susceptibility loci," Nature Genetics, 2010, 42(4):332-337, 8 pgs.
Molodecky, N.A., et al., "Increasing Incidence and Prevalence of the Inflammatory Bowel Diseases With Time, Based on Systematic Review," Gastroenterology, 2012, 142:46-54, 51 pgs.
Moser, A.R., et al., "A dominant mutation that predisposes to multiple intestinal neoplasia in the mouse," Science, 1990, 247(4940):322-324, 3 pgs.
Nielsen, C., et al., "Gizzard Formation and the Role of *Bapx1*," Developmental Biology, 2001, 231:164-174, 11 pgs.
Nomura, S., et al., "Evidence for Repatterning of the Gastric Fundic Epithelium Associated With Ménétrier's Disease and TGFα Overexpression," Gastroenterology, 2005, 128:1292-1305, 14 pgs.
Park, Y.H., et al., "Review of Atrophic Gastritis and Intestinal Metaplasia as a Premalignant Lesion of Gastric Cancer," Journal of Cancer Prevention, 2015, 20(1):25-40, 16 pgs.
Patankar, J.V., et al., "Intestinal Deficiency of Gata4 Protects from Diet-Induced Hepatic Steatosis by Suppressing *De Novo* Lipogenesis and Gluconeogenesis in Mice," Journal of Hepatology, Posters, Abstract 1253, 2012, 56:S496, 1 pg.
Patankar, J.V., et al., "Intestinal GATA4 deficiency protects from diet-induced hepatic steatosis," Journal of Hepatology, 2012, 57:1061-1068, 8 pgs.
Ramalingam, S., et al., "Distinct levels of *Sox9* expression mark colon epithelial stem cells that form colonoids in culture," Am J Physiol Gastrointest Liver Physiol,, 2012, 302:G10-G20, 11 pgs.
Ramsey, V.G., et al., "The maturation of mucus-secreting gastric epithelial progenitors into digestive-enzyme secreting zymogenic cells requires *Mist1*," Development, 2007, 134:211-222, 12 pgs.
Rankin, S.A., et al., "A Molecular Atlas of *Xenopus* Respiratory System Development," Developmental Dynamics, 2015, 244:69-85, 17 pgs.
Rankin, S.A., et al., "Suppression of Bmp4 signaling by the zinc-finger repressors Osr1 and Osr2 is required for Wnt/β-catenin-mediated lung specification in *Xenopus*," Development, 2012, 139:3010-3020, 11 pgs.
Ratineau, C., et al., "Endoderm- and mesenchyme-dependent commitment of the differentiated epithelial cell types in the developing intestine of rat," Differentiation, 2003, 71:163-169, 7 pgs.
Roberts, D. J., et al., "Sonic hedgehog is an endodermal signal inducing *Bmp-4* and *Hox* genes during induction and regionalization of the chick hindgut," Development, 1995, 121:3163-3174, 12 pgs.
Rodríguez-Piñeiro, A.M., et al., "Studies of mucus in mouse stomach, small intestine, and colon. II. Gastrointestinal mucus proteome reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Roth, R.B., et al., "Gene expression analyses reveal molecular relationships among 20 regions of the human CNS," Neurogenetics, 2006, 7:67-80, 14 pgs.
Savidge, T.C., et al., "Human intestinal development in a severe-combined immunodeficient xenograft model," Differentiation, 1995, 58:361-371, 11 pgs.
Savin, T., et al., "On the growth and form of the gut," Nature. 2011. 476:57-62, 7 pgs.
Schumacher, M.A., et al., "The use of murine-derived ftrndic organoids in studies of gastric physiology," J. Physiol., 2015, 593(8):1809-1827, 19 pgs.
Sheehan-Rooney, K., et al., "Bmp and Shh Signaling Mediate the Expression of *satb2* in the Pharyngeal Arches," PLoS One, Mar. 2013, 8(3):e59533, 10 pgs.

Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shyer, A.E., et al., "Bending Gradients: How the Intestinal Stem Cell Gets Its Home," Cell, 2015, 161:569-580, 13 pgs.
Siegel, R., et al., "Colorectal Cancer Statistics, 2014," CA Cancer J Clin, 2014, 64:104-117, 14 pgs.
Sigalet, D.L., "The Role of the Enteric Neuronal System in Controlling Intestinal Function," Clinical Surgety Society Magazine, 2003, 64:214. (Reference unavailable).
Speer, A.L., et al., "Fibroblast Growth Factor 10-Fibroblast Growth Factor Receptor 2b Mediated Signaling is Not Required for Adult Glandular Stomach Homeostasis," PLoS ONE, 2012, 7(11):e49127, 12 pgs.
Stange, D.E., et al., "Differentiated Troy$^+$ chief cells act as 'reserve' stem cells to generate all lineages of the stomach epithelium," Cell, 2013, 155(2):357-368, 26 pgs.
Thanasupawat, T., et al., "INSL5 is a novel marker for human enteroendocrine cells of the large intestine and neuroendocrine tumours," Oncology Reports, 2013, 29:149-154, 6 pgs.
Trapnell, C., et al., "Differential gene and transcript expression analysis of RNA-seq experiments with TopHat and Cufflinks," Nat Protoc, 2013, 7(3):562-578, 39 pgs.
Uppal, K., et al., "Meckel's Diverticulum: A Review," Clinical Anatomy, 2011, 24:416-422, 7 pgs.
Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.
Van Klinken, B.J-W., et al., "MUC5B is the prominent mucin in human gallbladder and is also expressed in a subset of colonic goblet cells," The American Journal of Physiology, 1998, 274:G871-G878, 8 pgs.
Walker, E.M., et al., "GATA4 and GATA6 regulate intestinal epithelial cytodifferentiation during development," Developmental Biology, 2014, 392:283-294, 12 pgs.
Walton, K.D., et al., "Epithelial Hedgehog signals direct mesenchymal villus patterning through BMP," Abstracts / Developmental Biology, Program/Abstract # 354, 2009, 331:489, 1 pg.
Walton, K.D., et al., "Hedgehog-responsive mesenchymal clusters direct patterning and emergence of intestinal villi," PNAS, 2012, 109(39):15817-15822, 6 pgs.
Walton, K.D., et al., "Villification in the mouse: Bmp signals control intestinal villus patterning," Development, 2016, 143:427-436, 10 pgs.
Wang, X., et al., "Cloning and variation of ground state intestinal stem cells," Nature, 2015, 522:173-178, 18 pgs.
Wehkamp, J., et al., "Paneth cell antimicrobial peptides: Topographical distribution and quantification in human gastrointestinal tissues," FEBS Letters, 2006, 580:5344-5350, 7 pgs.
Weis, V.G., et al., "Current understanding of SPEM and its standing in the preneoplastic process," Gastric Cancer, 2009, 12:189-197, 9 pgs.
Whissell, G., et al., "The transcription factor GATA6 enables self-renewal of colon adenoma stem cells by repressing BMP gene expression," Nature Cell Biology, 2014, 16(7):695-707, 24 pgs.
Wills, A., et al., "Bmp signaling is necessary and sufficient for ventrolateral endoderm specification in *Xenopus*," Dev Dyn., 2008, 237(8):2177-2186, 18 pgs.
Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of *Hox* genes along the gastrointestinal tract," Congenital Anomalies, 2004, 44:18-26, 9 pgs.
Zbuk, K.M., et al., "Hamartomatous polyposis syndromes," Gastroenterology & Hepatology, 2007, 4(9):492-502, 12 pgs.
Japanese Office Action, Notification of Reasons for Refusal, and First Search Report by Registered Search Organization, dated May 14, 2019 for Application JP 2017-520900, 65 pgs.

(56) References Cited

OTHER PUBLICATIONS

Japanese Office Action, Notice of Reasons for Refusal, and Search Report by Registered Search Organization, dated Apr. 2, 2019 for Application No. JP 2016-569618, 42 pgs.
Singaporean Office Action, Third Written Opinion, dated May 3, 2019 for Application No. SG 11201609953X, 5 pgs.
Singaporean Second Written Opinion dated Sep. 4, 2018 for Application No. SG11201609953X, 6 pgs.
Keung, A.J., et al., "Presentation Counts: Microenvironmental Regulation of Stem Cells by Biophysical and Material Cues," Annu. Rev. Cell Dev. Biol., 2010, 26:533-556, 26 pgs.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Broda T.R., et al., "Generation of Human Antral and Fundic Gastric Organoids from Pluripotent Stem Cells," Nature Protocols, Nov. 2018. vol. 14(1), pp. 28-50.
Burrin D., et al., "Enteral Obeticholic Acid Prevents Hepatic Cholestasis in Total Parenteral Nutrition-Fed Neonatal Pigs," Hepatology, vol. 62, Oct. 2015, p. 307A.
Chauhan R.K., et al., "Genetic and Functional Studies of Hirschsprung Disease," Doctoral Thesis: Department of Clinical Genetics, Erasmus University Rotterdam, the Netherlands, 2016, 202 pages.
Cincinnati Children's Hospital Medical Center, "Scientists Grow Human Esophagus in Lab: Tiny Organoids Enable Personalized Disease Diagnosis, Regenerative Therapies," CCHMC Public Press Release, Sep. 20, 2018, 2 pages.
Crespo M., et al., "Colonic Organoids Derived from Human Induced Pluripotent Stem Cells for Modeling Colorectal Cancer and Drug Testing," Nature Medicine, Jun. 19, 2017, vol. 23, No. 7, pp. 878-884.
Cunningham T.J., et al., "Mechanisms of Retinoic Acid Signalling and its Roles in Organ and Limb Development," Nature Reviews Molecular Cell Biology, vol. 16, No. 2, Jan. 5, 2015, pp. 110-123.
Dekkers R., et al., "A Bioassay Using Intestinal Organoids to Measure CFTR Modulators in Human Plasma," Journal of Cystic Fibrosis, 2015, vol. 14 (2), pp. 178-181.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501/10?clear=10&p10_accession_num=ucin1544098242321181; 160 pages.
Feldstein A.E., et al., "Free Fatty Acids Promote Hepatic Lipotoxicity By Stimulating TNF-α Expression Via a Lysosomal Pathway," Hepatology, Jul. 2004, vol. 40 (1), pp. 185-194.
Guan Y., et al., "Human Hepatic Organoids for the Analysis of Human Genetic Diseases," JCI Insight, Sep. 7, 2017, vol. 2, Issue 17, e94954; 17 pages.
Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.
Kawaguchi Y., et al., "The Role of the Transcriptional Regulator Ptf1 a in Converting Intestinal to Pancreatic Progenitors," Nature Genetics, 2002, vol. 32, pp. 128-134.
Kruitwagen H.S., et al., "SCH-O-5 Long-Term Adult Feline Liver Organoid Cultures for Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis," Stem Cell Reports, Apr. 2017, vol. 8(4), pp. 822-830.
Kuci Z., et al., "Mesenchymal Stromal Cells from Pooled Mononuclear Cells of Multiple Bone Marrow Donors as Rescue Therapy in Pediatric Severe Steroid-Refractory Graft-Versus-Host Disease: A Multicenter Survey," Haematologica, 2016, vol. 101 (8), pp. 985-994.
Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.
Lai F.P.-L., et al., "Correction of Hirschsprung-Associated Mutations in Human Induced Pluripotent Stem Cells Via Clustered Regularly Interspaced Short Palindromic Repeats/Cas9, Restores Neural Crest Cell Function," Gastroenterology, 2017, vol. 153, No. 1, pp. 139-153.
Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.
Mori R., et al., "Micropatterned Organoid Culture of Rat Hepatocytes and HepG2 Cells," Journal of Bioscience and Bioengineering, Sep. 2008, vol. 106(3), pp. 237-242.
Mullin E., "Tiny Human Esophagus Grown in the Lab-Here's Why: Miniature Version of the Organ that Guides Food to the Stomach could Help Scientists Treat a Variety of Medical Ailments," National Geographic, Sep. 20, 2018, downloaded from https://www.nationalgeographic.com/science/2018/news-human-esophagus-grow-n-lab-stem-cells-cancer-health.html, 5 pages.
Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.
Paddison P.J., et al., "Short Hairpin Activated Gene Silencing in Mammalian Cells," Methods in Molecular Biology, 2004, vol. 265, pp. 85-100.
Ramirez-Weber F.A., et al., "Cytonemes: Cellular Processes that Project to the Principal Signaling Center in Drosophila Imaginal Discs," Cell, May 28, 1999, vol. 97, pp. 599-607.
Ricchi M., et al., "Differential Effect of Oleic and Palmitic Acid on Lipid Accumulation and Apoptosis in Cultured Hepatocytes," Journal of Gastroenterology and Hepatology, May 2009, vol. 24, Issue 5, pp. 830-840.
Sandoiu A., "Scientists Create Human Esophagus in Stem Cell First," Medical News Today, Downloaded from https://www.medicalnewstoday.com/articles/323118.phpSep. 21,2018, 4 pages.
Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.
Siller R., et al., "Small-Molecule-Driven Hepatocyte Differentiation of Human Pluripotent Stem Cells," Stem Cell Reports, May 2015, vol. 4, No. 5, pp. 939-952.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Takebe T., et al., "Generation of a Vascularized and Functional Human Liver from an IPSC-derived Organ Bud Transplant," Nature Protocols, Feb. 2014, vol. 9(2), pp. 396-409.
Vu J., et al., "Regulation of Appetite, Body Composition and Metabolic Hormones by Vasoactive Intestinal Polypeptide (VIP)," Journal of Molecular Neuroscience, Apr. 23, 2015, vol. 56, No. 2, pp. 377-387.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.
Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.

(56) References Cited

OTHER PUBLICATIONS

Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.

Zhang Y., et al., "Palmitic and Linoleic Acids Induce ER Stress and Apoptosis in Hepatoma Cells," Lipids in Health and Disease, 2012, vol. 11 (1), 8 pages.

Ajmera, V., et al., "Novel Plasma Biomarkers Associated with Liver Disease Severity in Adults with Nonalcoholic Fatty Liver Disease," Hepatology, 2017, 65(1):65-77, 21 pgs.

Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.

Allard, J., et al., "Immunohistochemical toolkit for tracking and quantifying xenotransplanted human stem cells," Regenerative Medicine, 2014, 9(4):437-452, 11 pgs.

Arroyo, J.D., et al., "Argonaute2 complexes cany apopulationof circulating microRNAs independent of vesicles in human plasma," PNAS, 2011, 108(12):5003-5008, 6 pgs.

Bahar Halpern, K., et al. "Single-cell spatial reconstruction reveals global division of labour in the mammalian liver," Nature, 2017, 542:352-356, 18 pgs.

Bar-Ephraim, Y.E., et al., "Modelling cancer immunomodulation using epithelial organoid cultures," bioRxiv, 2 018, accessed from Http://dx.doi.org/10.1101/377655v1.full, 13 pgs.

Barth, C.A., et al., "Transcellular transport of fluorescein in hepatocyte monolayers: Evidence for functional polarity of cells in culture," Proc Natl Acad Sci USA, 1982, 79:4985-4987, 3 pgs.

Begriche, K., et al., "Drug-induced toxicity on mitochondria and lipid metabolism: Mechanistic diversity and deleterious consequences for the liver," J Hepatol, 2011, 54:773-794, 22 pgs.

Bell, L.N., et al., "Epidemiology of Idiosyncratic Drug-Induced Liver Injury," Semin Liver Dis, 2009, 29(4):337-347, 11 pgs.

Bergeles, C., et al., "From Passive Tool Holders to Microsurgeons: Safer, Smaller, Smarter Surgical Robots," IEEE Trans Biomed Eng, 2014, 61(5):1565-1576, 12 pgs.

Bernardi, P., "The permeability transition pore. Control points of a cyclosporin A-sensitive mitochondrial channel involved in cell death," Biochim Biophys Acta, 1996, 1275:5-9, 5 pgs.

Bharadwaj, S., et al., "Current status of intestinal and multivisceral transplantation," Gastroentrerol Rep (Oxf)., 2017, 5(l):20-28, 9 pgs.

Bhutani, N., et al., Reprogramming towards pluripotency requires AID-dependent DNA demethylation, Nature, 2010, 463(7284): 1042-1047, 17 pgs.

Bohan, T.P., et al., "Effect of L-carnitine treatment for valproate-induced hepatotoxicity," Neurology, 2001, 56:1405-1409, 5 pgs.

Boroviak, T., et al., "Single cell transcriptome analysis of human, marmoset and mouse embryos reveals common and divergent features of preimplantation development," Development, 2018, 145(21):dev167833, 35 pgs.

Bort, R., et al., "Diclofenac Toxicity to Hepatocytes: A Role for Drag Metabolism in Cell Toxicity," J Pharmacol Exp Ther, 1998, 288(1):65-72, 8 pgs.

Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.

Bragdon, B., et al., "Bone Morphogenetic Proteins: A critical review," Cellular Signalling, 2011, 23:609-620, 12 pgs.

Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.

Browning, J.D., et al., "Molecular mediators of hepatic steatosis and liver injury," J Clin Invest, 2004, 114(2):147-152, 6 pgs.

Burke, P., et al., "Towards a single-chip, implantable RFID system: is a single-cell radio possible?" Biomed Microdevices, 2010, 12:589-596, 8 pgs.

Burn, S.F., et al., "Left-right asymmetry in gut development: what happens next?" BioEssays, 2009, 31:1026-1037, 12 pgs.

Caneparo, L., et al., "Intercellular Bridges in Vertebrate Gastrulation," PloS ONE, 2011, 6(5):e20230, 6 pgs.

Capeling, M.M., et al., "Nonadhesive Alginate Hydrogels Support Growth of Pluripotent Stem Cell-Derived Intestinal Organoids," Stem Cell Reports, Feb. 2019, 12(2):381-394, 14 pgs.

Chai, P.R., et al., "Utilizing an Ingestible Biosensor to Assess Real-Time Medication Adherence," J Med Toxicol, 2015, 11:439-444, 6 pgs.

Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.

Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.

Chatterjee, S., et al., "Hepatocyte-based in vitro model for assessment of drug-induced cholestasis," Toxicol Appl Pharmacol, 2014, 274:124-136, 13 pgs.

Chen, B., et al., "Dynamic Imaging of Genomic Loci in Living Human Cells by an Optimized CRISPR/Cas System," Cell, 2013, 155(7):1479-1491, 23 pgs.

Chen, L.Y., et al., "Mass fabrication and delivery of 3D multilayer uTags into living cells," Sci Rep, 2013, 3:2295, 6 pgs.

Chen, Y., et al., "Retinoic acid signaling is essential for pancreas development and promotes endocrine at the expense of exocrine cell differentiation in *Xenopus*," Dev Biol, 2004, 271:144-160, 17 pgs.

Christoffersson, J., et al., "Developing organ-on-a-chip concepts using bio-mechatronic design methodology," Biofabrication, 2017, 9:025023, 14 pgs.

Chughlay, M.F., et al., "N-acetylcysteine for non-paracetamol drug-induced liver injury: a systematic review," Br J Clin Pharmacol, 2016, 81:1021-1029, 9 pgs.

Clarke, L.L., "A guide to Ussing chamber studies of mouse intestine," Am J Physiol Gastrointest Liver Physiol, 2009, 296:G1151-G1166, 16 pgs.

Collier, A. J., et al., "Comprehensive Cell Surface Protein Profiling Identifies Specific Markers of Human Naïve and Primed Pluripotent States," Cell Stem Cell, 2017, 20:874-890, 25 pgs.

Cortez, et al., "Transplantation of human intestinal organoids into the mouse mesentery: A more physiological and anatomic engraftment site," Surgery, 2018, 164:643-650, 8 pgs.

Crocenzi, F.A., et al., "$Ca^{2+}$-Dependent Protein Kinase C Isoforms Are Critical to Estradiol 17β-D-Glucuronide-Induced Cholestasis in the Rat," Hepatology, 2008, 48:1885-1895, 12 pgs.

Cutrin, J.C., et al., "Reperfusion Damage to the Bile Canaliculi in Transplanted Human Liver," Hepatology, 1996, 24:1053-1057, 5 pgs.

Das, R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pgs. Summary only.

Dash, A., et al., "Pharmacotoxicology of clinically-relevant concentrations of obeticholic acid in an organotypic human hepatocyte system," Toxicology In Vitro, 2017, 39:93-103, 11 pgs.

Davidson, M.D., et al., "Long-term exposure to abnormal glucose levels alters drug metabolism pathways and insulin sensitivity in primary human hepatocytes," Sci Rep, 2016, 6:28178, 11 pgs.

Dekkers, J.F., et al., "A functional CFTR assay using primary cystic fibrosis intestinal organoids," Nat Med, 2013, 19(7):939-945, 9 pgs.

Demehri, F.R., et al., "Development of an endoluminal intestinal attachment for clinically applicable distraction enterogenesis device," Journal of Pediatric Surgery, 2016, 51:101-106, 6 pgs.

Demehri, F.R., et al., "Development of an endoluminal intestinal lengthening device using a geometric intestinal attachment approach," Surgeiy, 2015, 158(3):802-811, 10 pgs.

Dumortier, G., et al., "Tolérance hépatique des antipsychotiques atypiques, [Hepatic tolerance of atypical antipsychotic drugs]," L'Encéphale, 2002, 28(1):542-551, 10 pgs.

Dvir-Ginzberg, M., et al., "Liver Tissue Engineering Within Alginate Scaffolds: Effects of Cell-Seeding Density on Hepatocyte Viability, Morphology, and Function," Tissue Eng, 2003, 9(4):757-766, 10 pgs.

(56) References Cited

OTHER PUBLICATIONS

Edling, Y., et al., "Increased sensitivity for troglitazone-induced cytotoxicity using a human in vitro co-culture model," Toxicol In Vitro, 2009, 23:1387-1395, 9 pgs.

Ekser, B., et al., "Comparable outcomes in intestinal retransplantation: Single-center cohort study," The Journal of Clinical and Translational Research, 2018, 32(7):e13290, 10 pgs.

El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.

El Taghdouini, A., et al., "In vitro reversion of activated primary human hepatic stellate cells," Fibrogenesis & Tissue Repair, 2015, 8:14, 15 pgs.

The Encode Project Consortium, "An integrated encyclopedia of DNA elements in the human genome," Nature, 2012, 489:57-74, 18 pgs.

Engmann, J., et al., "Fluid mechanics of eating, swallowing and digestion—overview and perspectives," Food & Function, 2013, 4:443-447, 5 pgs.

Fahrmayr, C., et al., "Phase I and II metabolism and MRP2-mediated export of bosentan in a MDCKII-OATP1B1-CYP3A4-UGT1A1-MRP2 quadruple-transfected cell line," Br J Pharmacol, 2013, 169:21-33, 13 pgs.

Falasca, L., et al., "The effect of retinoic acid on the re-establishment of differentiated hepatocyte phenotype in primary culture," Cell Tissue Res, 1998, 293:337-347, 11 pgs.

Finkenzeller, K., *RFID Handbook: Fundamentals and Applications in Contactless Smart Cards, Radio Frequency Identification and Near-Field Communication, Third Edition*. John Wiley & Sons, Ltd., Chichester, West Sussex, 2010, 8 pgs. (Table of Contents Only).

Fisher, A., et al., "Entacapone-Induced Hepatotoxicity and Hepatic Dysfunction," Mov Disord, 2002, 17:1362-1365, 4 pgs.

Fromenty, B., "Drug-induced liver injury in obesity," J Hepatol, 2013, 58:824-826, 3 pgs.

Gafni, O., et al., "Derivation of novel human ground state naïve pluripotent stem cells," Nature, 2013, 504:282-286, 20 pgs.

Geerts, A., et al., "Formation of Normal Desmin Intermediate Filaments in Mouse Hepatic Stellate Cells Requires Vimentin," Hepatology, 2001, 33:177-188, 12 pgs.

Gerdes, H-H., et al., "Tunneling nanotubes, an emerging intercellular communication route in development," 2013, 130:381-387, 7 pgs.

Giles, D.A., et al., "Thermoneutral housing exacerbates nonalcoholic fatty liver disease in mice and allows for sex-independent disease modeling," Nature Medicine, 2017, 23(7):829-838, 13 pgs.

Glorioso, J.M., et al., "Pivotal Preclinical Trial of the Spheroid Reservoir Bioartificial Liver," J Hepatol, 2015, 63(2):388-398, 27 pgs.

Gomez-Pinilla, P.J., et al., "Ano 1 is a selective marker of interstitial cells of Cajal in the human and mouse gastrointestinal tract," Am J Physiol Gastrointest Liver Physiol, 2009, 296:G1370-G1381, 12 pgs.

Grapin-Botton, A., "Three-dimensional pancreas organogenesis models," Diabetes Obes Metab, 2016, 18(Suppl 1):33-40, 8pgs.

Gregersen, H., et al., "The Zero-Stress State of the Gastrointestinal Tract: Biomechanical and Functional Implications," Digestive Diseases and Sciences, 2000, 45(12):2271-2281, 11 pgs.

Guo, G., et al., "Epigenetic resetting of human pluripotency," Development, 2017, 144:2748-2763, 17 pgs.

Gurdon, J.B., "Adult Frogs Derived from the Nuclei of Single Somatic dells," Dev Biol, 1962, 4:256-273, 18 pgs.

Gurken, A., "Advances in small bowel transplantation," Turk J Surg., 2017, 33(3):135-141, 7 pgs.

Haimovich, G., et al., "Intercellular mRNA trafficking via membrane nanotube-like extensions in mammalian cells," 2017, PNAS, pp. E9873-E9882, 10 pgs.

Han, B., et al., "Microbiological safety of a novel bio-artificial liver support system based on porcine hepatocytes: a experimental study," European Journal of Medical Research, 2012, 17:13, 8 pgs.

Hassan, W., et al., "Reduced Oxidative Stress Contributes to the Lipid Lowering Effects of Isoquercitrin in Free Fatty Acids Induced Hepatocytes," Oxid Med Cell Longev, 2014, 313602, 18 pgs.

Heidari, R., et al., "Factors affecting drug-induced liver injury: antithyroid drugs as instances," Clin Mol Hepatol, 2014, 20:237-248, 12 pgs.

Hernandez, F., et al., "Refining Indications for Intestinal Retransplantation," International Small Bowel Symposium 2013; Abstract 12.241 (online: https://www.tts.org/component/%20tts/?view=presentation &id-13241) Accessed Jun. 12, 2017, 3 pgs.

Hooton, D., et al., "The Secretion and Action of Brush Border Enzymes in the Mammalian Small Intestine," Rev Physiol Biochem Pharmacol, 2015, 168:59-118, 60 pgs.

Hou, P., et al., "Pluripotent Stem Cells Induced from Mouse Somatic Cells by Small-Molecule Compounds," Science, 2013, 341:651-654, 4 pgs.

Hsu, F., et al., "The UCSC Known Genes," Bioinformatics, 2006, 22(9):1036-1046, 11 pgs.

Hu, H., et al., "Long-Term Expansion of Functional Mouse and Human Hepatocytes as 3D Organoids," Cell, 2018, 175:1591-1606, 36 pgs.

Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.

Huch, M., et al., "Long-Term Culture of Genome-Stable Bipotent Stem Cells from Adult Human Liver," Cell, 2015, 160:299-312, 14 pgs.

Hynds, R.E., et al., "The relevance of human stem cell-derived organoid models for epithelial translational medicine," Stem Cells, 2013, 31(3):417-422, 11 pgs.

Ijpenberg, A., et al., "Wtl and retinoic acid signaling are essential for stellate cell development and liver morphogenesis," Dev Biol, 2007, 312:157-170, 14 pgs.

Inoue, H., et al., "iPS cells: a game changer for future medicine," EMBO J, 2014, 33(5):409-417, 9 pgs.

Ito, K., et al., "Temporal Transition of Mechanical Characteristics of HUVEC/MSC Spheroids Using a Microfluidic Chip with Force Sensor Probes," Micromachines, 2016, 7:221, 14 pgs.

Jalan-Sakrikar, N., et al., "Hedgehog Signaling Overcomes an EZH2-Dependent Epigenetic Barrier to Promote Cholangiocyte Expansion," PLoS One, 2016, 11(12):e0168266, 19 pgs.

Kanuri, G., et al., "In Vitro and in Vivo Models of Non-Alcoholic Fatty Liver Disease (NAFLD)," Int J Mol Sci, 2013, 14:11963-11980, 18 pgs.

Karlikow, M., et al., "*Drosophila* cells use nanotube-like structures to transfer dsRNA and RNAi machinery between cells," Scientific Reports, 2016, 6:27085, 9 pgs.

Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.

Kelly, G.M., et al., "Retinoic Acid and the Development of the Endoderm," J Dev Biol, 2015, 3:25-56, 32 pgs.

Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.

Kilens, S., et al., "Parallel derivation of isogenic human primed and naïve induced pluripotent stem cells," Nat Commun, 2018, 9:360, 13 pgs.

Kilpinen, H., et al., "Common genetic variation drives molecular heterogeneity in human iPSCs," Nature, 2017, 546(7658):370-375, 51 pgs.

Kim, D., et al., "HISAT: a fast spliced aligner with low memory requirements," Nature Methods, 2015, 12(4):357-360, 6 pgs.

Kock, K., et al., "A Perspective on Efflux Transport Proteins in the Liver," Clin Pharmacol Ther, 2012, 92(5):599-612, 29 pgs.

Koehler, E.M., et al., "Presence of Diabetes Mellitus and Steatosis is Associated With Liver Stiffness in a General Population: The Rotterdam Study," Hepatology, 2016, 63:138-147, 10 pgs.

Kolodny, G.M., "Evidence for Transfer of Macromolecular RNA Between Mammalian Cells in Culture," Exp Cell Res, 1971, 65:313-324, 12 pgs.

(56) References Cited

OTHER PUBLICATIONS

Kordes, C., et al., "Hepatic stellate cells contribute to progenitor cells and liver regeneration," J Clin Invest, 2014, 124(12):5503-5515, 13 pgs.

Krähenbühl, S., et al., "Toxicity of Bile Acids on the Electron Transport Chain of Isolated Rat Liver Mitochondria," Hepatology, 1994, 19:471-479, 9 pgs.

Kubal, C.A., et al., "Challenges with Intestine and Multivisceral Re-Transplantation: Importance of Timing of Re-Transplantation and Optimal Immunosuppression," Ann Transplant, 2018, 23:98-104, 7 pgs.

Kullak-Ublick, G.A., et al., "Drug induced liver injury: recent advantages in diagnosis and risk assessment," Gut, 2017, 66:1154-1164, 11 pgs.

Kumar, J.A., et al., "Controversies in the Mechanism of Total Parenteral Nutrition Induced Pathology," Children, 2015, 2:358-370, 13 pgs.

Kurpios, N. A., et al., "The direction of gut looping is established by changes in the extracellular matrix and in cell:cell adhesion," PNAS, 2008, 105(25):8499-8506, 8 pgs.

Lê, S., et al., "FactoMineR: An R Package for Multivariate Analysis," Journal of Statistical Software, 2008, 25(1):1-18, 18 pgs.

Le Vee, M., et al., "Polarized expression of drug transporters in differentiated human hepatoma HepaRG cells," Toxicol In Vitro, 2013, 27:1979-1986, 8 pgs.

Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.

Lee, W.M., et al., "Intravenous N-Acetylcysteine Improves Transplant-Free Survival in Early Stage Non-Acetaminophen Acute Liver Failure," Gastroenterology, 2009, 137(3):856-864, 18 pgs.

Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.

Leung, A.A., et al., "Tolerance testing of passive radio frequency identification tags for solvent, temperature, and pressure conditions encountered in an anatomic pathology or biorepositoiy setting," J Pathol Inform, 2010, 1:21, 6 pgs.

Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.

Lin, Y., et al., "Differentiation, Evaluation, and Application of Human Induced Pluripotent Stem Cell-Derived Endothelial Cells," Arterioscler Thromb Vase Biol, 2017, 37:2014-2025, 12 pgs.

Liu, L., et al., "A Review of Locomotion Systems for Capsule Endoscopy," IEEE Rev Biomed Eng, 2015, 8:138-151, 14 pgs.

Loike, J.D., et al., "Opinion: Develop Organoids, Not Chimeras, for Transplantation," The Scientist Magazine, Aug. 2019, (online: https://www.the-scientist.com/news-opinion/opinion--develop-organoids--not-chimeras--for-transplantation-66339), 3 pgs.

Love, M.I., et al., "Moderated estimation of fold change and dispersion for RNA-seq data with DESeq2," Genome Biol, 2014, 15:550, 21 pgs.

Low, L.A., et al., "Organs-on-chips: Progress, challenges, and future directions," Experimental Biology and Medicine, 2017, 242:1573-1578, 6 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.

MacParland, S.A., et al., "Single cell RNA sequencing of human liver reveals distinct intrahepatic macrophage populations," Nat Commun, 2018, 9:4383, 21 pgs.

Mahe, M.M., et al., "In Vivo Model of Small Intestine," Methods Mol Biol, 2017, 1597:229-245, 17 pgs.

Makin, A.J., et al., "A 7-Year Experience of Severe Acetaminophen-Induced Hepatotoxicity (1987-1993)," Gastroenterology, 1995, 109:1907-1916, 10 pgs.

Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.

Mammoto, A., et al., "Mechanosensitive mechanisms in transcriptional regulation," Journal of Cell Science, 2012, 125:3061-3073, 13 pgs.

Marcum, Z.A., et al., "Medication Adherence to Multi-Drug Regimens," Clin Geriatr Med, 2012, 28(2):287-300, 15 pgs.

Marini, F., et al., "pcaExplorer: an R/Bioconductor package for interacting with RNA-seq principal components," BMC Bioinformatics, 2019, 20:331, 8 pgs.

Marini, F., "pcaExplorer: Interactive Visualization of RNA-seq Data Using a Principal Components Approach," bioconductor.org, R package version 2.3.0, 2017, 7 pgs.

Markova, S.M., et al., "Association of *CYP2C9\*2* With Bosentan-Induced Liver Injury," Clin Pharmacol Then, Dec. 2013, 94(6):678-86, 9 pgs.

Marsh, M.N., et al., "A study of the small intestinal mucosa using the scanning electron microscope," Gut, 1969, 10:940-949, 10 pgs.

McCracken, K.W., et al., "Erratum: Wnt/β-catenin promotes gastric fundus specification in mice and humans," Nature, 2017, 543:136, 1 pg.

McKenzie, T. J., et al., "Artificial and Bioartificial Liver Support," Seminars in Liver Disease, 2008, 28(2):210-217, 8 pgs.

Mercaldi, C.J., et al., "Methods to Identify and Compare Parenteral Nutrition Administered From Hospital-Compounded and Premixed Multichamber Bags in a Retrospective Hospital Claims Database," J Parenter Enteral Nutr, 2012, 36(3):330-336, 7 pgs.

Michaut, A., et al., "A cellular model to study drug-induced liver injury in nonalcoholic fatty liver disease: application to acetaminophen," Toxicol Appl Pharmacol, 2016, 292:40-55, 35 pgs.

Miki, T., et al., "Hepatic Differentiation of Human Embryonic Stem Cells is Promoted by Three-Dimensional Dynamic Perfusion Culture Conditions," Tissue Eng: Part C Methods, 2011, 17(5):557-568, 12 pgs.

Mörk, L.M., et a., "Comparison of Culture Media for Bile Acid Transport Studies in Primary Human Hepatocytes," J Clin Exp Hepatol, 2012, 2:315-322, 8 pgs.

Nakamura, T., et al., "Advancing Intestinal Organoid Technology Toward Regenerative Medicine," Cell Mol Gastroenterol Hepatol, 2018, 5:51-60, 10 pgs.

Navarro, V. J., et al., "Drug-Related Hepatotoxicity," N Engl J Med, 2006, 354:731-739, 9 pgs.

Negishi, T., et al., "Retinoic Acid Signaling Positively Regulates Liver Specification by Inducing *wnt2bb* Gene Expression in Medaka," Hepatology, 2010, 51:1037-1045, 9 pgs.

Nelson, B.J., et al., "Microrobots for Minimally Invasive Medicine," Annual Review of Biomedical Engineering, 2010, 12(12):55-85, 33 pgs.

Nelson, C.M., "On Buckling Morphogenesis," JBiomechEng, 2016, 138:021005-1-021005-6, 6 pgs.

Ni, X., et al., "Functional human induced hepatocytes (hiHeps) with bile acid synthesis and transport capacities: A novel in vitro cholestatic model," Sci Rep, 2016, 6:38694, 16 pgs.

Nishida, T., et al., "Rat liver canalicular membrane vesicles contain an ATP-dependent bile acid transport system," Proc Natl Acad Sci USA, 1991, 88:6590-6594, 5 pgs.

Oorts, M., et al., "Drug-induced cholestasis risk assessment in sandwich-cultured human hepatocytes," Toxicol In Vitro, 2016, 34:179-186, 8 pgs.

Orso, G., et al., "Pediatric parenteral nutrition-associated liver disease and cholestasis: Novel advances in pathomechanisms-based prevention and treatment," Dig Liver Dis, 2016, 48:215-222, 8 pgs.

Ouchi, R., et al., "Modeling Steatohepatitis in Humans with Pluripotent Stem Cell-Derived Organoids," Cell Metabolism, Aug. 2019, 30:1-11, 17 pgs.

(56) References Cited

OTHER PUBLICATIONS

Pardal, M.L., et al., "Towards the Internet of Things: An Introduction to RFID technology," RFID Technology-Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.
Pastor, W.A., et al., "TFAP2C regulates transcription in human naïve pluripotency by opening enhancers," Nature Cell Biology, 2018, 20:553-564, 18 pgs.
Pereira, C.F., et al., "Heterokaryon-Based Reprogramming of Human B Lymphocytes for Pluripotency Requires Oct4 but Not Sox2," PLoS Genet, 2008, 4(9):e1000170, 14 pgs.
Pessayre, D., et al., "Central role of mitochondria in drug-induced liver injury," Drug Metab Rev, 2012,44(1):34-87, 54 pgs.
Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.
Poling, H.M., et al., "Mechanically induced development and maturation of human intestinal organoids in vivo," Nat Biomed Eng, 2018, 2(6):429-442, 31 pgs.
Polson, J., et al., "AASLD Position Paper: The Management of Acute Liver Failure," Hepatology, 2005, 41(5):1179-1197, 19 pgs.
Purton, L.E., et al., "All-trans retinoic acid enhances the long-term repopulating activity of cultured hematopoietic stem cells," Blood, 2000, 95:470-477, 8 pgs.
Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.
Ramirez-Weber, F.-A., et al., "Cytonemes: Cellular Processes that Project to the Principal Signaling Center in *Drosophila* Imaginal Discs," Cell, 1999, 97:599-607, 9 pgs.
Rane, A., et al., "Drug Metabolism in the Human Fetus and Newborn Infant," Pediatr Clin North Am, 1972, 19(1):37-49, 11 pgs.
Rao, R.R., et al., "Gene Expression Profiling of Embryonic Stem Cells Leads to Greater Understanding of Pluripotency and Early Developmental Events," Biol Reprod, 2004, 71:1772-1778, 7 pgs.
Rector, R.S., et al., "Mitochondrial dysfunction precedes insulin resistance and hepatic steatosis and contributes to the natural history of non-alcoholic fatty liver disease in an obese rodent model," J Hepatol, 2010, 52(5):727-736, 20 pgs.
Reuben, A., et al. "Drug-Induced Acute Liver Failure: Results of a U.S. Multicenter, Prospective Study," Hepatology, 2010, 52:2065-2076, 12 pgs.
Riedinger, H-J, et al., "Reversible shutdown of replicon initiation by transient hypoxia in Ehrlich ascites cells: Dependence of initiation on short-lived protein," Eur J. Biochem, 1992, 210:389-398, 10 pgs.
Roberts, A., et al., "Identification of novel transcripts in annotated genomes using RNA-Seq," Bioinformatics, 2011, 27(17):2325-2329, 5 pgs.
Roberts, A., et al., "Improving RNA-Seq expression estimates by correcting for fragment bias," Genome Biol, 2011, 12:R22, 14 pgs.
Ronn, R.E., et al., "Retinoic Acid Regulates Hematopoietic Development from Human Pluripotent Stem Cells," Stem Cell Reports, 2015, 4:269-281, 13 pgs.
Rouch, J.D., et al., "Scalability of an endoluminal spring for distraction enterogenesis," Journal of Pediatric Surgery, 2016, 51:1988-1992, 5 pgs.
Roy, S., et al., "Cytoneme-Mediated Contact-Dependent Transport of the *Drosophila* Decapentaplegic Signaling Protein," Science, 2014, 343:1244624-1, 11 pgs.
Russo, M.W., et al., "Liver Transplantation for Acute Liver Failure From Drug Induced Liver Injury in the United States," Liver Transpl, 2004, 10:1018-1023, 6 pgs.
Sachs, N., et al., "A Living Biobank of Breast Cancer Organoids Captures Disease Heterogeneity," Cell, 2018, 172:373-386, 25 pgs.
Saini, A., "Cystic Fibrosis Patients Benefit from Mini Guts," Cell Stem Cell, 2016, 19:425-427, 3 pgs.
Salas-Vidal, E., et al., "Imaging filopodia dynamics in the mouse blastocyst," Developmental Biology, 2004, 265:75-89, 15 pgs.
Sartori-Rupp, A., et al., "Correlative cryo-electron microscopy reveals the structure of TNTs in neuronal cells," Nature Communications, 2019, 10:342, 16 pgs.
Sasai, Y., "Cytosystems dynamics in self-organization of tissue architecture," Nature, 2013, 493:318-326, 9 pgs.
Sato, T., et al., "Snapshot: Growing Organoids from Stem Cells," Cell, 2015, 161:1700-1700e1, 2 pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Shahbazi, M.N., et al., "Self-organization of the human embryo in the absence of maternal tissues," Nature Cell Biology, 2016, 18(6):700-708, 20 pgs.
Shekherdimian, S., et al., "The feasibility of using an endoluminal device for intestinal lengthening," Journal of Pediatric Surgeiy, 2010, 45:1575-1580, 6 pgs.
Shi, X-L., et al., "Effects of Membrane Molecular Weight Cutoff on Performance of a Novel Bioartificial Liver," Artificial Organs, 2011, 35(3):E40-E46, 7 pgs.
Shi, X-L., et al., "Evaluation of a novel hybrid bioartificial liver based on a multi-layer flat-plate bioreactor," World J Gastroenterol, 2012, 18(281:3752-3760, 9 pgs.
Shyer, A.E., et al., "Villification: How the Gut Gets its Villi," Science, 2013, 342:212-218, 7 pgs.
Sim, Y-J., et al., "2i Maintains a Naïve Ground State in ESCs through Two Distinct Epigenetic Mechanisms," Stem Cell Reports, 2017, 8:1312-1328, 17 pgs.
Sitti, M., et al., "Biomedical Applications of Untethered Mobile Milli/Microrobots," Proc IEEE Inst Electr Electron Eng, 2015, 103(2):205-224, 20 pgs.
Slaymaker, I.M., et al., "Rationally engineered Cas9 nucleases with improved specificity," Science, 2016, 351(6268):84-88, 10 pgs.
Sloan, C.A., et al., "ENCODE data at the ENCODE portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci., 1965, 3:47-57, 11 pgs.
Soffers, J.H.M., et al., "The growth pattern of the human intestine and its mesentery," BMC Dev Biol, 2015, 15:31, 16 pgs.
Song, W., et al., "Engraftment of human induced pluripotent stem cell-derived hepatocytes in immunocompetent mice via 3D co-aggregation and encapsulation," Sci Rep, 2015,5:16884, 13 pgs.
Song, Z., et al., "Efficient generation of hepatocyte-like cells from human induced pluripotent stem cells," Cell Res, 2009, 19:1233-1242, 10 pgs.
Spence, J.R., et al., "Vertebrate Intestinal Endoderm Development," Developmental Dynamics, 2011, 240:501-520, 20 pgs.
Stafford, D., et al., "A conserved role for retinoid signaling in vertebrate pancreas development," Dev Genes Evol, 2004, 214:432-441, 10 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drug safety testing: expanding the view and narrowing the focus," Drug Discov Today, 2009, 14(3/4):162-167, 6 pgs.
Stuart, T., et al., "Comprehensive Integration of Single-Cell Data," Cell, 2019, 177:1888-1902, 37 pgs.
Sugimoto, S., et al., "Reconstruction of the Human Colon Epithelium In Vivo," Cell Stem Cell, 2018, 22:171-176, 16 pgs.
Suzuki, A., et al., "Clonal identification and characterization of self-renewing pluripotent stem cells in the developing liver," The Journal of Cell Biology, 2002, 156(1):173-184, 12 pgs.
Tada, M., et al., "Embryonic germ cells induce epigenetic reprogramming of somatic nucleus in hybrid cells," EMBO J, 1997, 16(21):6510-6520, 11 pgs.
Takahashi, S., et al., "Epigenetic differences between naïve and primed pluripotent stem cells," Cellular and Molecular Life Sciences, 2018, 75:1191-1203, 13 pgs.

(56) References Cited

OTHER PUBLICATIONS

Takashima, Y., et al., "Resetting Transcription Factor Control Circuitry toward Ground-State Pluripotency in Human," Cell, 2014, 158(6):1254-1269, 32 pgs.

Takebe, T., et al., "Human iPSC-Derived Miniature Organs: A Tool for Drug Studies," Clin Pharmacol Ther, 2014, 96(3):310-313, 4 pgs.

Takebe, T., et al., "Massive and Reproducible Production of Liver Buds Entirely from Human Pluripotent Stem Cells," Cell Reports, 2017, 21:2661-2670, 11 pgs.

Takebe, T., et al., "Vascularized and Complex Organ Buds from Diverse Tissues via Mesenchymal Cell-Driven Condensation," Cell Stem Cell, 2015, 16:556-565, 10 pgs.

Takebe, T., et al., "Vascularized and functional human liver from an iPSC-derived organ bud transplant," Nature, 2013, 499:481-484, 5 pgs.

Tamm, C., et al., "A Comparative Study of Protocols for Mouse Embryonic Stem Cell Culturing," PLoS ONE, 2013, 8(12):e81156, 10 pgs.

Tamminen, K., et al., "Intestinal Commitment and Maturation of Human Pluripotent Stem Cells is Independent of Exogenous FGF4 and R-spondinl," PLOS One, Jul. 2015, 10(7):e0134551, 19 pgs.

Terry, B.S., et al., "Preliminary Mechanical Characterization of the Small Bowel for In Vivo Robotic Mobility," J. Biomech Eng, 2011, 133:091010-1-09101-7, 7 pgs.

The WNT homepage, "Small molecules in Wnt signalling," Nusse Lab, Jan. 2019, 2 pgs.

Theunissen, T.W., et al., "Systematic Identification of Culture Conditions for Induction and Maintenance of Naïve Human Pluripotency," Cell Stem Cell, 2014, 15:471-487, 47 pgs.

Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.

Tran, K., et al. "Evaluation of regional and whole gut motility using the wireless motility capsule: relevance in clinical practice," Therap Adv Gastroenterol, 2012, 5(4):249-260, 12 pgs.

Trapnell, C., et al., "Transcript assembly and quantification by RNA-Seq reveals unannotated transcripts and isoform switching during cell differentiation," Nat Biotechnol, 2010, 28(5):511-515, 8 pgs.

Troy, D.B. (ed.), Remington: The Science and Practice of Pharmacy, 21$^{st}$ Ed., 2006, Lippincott, Williams & Wilkens, Baltimore, MD, 6 pgs., Table of Contents Only.

Tsedensodnom, O., et al., "ROS: Redux and Paradox in Fatty Liver Disease," Hepatology, 2013, 58(4):1210-1212, 3 pgs.

Tsukada, N., et al., "The Structure and Organization of the Bile Canalicular Cytoskeleton With Special Reference to Actin and Actin-Binding Proteins," Hepatology, 1995, 21(4):1106-1113, 8 pgs.

Tyml, K., et al., "Lipopolysaccharide reduces intercellular coupling in vitro and arteriolar conducted response in vivo," AJP-Heart Circ Physiol, 2001, 281:H1397-H1406, 10 pgs.

The United States Pharmacopeia: The National Formulary (USP 24 NF 19), United States Pharmacopeial Convention, Inc., Rockville, MD, 1999, 4 pgs., Table of Contents Only.

Valadi, H., et al., "Exosome-mediated transfer of mRNAs and microRNAs is a novel mechanism of genetic exchange between cells," Nat Cell Biol, 2007, 9(6):654-659, 17 pgs.

Van De Garde, M.D., et al., "Liver Monocytes and Kupffer Cells Remain Transcriptionally Distinct during Chronic Viral Infection," PLoS One, 2016,11(11):e0166094, 16 pgs.

Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.

Verma, S., et al., "Diagnosis, management and prevention of drug-induced liver injury," Gut, 2009, 58:1555-1564, 10 pgs.

Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.

Wakayama, T., et al., "Full-term development of mice from enucleated oocytes injected with cumulus cell nuclei," Nature, 1998, 394:369-374, 6 pgs.

Wang, S., (Ed.), "The role of homologous genes in the development of appendages," in Basis of Developmental Biology, Press of East China University of Science and Technology, 2014, pp. 184-185, 4 pgs.

Wang, Y., et al., "Hepatic stellate cells, liver innate immunity, and hepatitis C virus," J Gastroenterol Hepatol, 2013, 28(Suppl 1):112-115, 8 pgs.

Want, R., "An Introduction to RFID Technology," IEEE Pervas Comput, 2006, 5:25-33, 9 pgs.

Ware, C.B., "Concise Review: Lessons from Naïve Human Pluripotent Cells," Stem Cells, 2017, 35:35-41, 7 pgs.

Warren, C.R., et al., "Induced Pluripotent Stem Cell Differentiation Enables Functional Validation of GWAS Variants in Metabolic Disease," Cell Stem Cell, 2017, 20:547-557, 18 pgs.

Warren, C.R., et al., "The NextGen Genetic Association Studies Consortium: A Foray into In Vitro Population Genetics," Cell Stem Cell, 2017, 20:431-433, 3 pgs.

Wernig, M., et al., "In vitro reprogramming of fibroblasts into a pluripotent ES-cell-like state," Nature, 2007, 448:318-324, 8 pgs.

Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388el, 23 pgs.

Wiley, L.A., et al., "cGMP production of patient-specific iPSCs and photoreceptors precursor cells to treat retinal degenerative blindness," Scientific Reports, 2016, 6:30742, 16 pgs.

Wilmut, I., et al., "Viable offspring derived from fetal and adult mammalian cells," Nature, 1997, 385:810-813, 4 pgs.

Xu, R., et al., "Association Between Patatin-Like Phospholipase Domain Containing 3 Gene (PNPLA3) Polymorphisms and Non-alcoholic Fatty Liver Disease: A HuGE Review and Meta-Analysis," Sci Rep, 2015, 5:9284, 11 pgs.

Xu, R., et al. (Eds.), "Retinoic acid receptor" in Basis and Clinic of Receptor, Shanghai Science and Technology Press, 1992, pp. 129-131, 2 pgs.

Yanagimachi, M.D., et al., "Robust and Highly-Efficient Differentiation of Functional Monocytic Cells from Human Pluripotent Stem Cells under Serum- and Feeder Cell-Free Conditions," PLoS One, 2013, 8(4):e59243, 9 pgs.

Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.

Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.

Yu, H., et al., "The Contributions of Human Mini-Intestines to the Study of Intestinal Physiology and Pathophysiology," Annu Rev Physiol, 2017, 79:291-312, 22 pgs.

Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.

Zambrano, E., et al., "Total parenteral Nutrition Induced Liver Pathology: An Autopsy Series of 24 Newborn Cases," Pediatr Dev Pathol, 2004, 7:425-432, 8 pgs.

Zborowski, J., et al., "Induction of swelling of liver mitochondria by fatty acids of various chain length," Biochim Biophys Acta, 1963, 70:596-598, 3 pgs.

Zhang, R-R., et al., "Human iPSC-Derived Posterior Gut Progenitors Are Expandable and Capable of Forming Gut and Liver Organoids," Stem Cell Reports, 2018, 10(3):780-793, 14 pgs.

Zhao, Y., et al., "A XEN-like State Bridges Somatic Cells to Pluripotency during Chemical Reprogramming," Cell, 2015, 163:1678-1691, 15 pgs.

Zhong, J., et al., "Continuous-wave laser-assisted injection of single magnetic nanobeads into living cells," Sensors and Actuators B: Chemical, 2016, 230:298-305, 8 pgs.

(56) References Cited

OTHER PUBLICATIONS

Chinese Office Action, the Second Office Action, and Supplementary Search Report, dated Dec. 19, 2019 for Application No. CN 201580034910.4, 11 pgs.
International Search Report and Written Opinion dated Jul. 9, 2018 for Application No. PCT/US2018/027585, 12 pgs.
International Search Report and Written Opinion dated May 7, 2019 for Application No. PCT/US2018/067057, 15 pgs.
International Search Report and Written Opinion dated Oct. 29, 2019 for Application No. PCT/US2019/041985, 13 pgs.
International Search Report and Written Opinion dated Dec. 5, 2019 for Application No. PCT/US2019/050846, 10 pgs.
International Search Report and Written Opinion dated Dec. 13, 2019 for Application No. PCT/US2019/053408, 10 pgs.
U.S. Appl. No. 16/346,190, filed Apr. 30, 2019, by Takebe et al., entitled: "Liver Organoid Disease Models and Methods of Making and Using Same."
U.S. Appl. No. 16/599,620, filed Oct. 11, 2019, by Wells et al., entitled: "Methods and Systems for Converting Precursor Cells Into Intestinal Tissues Through Directed Differentiation."
U.S. Appl. No. 16/603,609, filed Oct. 8, 2019, by Takebe et al., entitled: "Multi Donor Stem Cell Compositions and Methods of Making Same."
U.S. Appl. No. 16/603,611, filed Oct. 8, 2019, by Mahe et al., entitled: "Methods of Making Improved Human Intestinal Organoid Compositions Via Application of Strain and Human Intestinal Organoid Compositions Thereof."
U.S. Appl. No. 16/611,998, filed Nov. 8, 2019, by Takebe et al., entitled: "Liver Organoid Compositions and Methods of Making and Using Same."
Bain C.C., et al., "Constant Replenishment from Circulating Monocytes Maintains the Macrophage Pool in Adult Intestine," Nat Immunol, Oct. 2014, vol. 15 (10), pp. 929-937.
Bain C.C., et al., "Resident and Pro-Inflammatory Macrophages in the Colon Represent Alternative Context-Dependent Fates of the Same Ly6Chi Monocyte Precursors," Mucosal Immunology, May 2013, vol. 6 (3), pp. 498-510.
Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.
Bort R., et al., "Hex Homeobox Gene-Dependent Tissue Positioning is Required for Organogenesis of the Ventral Pancreas," Development, Jan. 21, 2004, vol. 131 (4), pp. 797-806.
Bujko A., et al., "Transcriptional and Functional Profiling Defines Human Small Intestinal Macrophage Subsets," Journal of Experimental Medicine, 2018, vol. 215 (2), pp. 441-458.
Bulmer J.N., et al., "Macrophage Populations in the Human Placenta and Amniochorion," Clinical Experimental Immunology, 1984, vol. 57 (2), pp. 393-403.
Camp J.G., et al., "Multilineage Communication Regulates Human Liver Bud Development from Pluripotency," Nature, 2017, vol. 546 (7659), pp. 533-538.
Campbell E.L., et al., "Transmigrating Neutrophils Shape the Mucosal Microenvironment Through Localized Oxygen Depletion to Influence Resolution of Inflammation," Immunity, 2014, vol. 40(1), pp. 66-77.
Chen Y., et al., "Robust Bioengineered 3D Functional Human Intestinal Epithelium," Scientific Reports, vol. 5 (13708), Sep. 16, 2015, XP055454950, DOI: 10.1038/srep13708, 11 pages.
Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.
Cumano A., et al., "Lymphoid Potential, Probed before Circulation in Mouse, Is Restricted to Caudal Intraembryonic Splanchnopleura," Cell, Sep. 20, 1996, vol. 86 (6), pp. 907-916.
Davies L.C., et al., "Tissue-Resident Macrophages," Nat Immunol, Oct. 2013, vol. 14 (10), pp. 986-995.

DeSchepper S., et al., "Self-Maintaining Gut Macrophages Are Essential for Intestinal Homeostasis," Cell, Oct. 4, 2018, vol. 175 (2), pp. 400-415.
Dolle L., et al., "EpCAM and the Biology of Hepatic Stem/Progenitor Cells," American Journal of physiology gastrointestinal liver physiology, 2015, vol. 308, pp. G233-G250.
Foulke-Abel J., et al., "Human Enteroids as a Model of Upper Small Intestinal Ion Transport Physiology and Pathophysiology," Gastroenterology, Mar. 2016, vol. 150, No. 3, pp. 638-649.
Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.
Gissen P., et al., "Structural and Functional Hepatocyte Polarity and Liver Disease," Journal of Hepatology, 2015, vol. 63, pp. 1023-1037.
Glocker E.O., et al., "Inflammatory Bowel Disease and Mutations Affecting the Interleukin-10 Receptor," N Engl J Med, Nov. 19, 2009, vol. 361 (21), pp. 2033-2045.
Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.
Hentsch B., et al., "Hlx Homeo Box Gene is Essential for an Inductive Tissue Interaction that Drives Expansion of Embryonic Liver and Gut," Genes & Development, 1996, vol. 10 (1), pp. 70-79.
Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.
Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132, 35 pages.
Hoeffel G., et al., "C-Myb-+ Erythro-Myeloid Progenitor-Derived Fetal Monocytes Give Rise to Adult Tissue-Resident Macrophages," Immunity, Apr. 21, 2015, vol. 42 (4), pp. 665-678.
Iacovino M., et al., "HoxA3 is an Apical Regulator of Hemogenic Endothelium," Nat Cell Biol, Jan. 2011, vol. 13 (1), pp. 72-78.
Jørgensen M.C., et al., "Neurog3-Dependent Pancreas Dysgenesis Causes Ectopic Pancreas in Hes1 Mutant Mice," Development, 2018, vol. 145 (17), 11 pages.
Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.
Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.
Lanctot P.M., et al., "The Glycans of Stem Cells," Curr Opin Chern Biol, Aug. 2007, vol. 11(4), pp. 373-380.
Lee G., et al., "Derivation of Neural Crest Cells From Human Pluripotent Stem Cells," Nature Protocols, Mar. 18, 2010, vol. 5(4), pp. 688-701.
Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.
Maheshwari A., et al., "TGF-β2 Suppresses Macrophage Cytokine Production and Mucosal Inflammatory Responses In the Developing Intestine," Gastroenterology, 2011, vol. 140 (1), pp. 242-253.
Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.
Martin M.J., et al., "Human Embryonic Stem Cells Express an Immunogenic Nonhuman Sialic Acid," Nature Medicine, Feb. 2005, vol. 11 (2), pp. 228-232.
McGrath P.S., et al., "The Basic Helix-Loop-Helix Transcription Factor NEUROG3 is Required for Development of the Human Endocrine Pancreas," Diabetes, Jul. 2015, vol. 64, pp. 2497-2505.

(56) References Cited

OTHER PUBLICATIONS

McKimpson W.M., et al., "A Fluorescent Reporter Assay of Differential Gene Expression Response to Insulin in Hepatocytes," Methods in Cell Physiology, American Journal of Physiology Cell Physiology, May 15, 2019, vol. 317, pp. C143-C151.
Miller A.J., et al., "Generation of Lung Organoids from Human Pluripotent Stem Cells in Vitro," Nature Protocols, Feb. 28, 2019, vol. 14, No. 2, pp. 518-540.
Mitaka T., "Reconstruction of Hepatic Organoid by Hepatic Stem Cells," Journal of Hepatobiliary Pancreatic Surgery, 2002, vol. 9 (6), pp. 697-703.
Montalbano G., et al., "Synthesis of Bioinspired Collagen/Alginate/Fibrin Based Hydrogels for Soft Tissue Engineering," Material Science & Engineering, C 91,2018, pp. 236-246.
Neuschwander-Tetri B.A., et al., "Farnesoid X Nuclear Receptor Ligand Obeticholic Acid for Non-Cirrhotic, Non-Alcoholic Steatohepatitis (FLINT): A Multicentre, Randomised, Placebo-Controlled Trial," Lancet 2015, Mar. 14, 2015, vol. 385, pp. 956-965.
Ng S., et al., "Human iPSC-Derived Hepatocyte-Like Cells Support Plasmodium Liver-Stage Infection In Vitro," Stem cell reports, Mar. 10, 2015, vol. 4, pp. 348-359.
Nissim S., et al., "Iterative Use of Nuclear Receptor Nr5a2 Regulates Multiple Stages of Liver and Pancreas Development," Development Biology, Jul. 26, 2016, vol. 418(1), pp. 108-123.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Perdiguero E.G., et al., "Development and Maintenance of Resident Macrophages," Nature Immunology, Jan. 2016, vol. 17 (1), pp. 2-8.
Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.
Rankin S.A., et al., "A Retinoic Acid-Hedgehog Cascade Coordinates Mesoderm-Inducing Signals and Endoderm Competence During Lung Specification," Cell Reports, Jun. 28, 2016, vol. 16 (1), pp. 66-78.
San Roman A.K., et al., "Boundaries, Junctions and Transitions in the Gastrointestinal Tract," Exp Cell Res, Nov. 15, 2011, vol. 317 (19), pp. 2711-2718.
Shaw T.N., et al., "Tissue-Resident Macrophages in the Intestine are Long Lived and Defined by Tim-4 and CD4 Expression," Journal of Experimental Medicine, 2018, vol. 215 (6), pp. 1507-1518.
Sheng J., et al., "Most Tissue-Resident Macrophages Except Microglia Are Derived from Fetal Hematopoietic Stem Cells," Immunity, Aug. 18, 2015, vol. 43 (2), pp. 382-393.
Shih H.P., et al., "A Gene Regulatory Network Cooperatively Controlled by Pdx1 and Sox9 Governs Lineage Allocation of Foregut Progenitor Cells," Cell Reports, Oct. 13, 2015, vol. 13 (2), 326-336.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.
Spence J.R., et al., "Sox17 Regulates Organ Lineage Segregation of Ventral Foregut Progenitor Cells," Dev Cell, Jul. 2009, vol. 17 (1), pp. 62-74.
Sturgeon C.M., et al., "Wnt Signaling Controls the Specification of Definitive and Primitive Hematopoiesis from Human Pluripotent Stem Cells," Natural Biotechnology, Jun. 2014, vol. 32 (6), pp. 554-561.
Sumazaki R., et al., "Conversion of Biliary System to Pancreatic Tissue in Hes1-Deficient Mice," Nature Genetics, Jan. 2004, vol. 36 (1), pp. 83-87.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.
Tepass U., et al., "Epithelium Formation in the *Drosophila* Midgut Depends on the Interaction of Endoderm and Mesoderm," Development, 1994, vol. 120 (3), pp. 579-590.
Thamm K., et al., "Notch Signaling During Larval and Juvenile Development in the Polychaete Annelid *Capitella* sp. I," Developmental Biology, 2008, vol. 320 (1), pp. 304-318.
Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Zhang X., et al., "A Comprehensive Structure-Function Study of Neurogenin3 Disease-Causing Alleles during Human Pancreas and Intestinal Organoid Development," Developmental Cell, Aug. 5, 2019, vol. 50, pp. 367-380.
Zhang Y., et al., "Development and Stem Cells of the Esophagus," Seminars in Cell & Developmental Biology, Dec. 19, 2016, vol. 66, pp. 25-35.
Zhang Z., et al., "Syndecan4 Coordinates Wnt/JNK and BMP Signaling to Regulate Foregut Progenitor Development," Developmental Biology, 2016, vol. 416 (1), pp. 187-199.
Abe T., et al., "Reporter Mouse Lines for Fluorescence Imaging," Development, Growth & Differentiation, May 2013, vol. 55, No. 4, pp. 390-405.
Adam M., et al., "Psychrophilic Proteases Dramatically Reduce Single-Cell RNA-Seq Artifacts: a Molecular Atlas of Kidney Development," Development, Oct. 1, 2017, vol. 144, No. 19, pp. 3625-3632.
Arora R., et al., "Multiple Roles and Interactions of Tbx4 and Tbx5 in Development of the Respiratory System," PLoS Genetics, Aug. 2, 2012, vol. 8, No. 8, e1002866, 14 pages.
Asahina K., et al., "Septum Transversum-Derived Mesothelium gives rise to Hepatic Stellate Cells and Perivascular Mesenchymal Cells in Developing Mouse Liver," Hepatology, Mar. 2011, vol. 53, No. 3, pp. 983-995.
Barnes R.M., et al., "Analysis of the Handl Cell Lineage Reveals Novel Contributions to Cardiovascular, Neural Crest, Extra- Embryonic, and Lateral Mesoderm Derivatives," Developmental Dynamics, vol. 239, 2010, pp. 3086-3097.
Baron M., et al., "A Single-Cell Transcriptomic Map of the Human and Mouse Pancreas Reveals Inter- and Intra-cell Population Structure," Cell Systems, Oct. 26, 2016, vol. 3, No. 4, pp. 346-360.
Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.
Brandenberg N., et al., "High-Throughput Automated Organoid Culture via Stem-Cell Aggregation in Microcavity Arrays," Nature Biomedical Engineering, 2020, vol. 4, pp. 863-874.
Briggs J.A., et al., "The Dynamics of Gene Expression in Vertebrate Embryogenesis at Single-Cell Resolution," Science, Jun. 1, 2018, vol. 360, No. 6392, eaar5780, 23 pages.
Bult C.J., et al., "Mouse Genome Database (MGD) 2019,"Nucleic Acids Research, Jan. 8, 2019, vol. 47, No. D1, pp. D801-D806.
Calder, L.E., "Retinoic Acid-mediated Regulation of GLI3 Enables High Yield Motoneuron Derivation from Human Embryonic Stem Cells Independent of Extrinsic Activation of SHH Signaling," Dissertation, Jan. 2015, 24 pages.
Cao J., et al., "The Single-Cell Transcriptional Landscape of Mammalian Organogenesis," Nature, Feb. 2019, vol. 566, No. 7745, pp. 496-502.
Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.

(56) References Cited

OTHER PUBLICATIONS

Carpenedo R.L., et al., "Rotary Suspension Culture Enhances the Efficiency, Yield, and Homogeneity of Embryoid Body Differentiation," Stem Cells, 2007, vol. 25, pp. 2224-2234.
Carpenedo R.L., "Microsphere-Mediated Control of Embryoid Body Microenvironments," May 2010, 24 pages.
Chambers M. S., et al., "Highly Efficient Neural Conversion of Human ES and IPS Cells by Dual Inhibition of SMAD Signaling," Nature Biotechnol., Mar. 2009, vol. 27(3), pp. 275-280.
Chua C.C., et al., "Single Luminal Epithelial Progenitors Can Generate Prostate Organoids in Culture," Nature Cell Biology, Oct. 2014, vol. 16(10), 26 pages.
Cohen M., et al., "Lung Single-Cell Signaling Interaction Map Reveals Basophil Role in Macrophage Imprinting," Cell, Nov. 1, 2018, vol. 175, No. 4, pp. 1031-1044.
Conley B.J., et al., "Derivation, Propagation and Differentiation of Human Embryonic Stem Cells," The International Journal of Biochemistry & Cell Biology, 2004, vol. 36, pp. 555-567.
De Soysa T.Y., et al., "Single-cell Analysis of Cardiogenesis Reveals Basis for Organ-level Developmental Defects," Nature, Aug. 2019, vol. 572, No. 7767, pp. 120-124.
El Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.
Erkan M., et al., "Organ-, Inflammation- and Cancer Specific Transcriptional Fingerprints of Pancreatic and Hepatic Stellate Cells,". Molecular Cancer, Dec. 2010, vol. 9, No. 1, pp. 1-15.
Farrell J.A., et al., "Single-Cell Reconstruction of Developmental Trajectories During Zebrafish Embryogenesis," Science, Jun. 1, 2018, vol. 360, No. 6392, eaar3131, 18 pages.
Fattahi F., et al., "Deriving Human ENS Lineages for Cell Therapy and Drug Discovery in Hirschsprung Disease," Nature, Feb. 2016, vol. 531 (7592), pp. 105-109.
Ferretti E., et al., "Mesoderm Specification and Diversification: From Single Cells to Emergent Tissues,". Current Opinion in Cell Biology, Dec. 2019, vol. 61, pp. 110-116.
Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.
Francou A., et al., "Second Heart Field Cardiac Progenitor Cells in the Early Mouse Embryo," Biochimica et Biophysica Acta, Apr. 1, 2013, vol. 1833, No. 4, pp. 795-798.
Franklin V., et al., "Regionalisation of the Endoderm Progenitors and Morphogenesis of the Gut Portals of the Mouse Embryo,". Mechanisms of Development, Jul. 1, 2008, vol. 125, No. 7, pp. 587-600.
Grand R. J., et al., "Development of the Human Gastrointestinal Tract- A Review," Gastroenterology, May 1976, vol. 70, No. 5, pp. 790-810.
Grapin-Botton A., "Antero-posterior Patterning of the Vertebrate Digestive Tract: 40 Years After Nicole Le Douarin's PhD Thesis," The International Journal of Developmental Biology, Jan. 1, 2005, vol. 49, Nos. 2-3, pp. 335-347.
Griffin O.D., et al., "Human B1 Cells in Umbilical Cord and Adult Peripheral Blood Express the Novel Phenotype CD20+CD27+CD43+CD70-," Journal of Experimental Medicine, 2011, vol. 208(1), pp. 67-80.
Hoffmann A.D., et al., "Sonic Hedgehog Is required in Pulmonary Endoderm for Atrial Septation," Development, 2009, vol. 136, pp. 1761 1770.
Horie M., et al., "TBX4 is involved in the Super-Enhancer-Driven Transcriptional Programs Underlying Features Specific to Lung Fibroblasts,". The American Journal of Physiology-Lung Cellular and Molecular Physiology, Jan. 1, 2018, vol. 314, No. 1, pp. L177-L191.
Huynh N., et al., "61.06 Feasibility and Scalability of Spring Parameters in Distraction Enterogenesis in a Murine Model," 2017, 3 pages, Retrieved from Internet: URL: https://www.asc-abstracts.org/abs2017/61-06-feasibility-and-scalability-of-spring-parameters-in-distraction-enterogenesis-in-a-murine-model/, Retrieved on Jun. 4, 2022.
Ibarra-Soria X. et al., "Defining Murine Organogenesis at Single-Cell Resolution Reveals a Role for the Leukotriene Pathway in Regulating Blood Progenitor Formation,". Nature Cell Biology, Feb. 2018, vol. 20, No. 2, pp. 127-134.
Khan J.A., et al., "Fetal Liver Hematopoietic Stem Cell Niches Associate With Portal Vessels," Science, Jan. 8, 2016, vol. 351 (6269), pp. 176-180.
Kharchenko V. P., et al., "Bayesian Approach to Single-cell Differential Expression Analysis," Nature Methods, Jul. 2014, vol. 11, No. 7, pp. 740-742.
Kim E., et al., "Isl1 Regulation of Nkx2.1 in the Early Foregut Epithelium Is Required for Trachea-Esophageal Separation and Lung Lobation," Developmental Cell, Dec. 16, 2019, vol. 51, No. 6, pp. 675-683.
Kiselev Y. V., et al., "SCmap—A Tool for Unsupervised Projection of Single Cell RNA-seq data," Nature Methods, May 2018, vol. 15 (5), pp. 359-362.
Koike H., et al., "Engineering Human Hepato-Biliary-Pancreatic Organoids from Pluripotent Stem Cells," Nature Protocols, Feb. 2021, vol. 16(2), pp. 919-936.
Koike H., et al., "Modeling human hepato-biliary-pancreatic organogenesis from the foregutmidgut boundary," Nature, Oct. 2019, vol. 574(7776), pp. 112-116.
Langfelder P., et al., "WGCNA: An R package for weighted correlation network analysis," BMC Bioinformatics, Dec. 2008, vol. 9 (1), pp. 1-13.
Langmead B., et al., "Fast Gapped-read Alignment with Bowtie 2," Nature Methods, Apr. 2012, vol. 9(4), pp. 357-359.
Le Douarin N., et al., "Role of the Mesoderm in the Induction of the Synthesis of Glycogen During Differentiation of the Hepatic Endoderm," CR Acad Hebd Seances Acad Sci D, 1967, vol. 264, pp. 1872-1874.
Li et al., "RSEM: Accurate Transcript Quantification from RNA-Seq data with or without a Reference Genome", BMC Bioinformatics Aug. 2011, vol. 12, No. 323, 16 pages.
Li L.C., et al., "Single-Cell Transcriptomic Analyses Reveal Distinct Dorsal/Ventral Pancreatic Programs,". EMBO Reports, Oct. 2018, vol. 19, No. 10, e46148, 14 pages.
Lis R., et al., "Conversion of Adult Endothelium to Immunocompetent Haematopoietic Stem Cells," Nature, May 2017, vol. 545 (7655), pp. 439-445.
Loh K. M., et al., "Mapping the Pairwise Choices Leading from Pluripotency to Human Bone, Heart, and Other Mesoderm Cell Types," Cell, Jul. 14, 2016, vol. 166, No. 2, pp. 451-467.
Manno L. G., et al., "Molecular Diversity of Midbrain Development in Mouse, Human and Stem Cells," Cell, Oct. 6, 2016, vol. 167, (2), pp. 566-580.
Mashima H., et al., "INSL5 may be a Unique Marker of Colorectal Endocrine Cells and Neuroendocrine Tumors," Biochemical and Biophysical Research Communications, 2013, vol. 432, pp. 586-592.
McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.
Menendez L., et al., "Directed differentiation of human pluripotent cells to neural crest stem cells", Nature Protocols, Jan. 2013, vol. 8 (1), pp. 203-212.
Moignard V., et al., "Decoding the Regulatory Network of Early Blood Development From Single-Cell Gene Expression Measurements," Nature Biotechnology, Mar. 2015, vol. 33, No. 3, pp. 269-276.
Montecino-Rodriguez E., et al., "Identification of a B-1 B Cell-Specified Progenitor," Natural Immunology, Mar. 2006, vol. 7(3), pp. 293-301.
Morrison A. J., et al., "Single-cell transcriptome analysis of avian neural crest migration reveals signatures of invasion and molecular transitions," eLife., Dec. 2017, vol. 6, 27 pages.

(56) References Cited

OTHER PUBLICATIONS

Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.
Nasr T., et al., "Endosome-Mediated Epithelial Remodeling Downstream of Hedgehog-Gli Is Required for Tracheoesophageal Separation," Developmental Cell, Dec. 16, 2019, vol. 51, No. 6, pp. 665-674.
Naujok O., et al., "Cytotoxicity and Activation of the WNT/Beta-Catenin Pathway in Mouse Embryonic Stem Cells Treated with Four GSK3 Inhibitors," BMC Research Notes, 2014, vol. 7, No. 273, pp. 1-8.
Nowotschin S., et al., "The Emergent Landscape of the Mouse Gut Endoderm at Single-Cell Resolution," Nature, May 2019, vol. 569, No. 7756, pp. 361-367.
Pedersen J.K., et al., "Endodermal Expression of Nkx6 Genes depends differentially on Pdx1," Developmental Biology, Dec. 15, 2005, vol. 288, No. 2, pp. 487-501.
Peng T., et al., "Coordination of Heart and Lung Co-development by a Multipotent Cardiopulmonary Progenitor," Nature, Aug. 2013, vol. 500, No. 7464, pp. 589-592.
Pijuan-Sala B., et al., "A Single-Cell Molecular Map of Mouse Gastrulation and Early Organogenesis," Nature, Feb. 2019, vol. 566, No. 7745, pp. 490-495.
Que J., et al., "Mesothelium Contributes to Vascular Smooth Muscle and Mesenchyme During Lung Development," Proceedings of the National Academy of Sciences USA, Oct. 28, 2008, vol. 105, No. 43, pp. 16626-16630.
Rana M.S., et al., "A Molecular and Genetic Outline of Cardiac Morphogenesis," Acta Physiologica (Oxf), Apr. 2013, vol. 207, No. 4, pp. 588-615.
Riehl T., et al., "CD44 and TLR4 Mediate Hyaluronic Acid Regulation of Lgr5+ Stem Cell Proliferation, Crypt Fission, and Intestinal Growth in Postnatal and Adult Mice," The American Journal of Physiology-Gastrointestinal and Liver Physiology, Dec. 1, 2015, vol. 309, No. 11, pp. G874-G887.
Robert-Moreno A., et al., "Impaired Embryonic Haematopoiesis Yet Normal Arterial Development in the Absence of the Notch ligand Jagged1," EMBO Journal, 2008, vol. 27(13), pp. 1886-1895.
Robert-Moreno A., et al., "RBPjK-dependent Notch Function Regulates Gata2 and is Essential for the Formation of Intra-embryonic Hematopoietic Cells," Development and disease, 2005, vol. 132(5), pp. 1117-1126.
Rothstein L.T., et al., "Human B-1 cells take the stage," Annals of the New York Academy of Sciences, May 2013, vol. 1285, pp. 97-114.
Rubin L.L., et al., "Targeting the Hedgehog Pathway in Cancer," Nature Reviews Drug Discovery, 2006, vol. 5, pp. 1026-1033.
Sander M., et al., "Homeobox Gene Nkx6.1 lies Downstream of Nkx2.2 in the major Pathway of Beta-Cell formation in the Pancreas," Development, Dec. 15, 2000, vol. 127, No. 24, pp. 5533-5540.
Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.
Sauka-Spengler T. et al., "Snapshot: Neural Crest," Cell, Oct. 2010, vol. 143, No. 3, 486-486.e1.
Scialdone A., et al., "Resolving Early Mesoderm Diversification Through Single-Cell Expression Profiling," Nature, Jul. 2016, vol. 535, No. 7611, pp. 289-293.
Scott A., et al., "Repeated Mechanical Lengthening of Intestinal Segments in a Novel Model," Journal of Pediatric Surgery, Jun. 2015, vol. 50, No. 6, pp. 954-957.
Semrau S., et al., "Dynamics of lineage commitment revealed by single-cell transcriptomics of differentiating embryonic stem cells", Nature Communications, Oct. 2017, vol. 8 (1), pp. 1-16.
Simões F.C., et al., "The Ontogeny, Activation and Function of the Epicardium During Heart Development and Regeneration," Development, Apr. 1, 2018, vol. 145, No. 7, dev155994; 13 pages.
Soldatow V. Y., et al., "In Vitro Models for Liver Toxicity Testing," Toxicology Research 2.1, 2013, vol. 2, pp. 23-39.
Sugimura R., et al., "Haemotopoietic Stem and Progenitor Cells from Human Pluripotent Stem Cells," Nature, May 25, 2017, vol. 545 (7655), pp. 432-438.
Sullins V. F., et al., "Intestinal Lengthening in an Innovative Rodent Surgical Model," Journal of Pediatric Surgery, Dec. 2014, vol. 49, No. 12, pp. 1791-1794.
Sweetman D., et al., "The Migration of Paraxial and Lateral Plate Mesoderm Cells Emerging from the Late Primitive Streak Is Controlled by Different Wnt Signals," BMC Developmental Biology, Dec. 2008, vol. 8, No. 1, pp. 1-15.
Tanaka M., "Molecular and Evolutionary Basis of Limb Field Specification and Limb Initiation," Development, Growth & Differentiation, Jan. 2013, vol. 55, No. 1, pp. 149-163.
Tang X. et al. "Transcriptome Regulation and Chromatin Occupancy by E2F3 and MYC in Mice," Scientific Data, Feb. 16, 2016, vol. 3, No. 1, pp. 1-8.
Testaz S., et al., "Sonic hedgehog restricts adhesion and migration of neural crest cells independently of the Patched-Smoothened-Gli signaling pathway," PNAS, Oct. 23, 2001, vol. 98 (22), pp. 12521-12526.
Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.
Uenishi I.G., et al., "NOTCH Signaling Specifies Arterial-type Definitive Hemogenic Endothelium from Human Pluripotent Stem Cells," Nature Communication, 2018, 14 pages.
Wagner D.E., et al., "Lineage Tracing Meets Single-cell Omics: Opportunities and Challenges," Nature Reviews Genetics, Jul. 2020, vol. 21, No. 7, pp. 410-427.
Wang J., et al., "WebGestalt 2017: A more comprehensive, powerful, flexible and interactive gene set enrichment analysis toolkit," Nucleic Acids Research, Jul. 2017, vol. 45, 8 pages.
Wang L., et al., "The Maintenance and Generation of Membrane Polarity in Hepatocytes," Hepatology, 2004, vol. 39, No. 4, pp. 892-899.
Weinreb C., et al., "Lineage tracing on transcriptional landscapes links state to fate during differentiation," Science, Feb. 14, 2020, vol. 367, ( 6479), 48 pages.
Weinreb C., et al., "Spring: A Kinetic Interface for Visualizing High Dimensional Single-cell Expression Data," Bioinformatics, Apr. 2018, vol. 34 ( 7), pp. 1246-1248.
Wilkinson C. A., et al., "Long-term Ex-vivo Haematopoietic-stem-Cell Expansion Allows Nonconditioned Transplantation," Nature, 2019, vol. 571(7763), pp. 117-121.
Xie T., et al., "Single-Cell Deconvolution of Fibroblast Heterogeneity in Mouse Pulmonary Fibrosis," Cell Reports, Mar. 27, 2018, vol. 22, No. 13, pp. 3625-3640.
Yao S., et al., "Long-Term Self-Renewal and Directed Differentiation of Human Embryonic Stem Cells in Chemically Defined Conditions," PNAS, 2006, vol. 103, No. 18, pp. 6907-6912.
Yu G., et al., "ClusterProfiler: An R package for Comparing Biological Themes Among Gene Clusters," OMICS: A Journal Integrative Biology, May 2012, vol. 16 (5), pp. 284-287.
Zaret K.S., "From Endoderm to Liver Bud: Paradigms of Cell Type Specification and Tissue Morphogenesis," Current Topics in Developmental Biology, Jan. 2016, vol. 117, pp. 647-669.
Zeltner N., et al., "Feeder-free derivation of neural crest progenitor cells from human pluripotent stem cells," Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.

* cited by examiner b.

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: AP2alpha Sense Primer -continued

<400> SEQUENCE: 1
atgctttgga aattgacgga                                              20

<210> SEQ ID NO 2
<211> LENGTH: 20
<212> TYPE: DNA
<213> ORGANISM: Artificial Sequence
<220> FEATURE:
<223> OTHER INFORMATION: AP2alpha Anti-Sense Primer

<400> SEQUENCE: 2
attgacctac agtgcccagc                                              20

<210> SEQ ID NO 3
<211> LENGTH: 20
<212> TYPE: DNA
<213> ORGANISM: Artificial Sequence
<220> FEATURE:
<223> OTHER INFORMATION: Edn3 Sense Primer

<400> SEQUENCE: 3
gcacgtgctt cacctacaag                                              20

<210> SEQ ID NO 4
<211> LENGTH: 19
<212> TYPE: DNA
<213> ORGANISM: Artificial Sequence
<220> FEATURE:
<223> OTHER INFORMATION: Edn3 Anti-Sense Primer

<400> SEQUENCE: 4
ggacagtcca tagggcacc                                               19

<210> SEQ ID NO 5
<211> LENGTH: 21
<212> TYPE: DNA
<213> ORGANISM: Artificial Sequence
<220> FEATURE:
<223> OTHER INFORMATION: GAPDH Sense Primer

<400> SEQUENCE: 5
cccatcacca tcttccagga g                                            21

<210> SEQ ID NO 6
<211> LENGTH: 22
<212> TYPE: DNA
<213> ORGANISM: Artificial Sequence
<220> FEATURE:
<223> OTHER INFORMATION: GAPDH Anti-Sense Primer

<400> SEQUENCE: 6
cttctccatg gtggtgaaga cg                                           22

<210> SEQ ID NO 7
<211> LENGTH: 21
<212> TYPE: DNA
<213> ORGANISM: Artificial Sequence
<220> FEATURE:
<223> OTHER INFORMATION: GDNF Sense Primer

<400> SEQUENCE: 7
tccatgacat catcgaactg a                                            21

```
<210> SEQ ID NO 8
<211> LENGTH: 18
<212> TYPE: DNA
<213> ORGANISM: Artificial Sequence
<220> FEATURE:
<223> OTHER INFORMATION: GDNF Anti-Sense Primer

<400> SEQUENCE: 8
gtctgcctgg tgctgctc                                                 18

<210> SEQ ID NO 9
<211> LENGTH: 20
<212> TYPE: DNA
<213> ORGANISM: Artificial Sequence
<220> FEATURE:
<223> OTHER INFORMATION: HoxA2 Sense Primer

<400> SEQUENCE: 9
ccaagaaaac cgcacttctg                                               20

<210> SEQ ID NO 10
<211> LENGTH: 17
<212> TYPE: DNA
<213> ORGANISM: Artificial Sequence
<220> FEATURE:
<223> OTHER INFORMATION: HoxA2 Anti-Sense Primer

<400> SEQUENCE: 10
catcggcgat ttccagg                                                  17

<210> SEQ ID NO 11
<211> LENGTH: 19
<212> TYPE: DNA
<213> ORGANISM: Artificial Sequence
<220> FEATURE:
<223> OTHER INFORMATION: HoxB3 Sense Primer

<400> SEQUENCE: 11
cgtcatgaat gggatctgc                                                19

<210> SEQ ID NO 12
<211> LENGTH: 20
<212> TYPE: DNA
<213> ORGANISM: Artificial Sequence
<220> FEATURE:
<223> OTHER INFORMATION: HoxB3 Anti-Sense Primer

<400> SEQUENCE: 12
atattcacat cgagccccag                                               20

<210> SEQ ID NO 13
<211> LENGTH: 20
<212> TYPE: DNA
<213> ORGANISM: Artificial Sequence
<220> FEATURE:
<223> OTHER INFORMATION: HoxB5 Sense Primer

<400> SEQUENCE: 13
ggaagcttca catcagccat                                               20

<210> SEQ ID NO 14
<211> LENGTH: 20
<212> TYPE: DNA
<213> ORGANISM: Artificial Sequence
<220> FEATURE:
<223> OTHER INFORMATION: HoxB5 Anti-Sense Primer
```

```
<400> SEQUENCE: 14
ggaactcctt ttccagctcc                                               20

<210> SEQ ID NO 15
<211> LENGTH: 20
<212> TYPE: DNA
<213> ORGANISM: Artificial Sequence
<220> FEATURE:
<223> OTHER INFORMATION: HoxB7 Sense Primer

<400> SEQUENCE: 15
aacttccgga tctacccctg                                               20

<210> SEQ ID NO 16
<211> LENGTH: 20
<212> TYPE: DNA
<213> ORGANISM: Artificial Sequence
<220> FEATURE:
<223> OTHER INFORMATION: HoxB7 Anti-Sense Primer

<400> SEQUENCE: 16
ctttctccag ctccagggtc                                               20

<210> SEQ ID NO 17
<211> LENGTH: 20
<212> TYPE: DNA
<213> ORGANISM: Artificial Sequence
<220> FEATURE:
<223> OTHER INFORMATION: Pax3 Sense Primer

<400> SEQUENCE: 17
gccgcatcct gagaagtaaa                                               20

<210> SEQ ID NO 18
<211> LENGTH: 20
<212> TYPE: DNA
<213> ORGANISM: Artificial Sequence
<220> FEATURE:
<223> OTHER INFORMATION: Pax3 Anti-Sense Primer

<400> SEQUENCE: 18
cttcatctga ttggggtgct                                               20

<210> SEQ ID NO 19
<211> LENGTH: 18
<212> TYPE: DNA
<213> ORGANISM: Artificial Sequence
<220> FEATURE:
<223> OTHER INFORMATION: Pax7 Sense Primer

<400> SEQUENCE: 19
caaacacagc atcgacgg                                                 18

<210> SEQ ID NO 20
<211> LENGTH: 20
<212> TYPE: DNA
<213> ORGANISM: Artificial Sequence
<220> FEATURE:
<223> OTHER INFORMATION: Pax7 Anti-Sense Primer

<400> SEQUENCE: 20
cttcagtggg aggtcaggtt                                               20
```

-continued

```
<210> SEQ ID NO 21
<211> LENGTH: 20
<212> TYPE: DNA
<213> ORGANISM: Artificial Sequence
<220> FEATURE:
<223> OTHER INFORMATION: Snail2 Sense Primer

<400> SEQUENCE: 21
tgacctgtct gcaaatgctc                                                    20

<210> SEQ ID NO 22
<211> LENGTH: 19
<212> TYPE: DNA
<213> ORGANISM: Artificial Sequence
<220> FEATURE:
<223> OTHER INFORMATION: Snail2 Anti-Sense Primer

<400> SEQUENCE: 22
cagaccctgg ttgcttcaa                                                     19

<210> SEQ ID NO 23
<211> LENGTH: 18
<212> TYPE: DNA
<213> ORGANISM: Artificial Sequence
<220> FEATURE:
<223> OTHER INFORMATION: Sox10 Sense Primer

<400> SEQUENCE: 23
agctcagcaa gacgctgg                                                      18

<210> SEQ ID NO 24
<211> LENGTH: 20
<212> TYPE: DNA
<213> ORGANISM: Artificial Sequence
<220> FEATURE:
<223> OTHER INFORMATION: Sox10 Anti-Sense Primer

<400> SEQUENCE: 24
ctttcttgtg ctgcatacgg                                                    20

<210> SEQ ID NO 25
<211> LENGTH: 20
<212> TYPE: DNA
<213> ORGANISM: Artificial Sequence
<220> FEATURE:
<223> OTHER INFORMATION: Sox9 Sense Primer

<400> SEQUENCE: 25
gtaatccggg tggtccttct                                                    20

<210> SEQ ID NO 26
<211> LENGTH: 19
<212> TYPE: DNA
<213> ORGANISM: Artificial Sequence
<220> FEATURE:
<223> OTHER INFORMATION: Sox9 Anti-Sense Primer

<400> SEQUENCE: 26
gtacccgcac ttgcacaac                                                     19

<210> SEQ ID NO 27
<211> LENGTH: 20
<212> TYPE: DNA
<213> ORGANISM: Artificial Sequence
<220> FEATURE:
<223> OTHER INFORMATION: Zic1 Sense Primer
```

```
<400> SEQUENCE: 27
aagatccaca aaaggacgca                                          20

<210> SEQ ID NO 28
<211> LENGTH: 19
<212> TYPE: DNA
<213> ORGANISM: Artificial Sequence
<220> FEATURE:
<223> OTHER INFORMATION: Zic1 Anti-Sense Primer

<400> SEQUENCE: 28
cacgtgcatg tgcttcttg                                           19
```

METHOD OF MAKING IN VIVO HUMAN SMALL INTESTINE ORGANOIDS FROM PLURIPOTENT STEM CELLS

PRIORITY

This application claims priority to and benefit of U.S. Provisional Application Ser. No. 62/065,131 titled "In vivo Model of Human Small Intestine Using Pluripotent Stem Cells," filed Oct. 17, 2014.

GOVERNMENT SUPPORT CLAUSE

This invention was made with government support under DK083325, DK098350, NS080815, and DK092456. The government has certain rights in the invention.

BACKGROUND OF THE INVENTION

Because of the complexity of a vascularized, hollow organ such as the intestine, the development of an adequate human model for its study and replacement following surgery or pathological processes has proven to be a seemingly impossible task. Methods for studying the human intestine have largely required in vitro culture systems or have relied on animal models to address numerous translational questions, which do not always translate well in human studies. Traditional intestinal epithelial primary culture techniques were mostly limited to tissue culture technologies, such as organ cultures or intestinal cell lines that do not recapitulate the hierarch of stem cells to differentiated cells. While the recent identification of intestinal stem cells and conditions appropriate for human epithelial culture has overcome many of these obstacles, successful in vivo engraftment of epithelia cultures remains challenging because of the need for a supporting mesenchyme as exists in models exposing host mesenchyme following mucosal injury.

Differentiation of human pluripotent stem cells (hPSCs) into orga-specific subtypes offers an exciting avenue for the study of embryonic development and disease processes, for pharmacologic studies and as a potential resource for therapeutic transplant. To date, limited in vivo models exist for human intestine, all of which are dependent upon primary epithelial cultures or digested tissue from surgical biopsies that include mesenchymal cells transplanted on biodegradable scaffolds.

There is presently a need in the art for methods of making vascularized, hollow organs such as the intestine, in particular a model for the study of enteric nervous system (ENS) intestinal biology. Further, there is a need in the art for methods of making intestinal tissues having a functional enteric nervous system. Currently, methods for studying the human intestine have largely required in vitro culture systems or have relied on animal models. These studies, however, do not always translate well into human studies. While intestinal stem cells and human epithelial culture has addressed some of these problems, successful in vivo engraftment of epithelial cultures remains challenging because of the need for a supporting mesenchyme.

BRIEF SUMMARY OF THE INVENTION

Disclosed are methods for making a vascularized hollow organ derived from human intestinal organoid (HIOs). The HIOs may be obtained from human embryonic stem cells (ESC's) and/or induced pluripotent stem cells (iPSCs), such that the HIO forms mature intestinal tissue. Also disclosed are methods for making a human intestinal tissue containing a functional enteric nervous system (ENS).

BRIEF DESCRIPTION OF THE DRAWINGS

FIG. 1A—Schematic representing development of HIOs from hPSCs and transplantation under kidney capsule to produce mature human intestinal tissue. FIG. 1B—Two HIOs in vitro at 35 d consisting of intestinal epithelium (black arrowheads) surrounded by supporting mesenchyme (white arrowheads). Scale bar, 100 µm. FIG. 1C—Engraftment (outlined) after 6 weeks with complex structure and established peripheral capillary network. The mouse kidney is seen below the engraftment for size comparison. Scale bar, 5 mm. FIG. 1D—Cross-section of engraftment at 6 weeks revealing intestinal structure with central lumen. Scale bar, 5 mm. FIG. 1E—Magnified luminal surface of engraftment displaying sheet of villi each with its own central capillary. Scale bar, 500 µm. n=139 transplants.

FIG. 2A—Low- and high-power imaging following H&E staining of engrafted HIO. Low magnification imaging demonstrates multiple areas of epithelium, laminated layers of smooth muscle and peripheral capillaries. Scale bars, 500 µm. High magnification imaging demonstrates crypt-villus domains as well as appropriate layers of subepithelium including lamina propria, muscularis mucosa, submucosa and outer smooth muscle layers. FIG. 2B—Alcian blue-periodic acid-Schiff staining of epithelium within engraftment revealing secretory lineages within the crypt-villus axis. Black arrowhead points to PAS-labeled Paneth cells present within crypt bases. FIG. 2C—All four intestinal lineages were present in engraftments including enterocytes (VIL), goblet cells (MUC2), Paneth cells (LYSO; white arrowhead; scale bars, 50 µm) and enteroendocrine cells (CHGA). E-cadherin (ECAD) was used for additional epithelial staining. FIG. 2D—Tuft cells are also seen throughout the epithelium, as labeled with doublecortin-like kinase 1 (DCLK1). FIG. 2E—mMECA-32 staining of mouse host vasculature ingrowth. FIG. 2F—Edu staining of active proliferation within crypt bases and proliferative zones within crypts of epithelium. FIG. 2G—Staining for VIM reveals the contribution of supporting mesenchyme, including laminated smooth muscle (white arrowheads) with staining of α-SMA. Merged images show dual staining with VIM and α-SMA, revealing a pericryptal sheath of supporting ISEMFs. FIGS. 2H-2I—Contribution of human epithelial cells (FIG. 2H) and human mesenchymal tissue (FIG. 2I), as assessed by HuNuc staining through the full thickness of the engraftment. Dotted line separates engraftment from mouse kidney below. All scale bars are 100 µm except where specified otherwise. n=134 transplants.

(FIGS. 3A-D) Immunostaining of engrafted intestinal tissue (in vivo) revealing maturity of brush-border enzymes including SIM (FIG. 3A), DPPIV (FIG. 3B), LCT (FIG. 3C) and the differentiated enteroendocrine cell subtype (GIP) (FIG. 3D). ECAD and CDX2 were used for additional epithelial staining. (FIGS. 3E-H) Staining of HIOs in vitro at comparable time points to transplants for SIM (FIG. 3E), DPPIV (FIG. 3F), LCT (FIG. 3G) or GIP for comparison (FIG. 3H). FIG. 3I. Relative gene expression of LCT, SIM, DPPIV and GIP in HIOs in vitro as compared to transplanted (Txp) HIOs.

Values in graphs represent mean±s.e.m.; *P<0.05; **P<0.01; t-test. HIOs in vitro: n=4; transplants (Txp): n=8. Scale bars, 100 µm.

Figure 4:
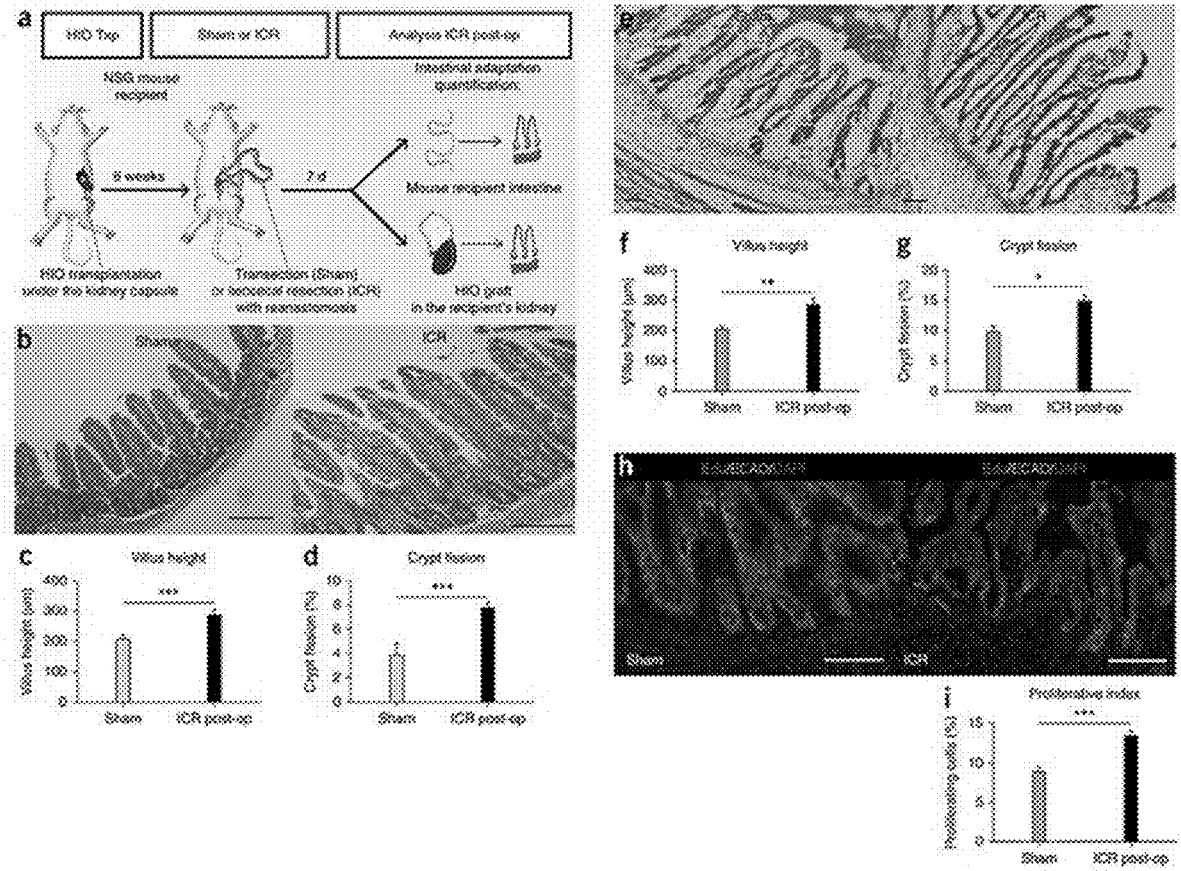

FIGS. 4A-I. Engrafted human intestinal tissue responds to humoral factors following ileocecal resection (ICR) in the mouse host. (a) Schematic representing resection experiments in mice with transplanted HIOs. FIG. 4B. H&E staining of murine epithelium in sham versus ICR groups. Comparison of measured villus height (µm; FIG. 4C) and percentage of crypt fission (FIG. 4D) in mouse intestine between sham and ICR groups. (FIG. 4E) H&E staining of engrafted HIO epithelium in sham versus ICR groups. Comparison of villus height (FIG. 4F) and percentage of crypt fission (FIG. 4G) within engrafted HIOs in sham group versus ICR groups. (FIG. 4H) Immunofluorescence staining using Edu as a marker of intestinal cell proliferation in sham and ICR groups. ECAD is used to stain the epithelium. (FIG. 4I) Comparison of proliferative index (%) between sham and ICR groups in engrafted HIOs where proliferative index=number of Edu+ cells divided by total number of cells within intestinal crypt. Scale bars, 100 µm. Values in graphs represent mean±s.e.m. *P<0.05; P<0.01; *P<0.001; t-test. Sham group: n=4; ICR group: n=8.

Figure 5:
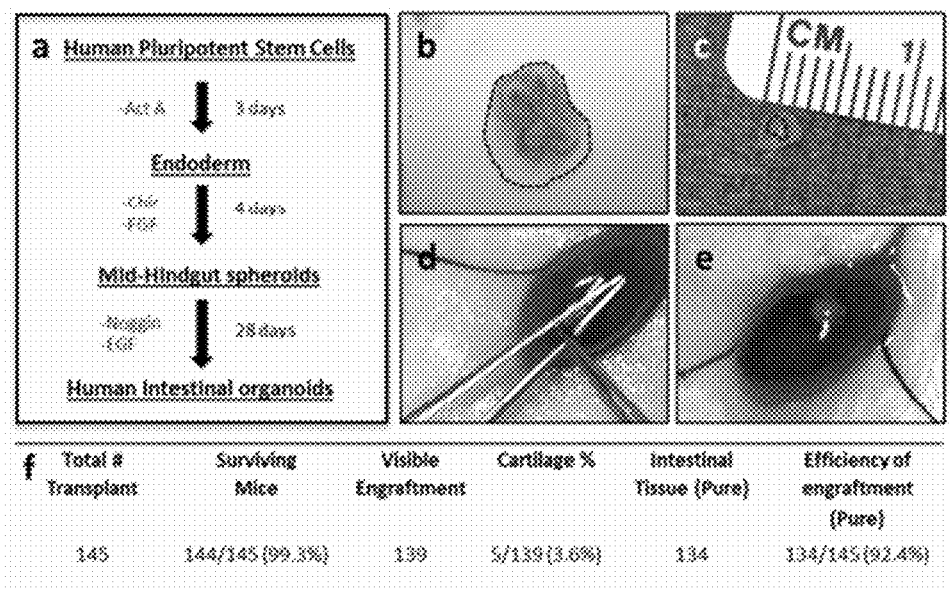

FIGS. 5A-F. Timeline/Schematic of HIO production, Size and Engraftment Efficiency. (a) Schematic representing directed differentiation of HIOs from hPSCs over a period of 35 days. FIG. 5B. Picture of HIO prior to transplant revealing central epithelium and surrounding supporting mesenchyme (outlined). FIG. 5 C. Relative size of one HIO (outlined) embedded in type I collagen prior to transplant. FIG. 5D. Creation of pocket under kidney capsule using fine forceps. FIG. 5E. Picture of transplanted HIO under kidney capsule. FIG. 5F. Table showing efficiency of engraftments at 6 week time point after transplantation.

Figure 6:
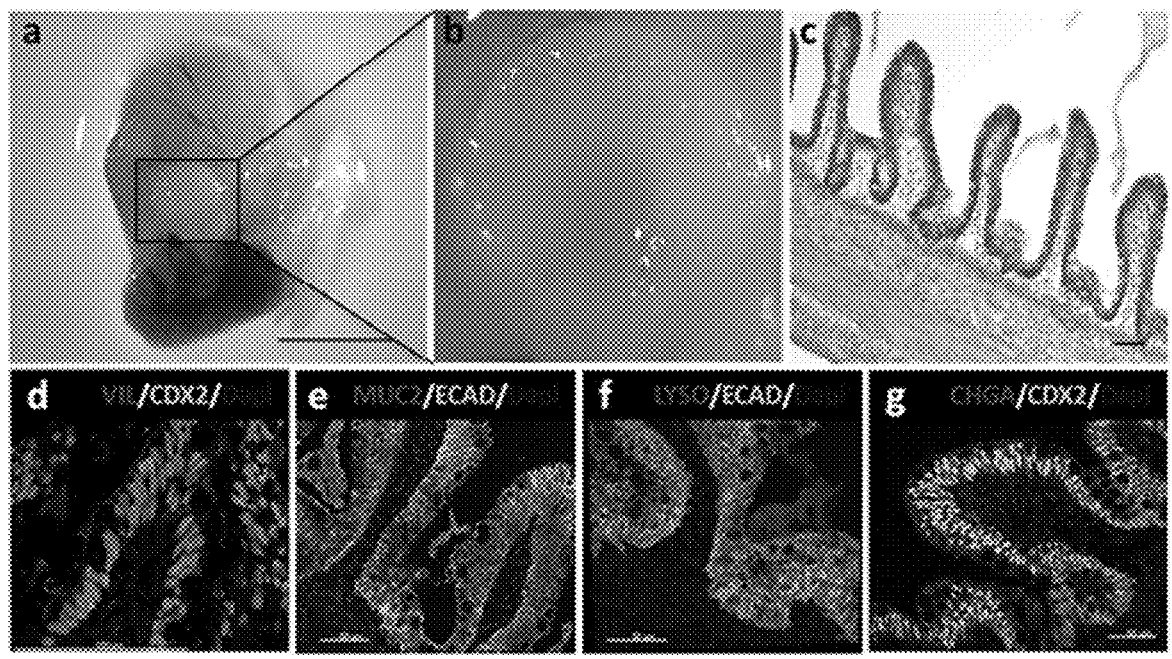

FIG. 6. HIOs from induced pluripotent stem cells engraft to form mature human intestinal tissue in vivo. FIG. 6A. Engraftment 6 weeks after transplant using HIO derived from induced pluripotent stem cells. FIG. 6B. Magnified image of engraftment revealing luminal surface of engraftment with villi and central capillaries. FIG. 6C. Magnified H&E of epithelium within engraftment (Scale bar 100 µm). Crypt-villus domains were present as well as appropriate layers of sub-epithelium including lamina propria, muscularis mucosa, submucosa, and laminated outer smooth muscle layers. (FIGS. 6D-G) All 4 intestinal lineages were present in engraftments including enterocytes (Villin-VIL) (Scale bar 100 µm) (FIG. 6D), Goblet cells (Mucin-MUC2) (FIG. 6E), Paneth cells (Lysozyme-LYSO) (FIG. 6F), and enteroendocrine cells (Chromogranin A-CHGA) (FIG. 6G). E-cadherin (ECAD) or CDX2 were used for additional epithelial staining. (All scale bars 50 um except where specified).

Figure 7:
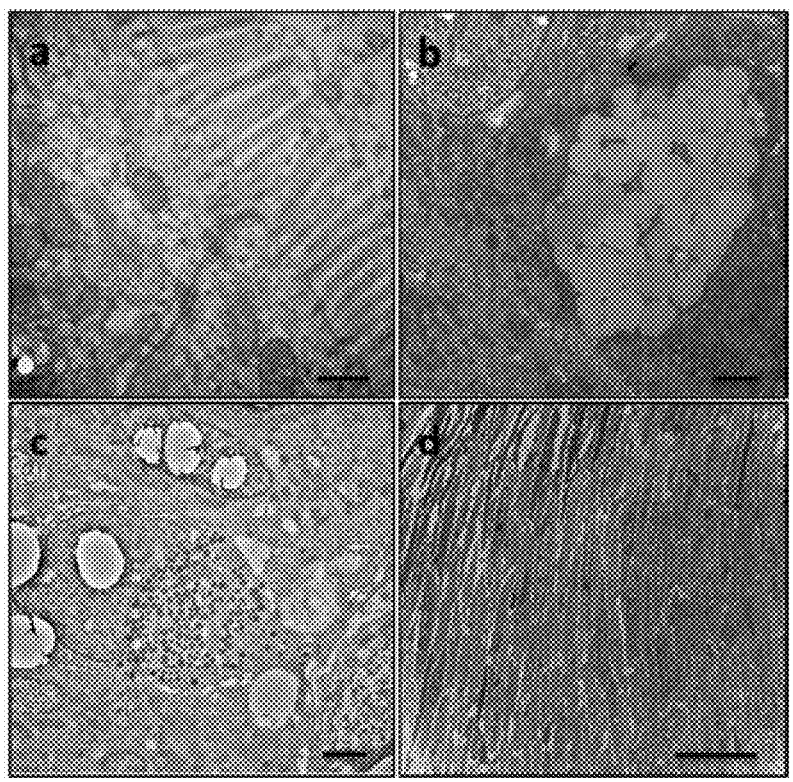

FIG. 7. Transmission Electron Microscopy (TEM) of engrafted tissue at 6 weeks. FIG. 6A. TEM image of brush border microvilli on the surface of intestinal epithelium. Tight and adherens junctions can also be seen in this image near the apical surface (scale bar 500 nm). FIG. 6B. TEM image of goblet cell with secretory granules (white) containing mucin (scale bar 2 µm). FIG. 6C. TEM image of enteroendocrine cell with secretory granules (dark) ready for release on basolateral aspect of cell (scale bar 2 µm). FIG. 6D. TEM image of smooth muscle within engraftment with parallel orientation of smooth muscle fibers (scale bar 10 µm).

Figure 8:
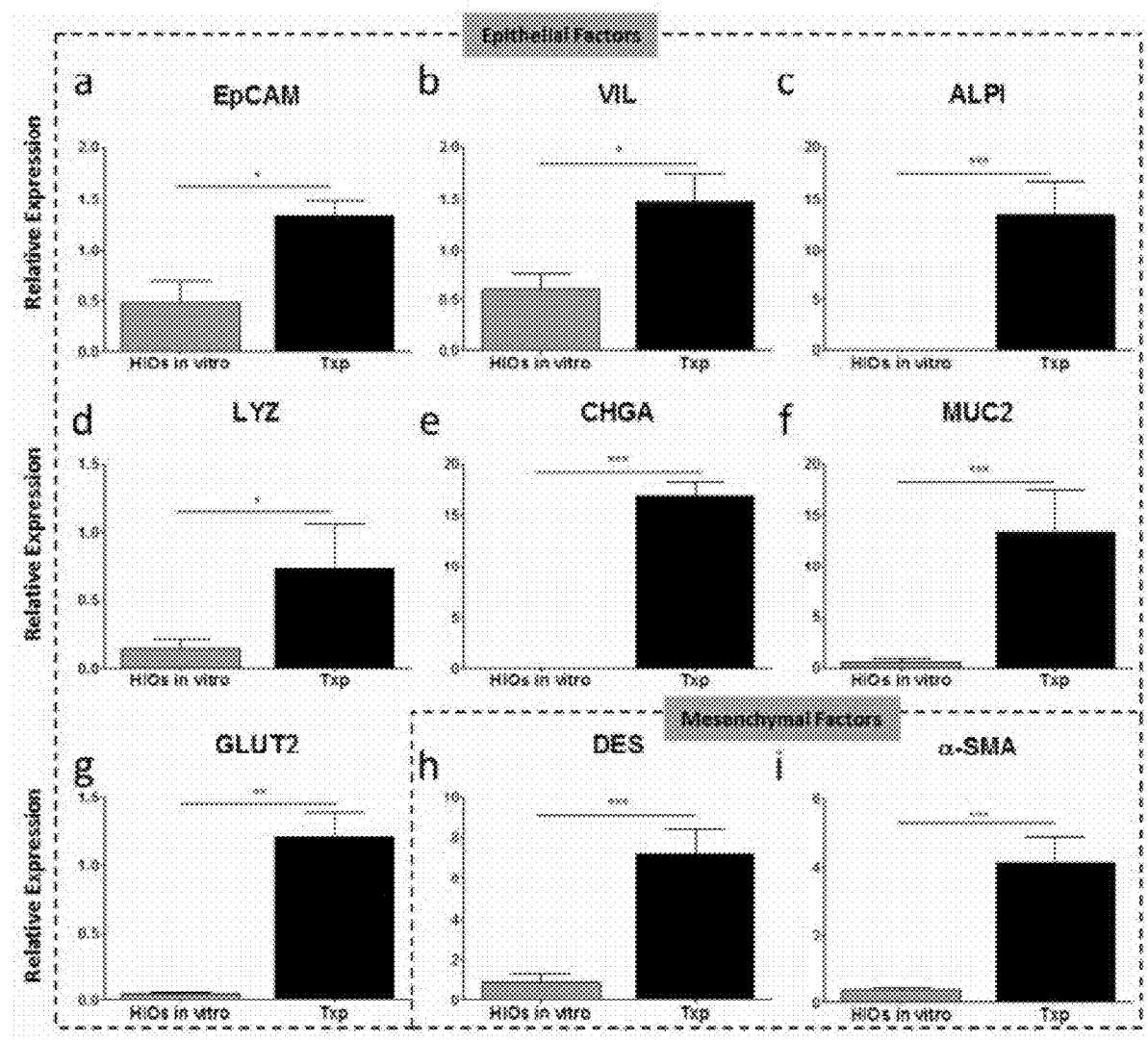

FIG. 8. Additional epithelial and mesenchymal markers of maturity in transplanted HIOs vs HIOs in vitro. (FIGS. 8A-G) Comparison of relative gene expression of epithelial markers including EpCAM (FIG. 8A), Villin (VIL) (FIG. 8B), Alkaline phosphatase (ALPI) FIG. 8C, Lysozyme (LYZ) (FIG. 8D), Chromogranin A (CHGA) (FIG. 8E), Mucin (MUC2) (FIG. 8F), and Glucose transporter 2 (GLUT2) (FIG. 8G). (FIGS. 8H-I) Relative expression of smooth muscle markers Desmin (DES) (FIG. 8H) and smooth muscle actin (α-SMA) (FIG. 8I). Values in graphs represent Mean±s.e.m. ns, not significant. *, p<0.05; , p<0.01; *, p<0.001; HIOs in vitro: n=4; Transplants (Txp): n=8.

Figure 9:
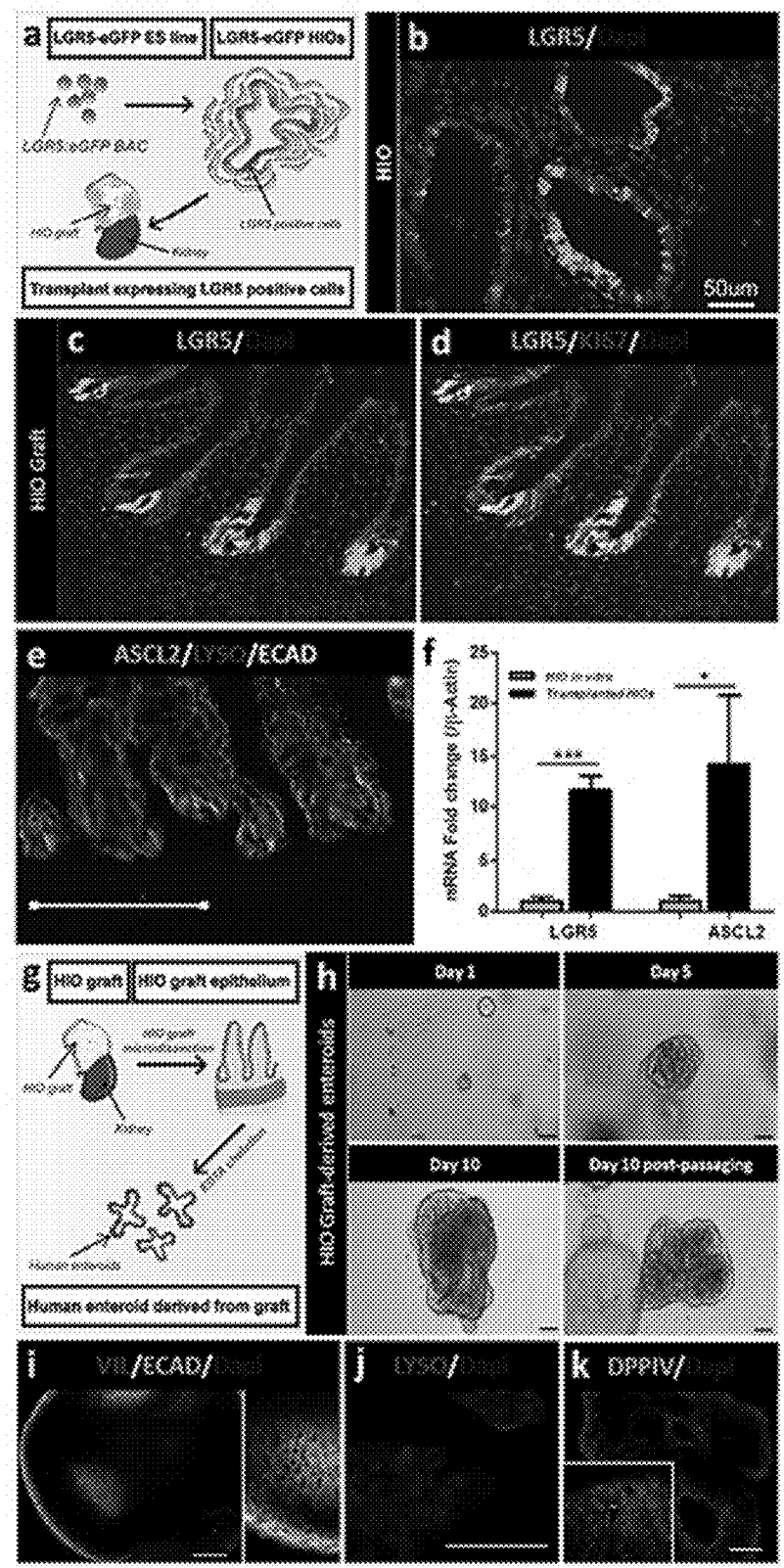

FIG. 9. Engrafted tissue displayed a mature epithelium maintained by intestinal stem cells. (FIGS. 9A-D) An LGR5R5:eGFP BAC reporter ES line has been established and was used to generate HIOs expressing LGR5-eGFP cells FIG. 9A. LGR5-eGFP cells (green) were seen within an HIO in vitro scattered throughout the epithelium (FIG. 9B) and are localized in proliferative crypt base cells (colocalization with KI67), as expected in engrafted human intestinal tissue (FIGS. 9C-D). FIG. 9E. Immunofluorescence staining of stem cell marker ASCL2 (green) localized within the crypt bases of the engraftment. FIG. 9 F. Graph demonstrated relative fold changes of LGR5 and ASCL2 within HIOs in vitro prior to transplant and in engraftments. FIG. 9G. Enteroids were generated from the engrafted epithelium to demonstrate the stemness of the tissue. FIG. 9H. Panel shows Engraftment-derived epithelial enteroids following initial plating at days 1, 5, and 10 and after passaging. (FIGS. 9I-K) Immunofluorescence staining revealed the presence of epithelial cells with Villin (VIL) and E-cadherin (ECAD) (FIG. 9I) as well as the presence of Paneth cells (Lysozyme—LYSO) (FIG. 9J) and brush border enzyme (Dipeptidyl peptidase 4-DPPIV) (FIG. 9K) (All scale bars 50 µm).

Figure 10:
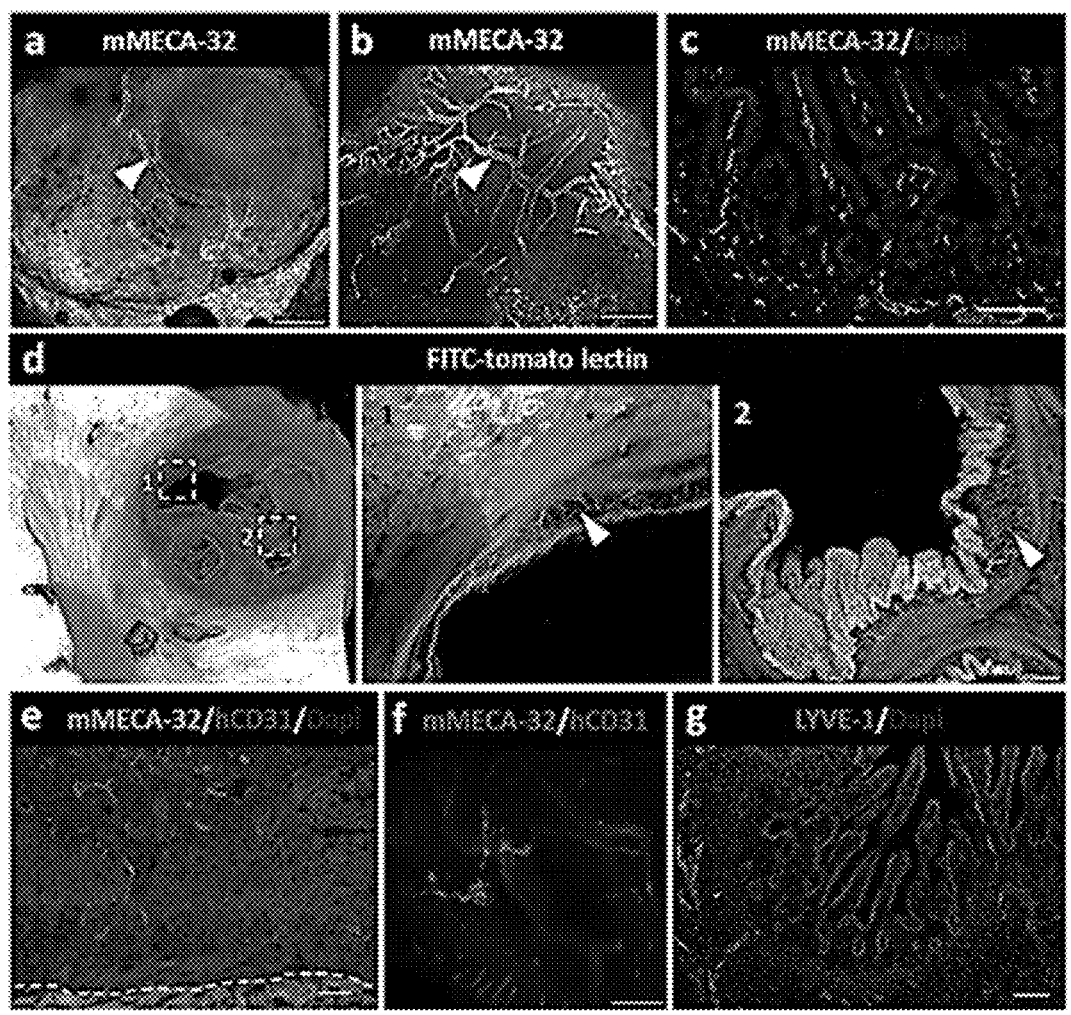

FIG. 10. Engrafted intestinal tissue received its blood supply from the ingrowth of murine vasculature. FIG. 10A. A panendothelial antibody specific to mouse (mMECA-32) is used to reveal murine vasculature just below the surface of an engraftment (FIG. 10b) as well as within the interior of an engraftment (white arrowheads; Scale bars 50 µm). FIG. 10C. Magnified immunofluorescence image of mMECA-32 stained endothelium (green) comprising the vasculature within each villi as well as the capillary plexus just beneath the epithelium within the engraftment. FIG. 10D. Whole mount staining of engraftment within the kidney following FITC-labelled tomato lectin injections via mouse tail vein. Outlined areas 1 and 2 correspond with following images revealing functional fluorescent murine vasculature within the engraftments (Scale bars 50 µm). FIG. 10E Immunofluorescence image revealing murine-specific (mMECA-32) and human specific (hCD31) staining of endothelium within an engraftment. FIG. 10F. Confocal imaging on whole mount engraftments did not showed connections between the murine and human vasculature. FIG. 10G. A murine specific marker of lymphatic vessels (LYVE-1) demonstrated ingrowth of lymphatic vessels from the murine host. (All scale bars 100 µm except where specified).

Figure 11:
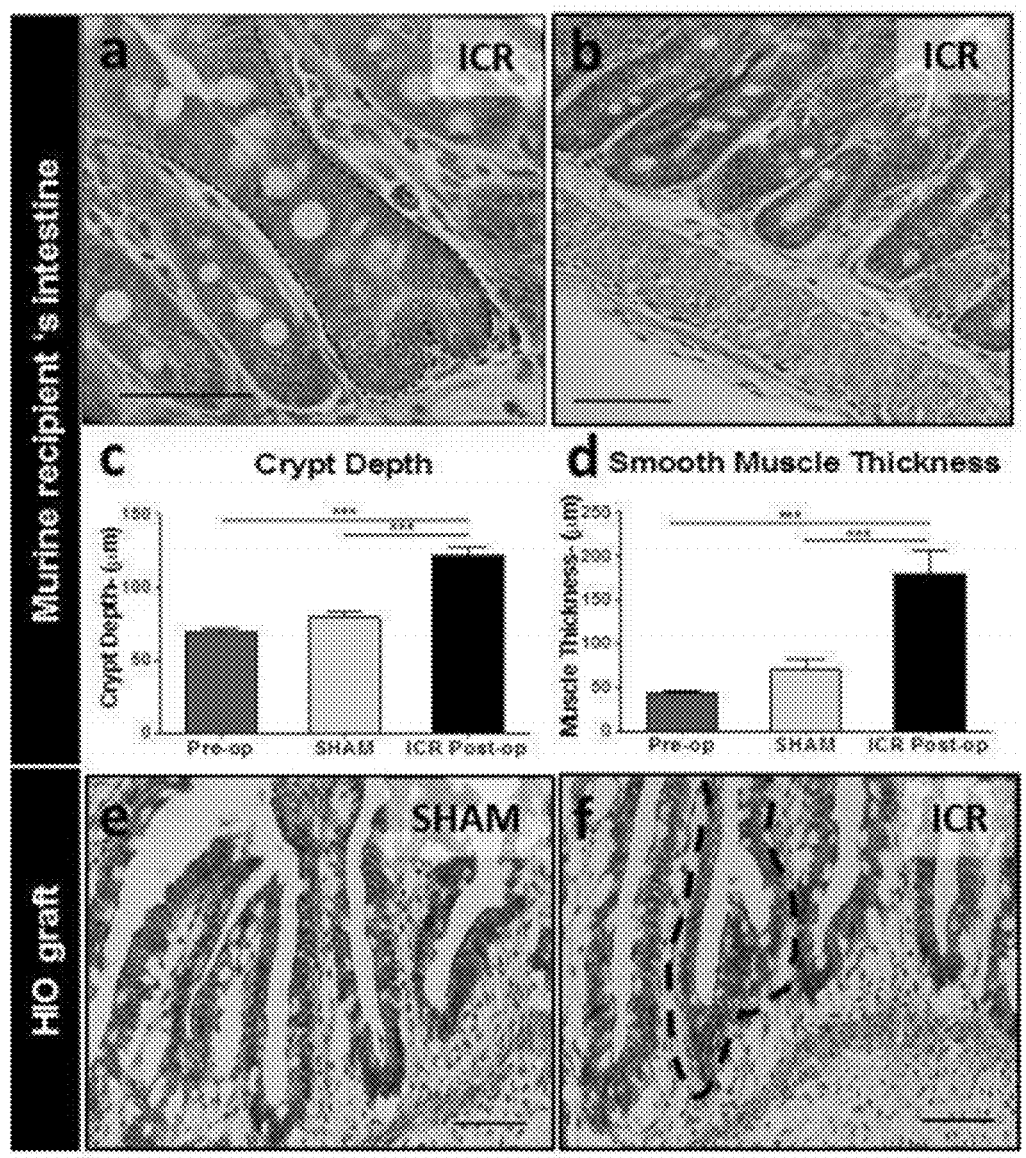

FIG. 11. NSG Mice also undergo intestinal adaptation following surgical resection as well as the HIO graft. FIG. 11A. Magnified image of crypt fission (outlined) in murine small intestine following resection. (Scale bar 50 µm). FIG. 11B. Increased thickness of smooth muscle layer (tunica muscularis) in postoperative ICR tissue (Scale bar 50 µm). FIG. 11C. Comparison in murine intestinal crypt depth (µm) between Pre-operative, sham, and resected (ICR) groups. FIG. 11D. Comparison of thickness of smooth muscle layer (µm) in Pre-operative, sham, and resected (ICR) groups.

FIG. 11E. Magnified image of intestinal epithelium in HIO graft in a sham mouse (Scale bar 50 μm). FIG. 11F. Magnified image of crypt fission (outlined) in HIO graft in an ICR mouse (Scale bar 50 μm). Values represented in graphs represent Mean±s.e.m. ns, not significant. *, p<0.05; , p<0.01; *, p<0.001; Pre-op group: n=13; sham group: n=10; ICR group: n=11.

Figure 12:
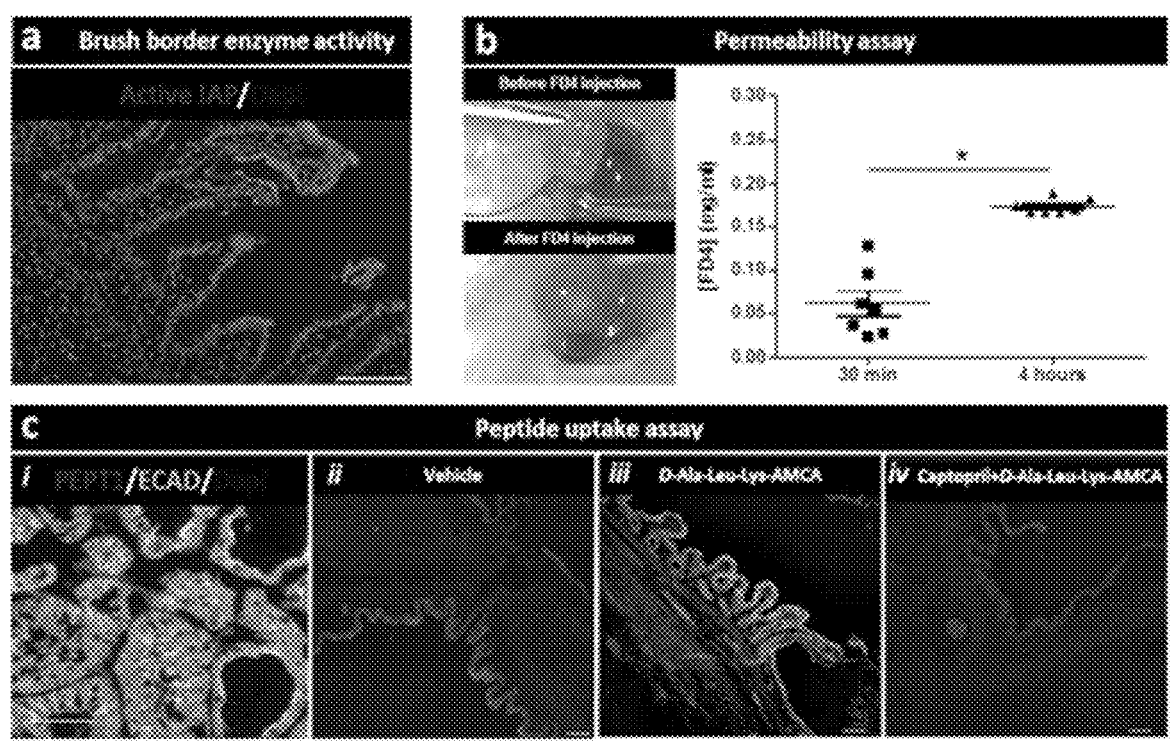

FIG. 12. Engrafted human intestinal tissue retained digestive and absorptive function. FIG. 12A. Intestinal alkaline phosphatase demonstrated activity ex vivo (Scale bar 100 um). FIG. 12B. FITC-Dextran (MW 4,400) injected into engraftments in vivo (pictures seen before and after) increased significantly in murine serum from initial timepoint of 30 minutes compared with timepoint of 4 hours within each mouse (n=7). Values represented in graph represent Mean±s.e.m.; ns, not significant; *, p<0.05; , p<0.01; *, p<0.001; paired t-test. FIG. 12C. D-Ala-Leu-Lys-AMCA peptide uptake assay revealing peptide transporter (PEPT1) staining within the epithelium of an engraftment (scale bar 100 μm) FIG. 12I. Additional images showing fluorescence within the epithelium following injections of vehicle (DMEM solution), D-Ala-Leu-Lys-AMCA (DMEM+labeled peptide solution), and Captopril+D-Ala-Leu-Lys-AMCA (DMEM+labeled peptide+competitive inhibitor of transport solution) (n=3 for each group). Fluorescence was observed following injection of labeled peptide (iii), but little to no fluorescence was observed with either vehicle injection (ii) or with labeled-peptide+captopril injection (iv).

Figure 13:
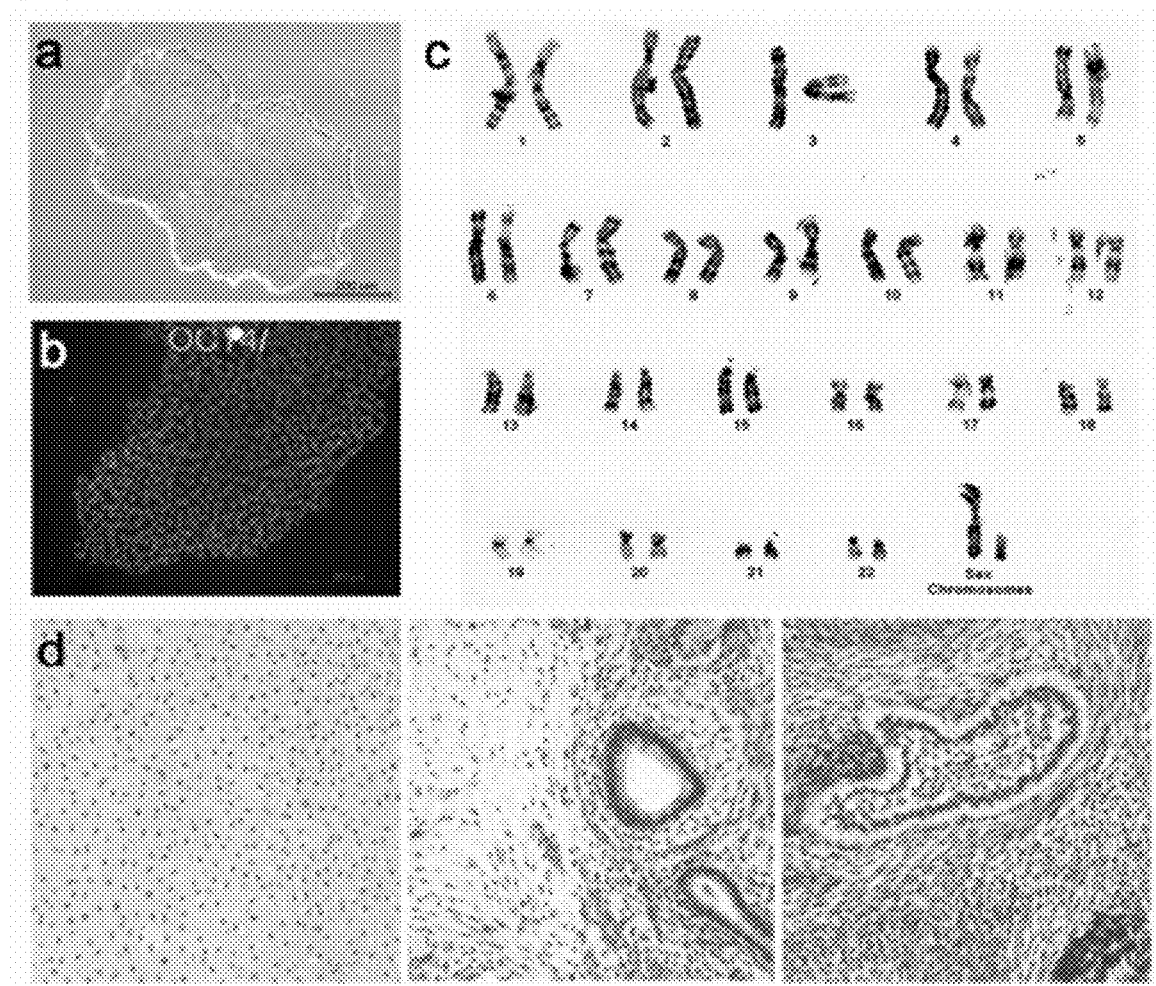

FIG. 13. Quality control assays for iPSCs. FIG. 13A. Phase contrast image of iPSC colonies cultured in standard feeder free conditions. FIG. 13 B Immunofluorescence staining of pluripotency markers Oct4 and Nanog in iPSCs. FIG. 13C. G-banded karyotype analysis demonstrating normal (46,XY) karyotype of control iPSCs. FIG. 13D. H&E stained sections of a teratoma derived from iPSCs showed tissue arising from the three embryonic germ layers, endoderm, ectoderm and mesoderm. Control teratomas presented stellate reticular cells surrounded by peripheral epithelium with anti-basal nuclei consistent with primitive tooth (ectoderm), ciliated columnar epithelium consistent with intestine (endoderm), and cartilage cells (mesoderm). The images are 400-fold magnification.

Figure 14:
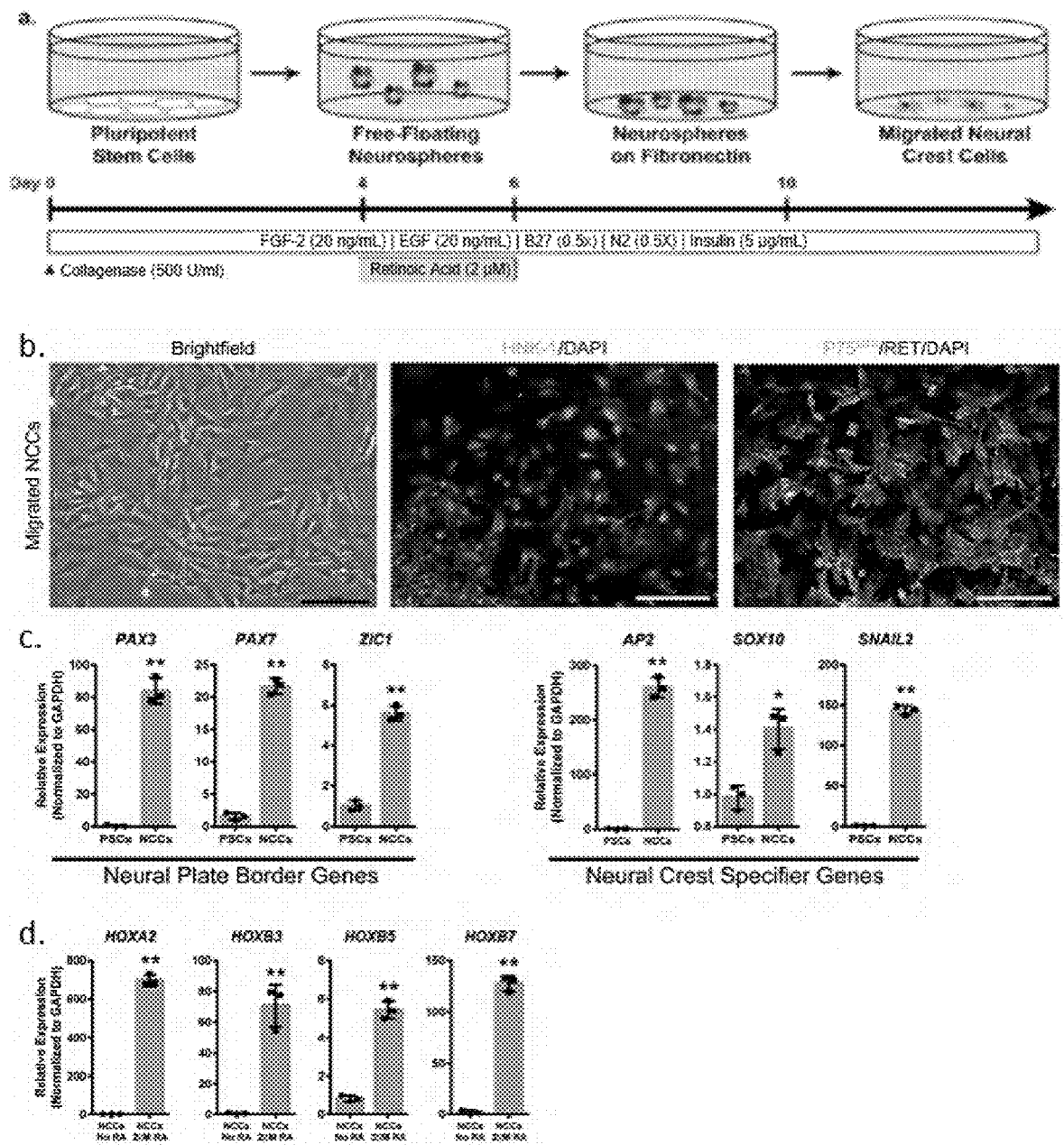

FIG. 14. Generating Vagal-like Neural Crest Cells (NCCs). 14A—Schematic representation of protocol for generating neural crest cells expressing Hox genes. While this method has been reported to generate cranial NCCs 9 addition of retinoic acid during the last 48 hours of neurosphere culture induces Hox A2, B3, B5 and B7, markers of posterior/vagal-like NCCs. FIG. 1B—NCCs displayed stellate morphology and were positive for surface markers HNK-1, p75NTR, and RET. FIG. 41C—Quantitative RT-PCR analysis for of neural plate border and regulators of neural crest cell specification. FIG. 1D—Treatment of neurospheres for 48 hours with RA results in the formation of NCCs that express Vagal-level HOX genes. The more posterior HOX genes B3, 5, and 7 showed dose-dependent increase in levels of expression (data not shown). Scale bars, 100 μM. Values in graphs represent mean±s.e.m.; * P<0.01, ** P<0.001; Student's t-test (two-tailed, unpaired); n=3 biological replicates per condition; data representative of 3 independent experiments.

Figure 15:
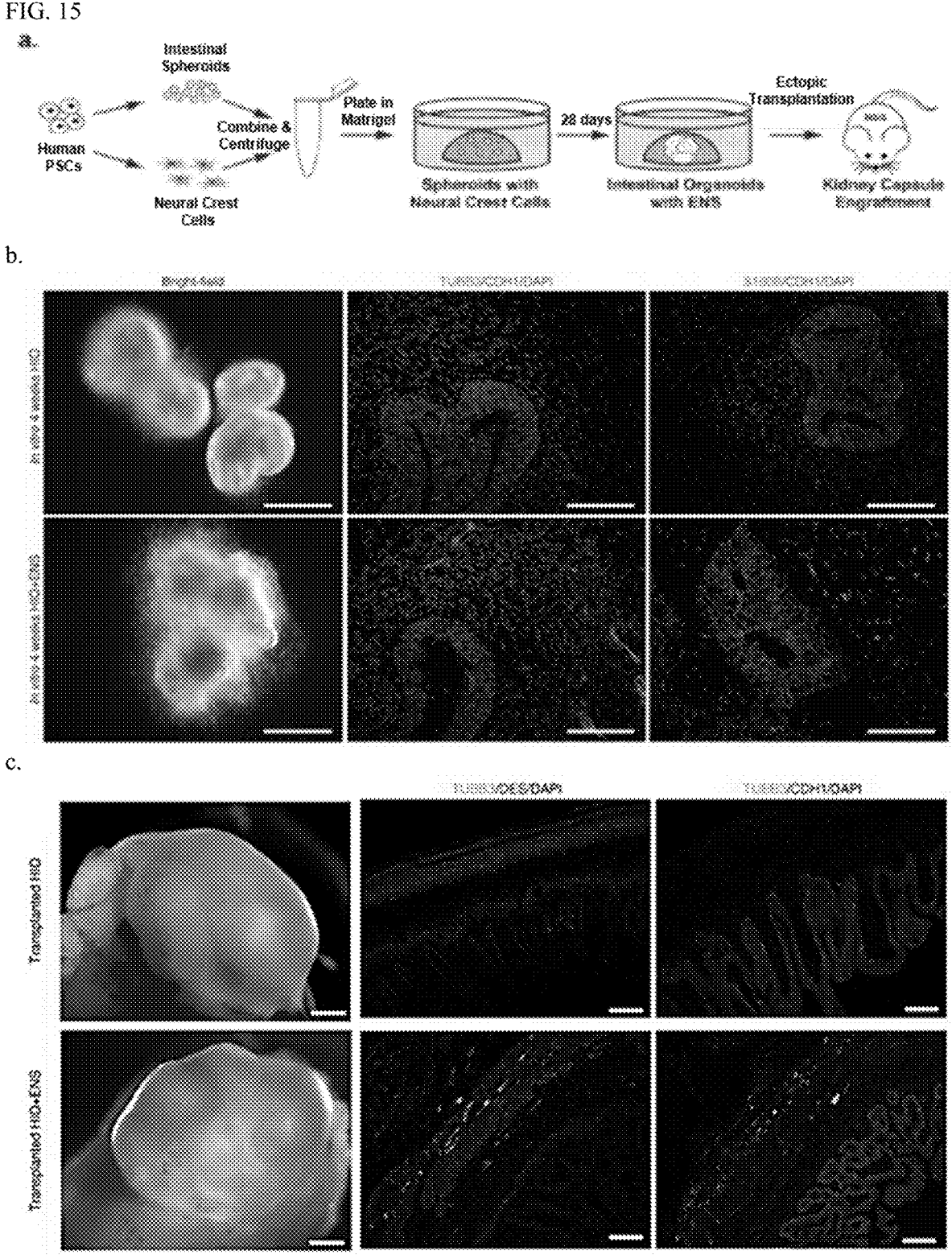

FIGS. 15A-C. Incorporation of NCCs into developing HIOs in vitro. FIG. 15A—Schematic for incorporating NCCs into HIOs. HIOs and NCCs were generated separately, combined by low-speed centrifugation, embedded in Matrigel and grown for 4 weeks in vitro. In some cases, HIOs were transplanted into NSG mice and grown in vivo for 6-8 weeks. FIG. 15B—In vitro growth of HIOs. Left panel—Bright-field images of 28d HIOs+/−NCCs. Scale bar, 1 mm. Middle panel—Immunostaining for neurons (βIII-tubulin) and epithelium (E-cadherin). Right panel—Immunostaining for glial cells (S100+) and epithelium (E-cadherin). Scale bar, 100 μm. Data is representative of 14 independent experiments combining HIOs with NCCs in vitro. FIG. 15C—In vivo growth of HIOs+NCCs. HIOs±NCCs were transplanted into the kidney subcapsular space of NSG mice and grown for 6 weeks. Left panels show HIOs±NCCs that were ~1 cm in diameter. Scale bar, 1 mm. Middle panels show the formation of neurons adjacent to smooth muscle fibers (Desmin+) in a myenteric-like position, oriented perpendicular to one another in HIOs—NCC, demonstrating that smooth muscle development occurs in the absence of an ENS. A second layer of desmin+ cells is located submucosally to the epithelium. HIOs+NCCs contain neurons (BIII-tubulin+) that are embedded within the Desmin+ smooth muscle layers and have an organization that closely resembles a myenteric plexus. Right panels show that glial cells (S100+) are also embedded within the mesenchymal layers of HIOs+NCCs, including the submucosal layer.

Figure 16:
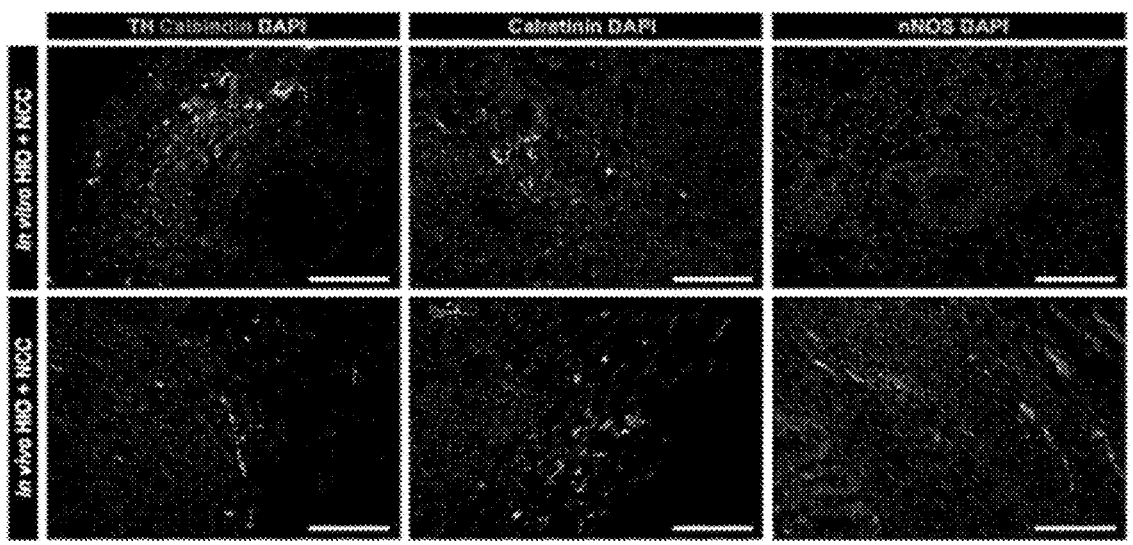
Figure 16:
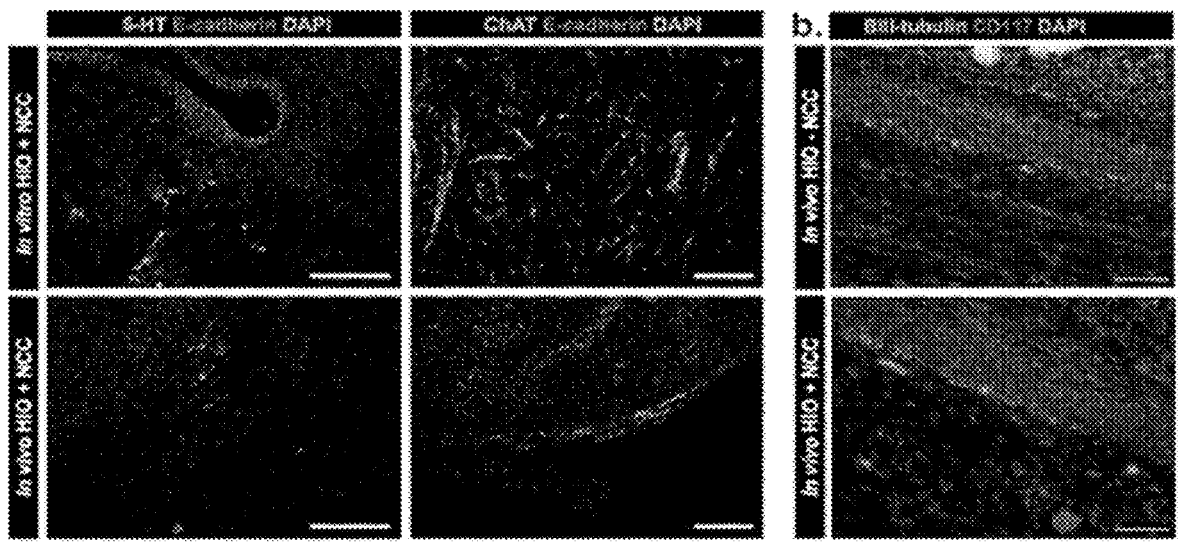

FIGs. 16A-B. Neuronal diversity and formation of interstitial cells of Cajal (ICC). FIG. 16A. Analysis of different neuronal cell types using neurochemical markers of ENS neurons in HIOs+NCCs cultured in vitro (upper panels) and following engraftment in vivo (lower panels). Dopaminergic neurons (TH), interneurons (ChAT, 5-HT), sensory neurons (Calbindin), excitatory neurons (Calretinin) and inhibitory neurons (nNOS) were all found in in vivo engrafted HIOs+NCCs. In contrast, in vitro HIOs+NCCs did not contain inhibitory neurons (nNOS), suggesting that they were embryonic in nature. FIG. 16B. Formation of interstitial cells of Cajal (CD117—red) in HIOs+NCCs in vivo. HIOs without NCCs did not form neurons (BIII-tubulin—green) and had fewer CD117+ cells, suggesting that differentiation of ICCs may involve NCCs.

Figure 17:
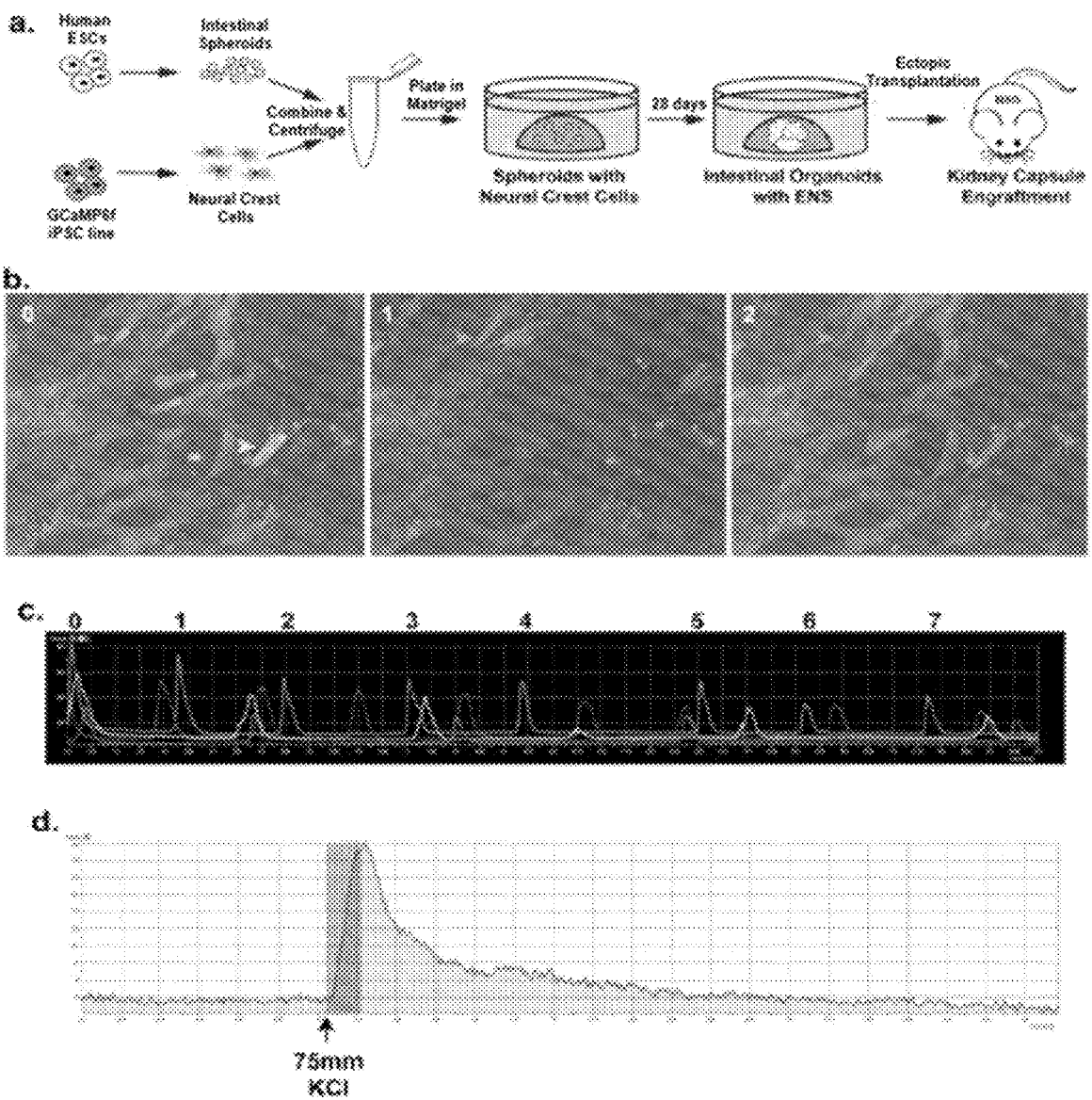

FIGS. 17A-D. Live imaging of neural activity in HIOs+NCCs. FIG. 17A. Schematic representation of protocol for combining NCCs generated from GCaMP6f expressing PSCs with HIOs generated from H1 PSCs. FIG. 17B. Live imaging of Ca2+ flux in the neural crest derived ENS cells shows periodic activity. Snapshots from a 20 min time-lapse movie showing neural activity in HIOs+NCCs. Colored arrows point to cells whose pixel intensity was measured over time and shown in FIG. 17C. FIG. 17C. Numbered snapshots correspond to the arrowheads in FIG. 17B showing the rhythmic waves of depolarization of single neurons in HIO+NCC cultures (only the first 3 time points were shown in FIG. 17B). The graph measures pixel intensity related to Ca2+ flux. The color of the line corresponds to the same colored arrowhead in the snapshots. FIG. 17D KC1 induces wave of Calcium efflux. Quantification of pixel intensity from KC1 experiment shows that KC1 induces a rapid and broad wave of depolarization of ENS cells.

FIGS. 18A-C. Formation of a 3-dimensional submucosal and myenteric plexus that controls motility. FIG. 18A Whole mount immunostaining and 3-D imaging of human intestine and HIO+ENS tissues. En face view of human submucosa and HIOs+ENS, showing arrangement of neurons (BIII-tubulin) and glia (S100) into a neuroglial plexus that integrates and orients with smooth muscle fibers (desmin). HIO+ENS tissues also contained a neuroglial plexus that oriented with smooth muscle fibers. FIG. 18B—Formation of an enteric and submucosal plexus. Left panel—en face view of in vivo engrafted HIO+NCCs shows close association of glia (S100) around the epithelium (dapi—blue). Right panel—a lateral view of whole-mount images clearly identifies two plexuses; one associated with the epithelial mucosa (submucosal plexus) and the other associated with outer layers of smooth muscle (myenteric plexus). FIG. 18C The ENS in HIOs mediates peristaltic-like contractions. In vivo grown tissues were explanted into Tyrode's solution and subjected to an electrical field stimulation (EFS). HIO— ENS that were subjected to a high voltage EFS (1 ms pulse at 100V) had one single contraction (n=2). HIO+ENS that were subjected to a low voltage EFS (1 ms pulse at 50V) had a sustained series of wave-like contractions (n=5) that were lost when tissues were cultured in the tetrodotoxin (HIO+ ENS+TTX, n=2).

Figure 19:
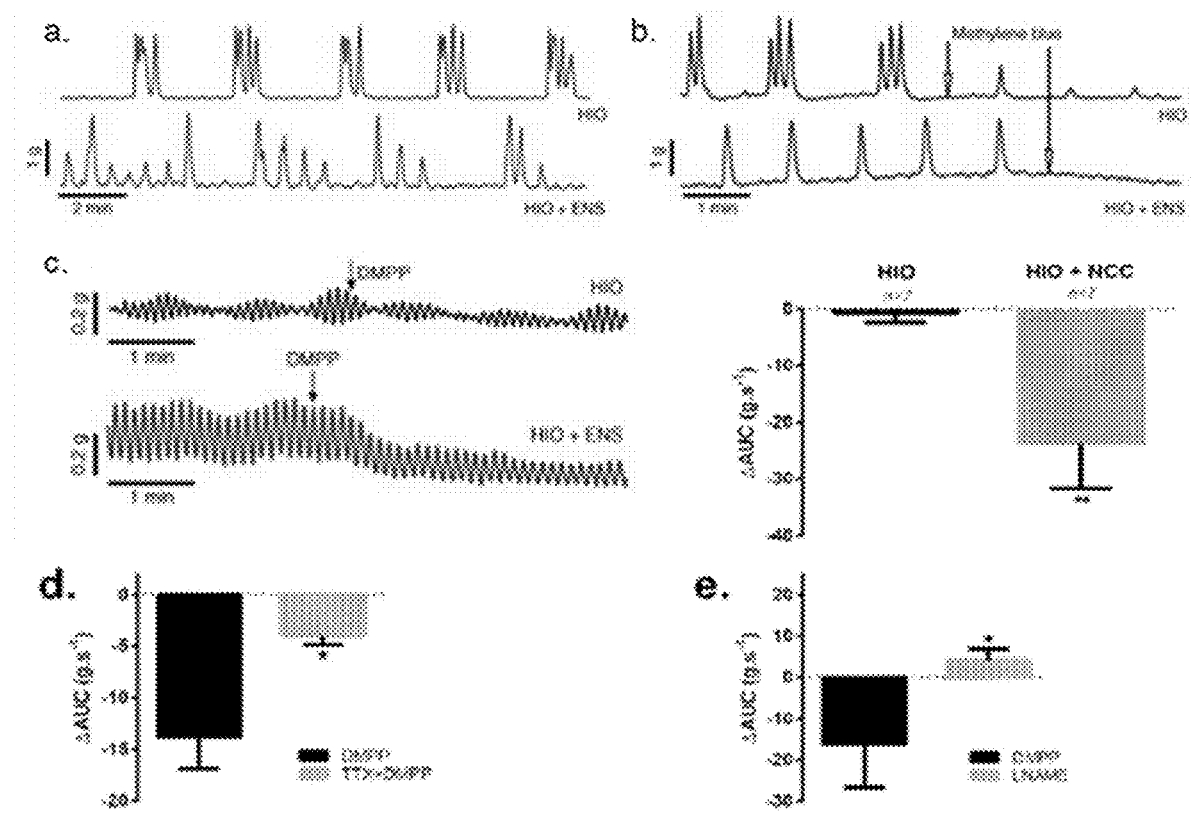

FIGS. 19A-E. ENS-dependent and independent control of contractile activity. FIG. 6A Recordings of spontaneous contractions in transplanted HIOs and HIO+ENS tissue strips. Phasic contractions were observed after tissue equilibration (no stimulation) suggestive of interstitial cells of Cajal (ICCs) present in both HIO (n=7) and HIO+ENS (n=7) tissues. FIG. 19B—Recordings showing an inhibition of ICCs activity with Methylene Blue leading to loss of contractile activity (n=3). FIG. 19C—Left panel shows representative images of Dimethylphenylpiperazinium (DMPP) stimulation in HIO and HIO+ENS. Right panel represents area under the curve (AUC) during DMPP (10 μM) stimulation measured for 2 minutes before and after stimulation (n=7). FIG. 6D—TTX inhibition of ENS activation. Area under the curve during DMPP stimulation measured for 2 minutes after stimulation, followed by tetrodotoxin (TTX; 10 μM) treatment in HIO+ENS (n=7). FIG. 19E—ENS-induced relaxation by a NO-dependent mechanism. Area under the curve during DMPP stimulation measured for 2 minutes after stimulation, followed by NG-nitro-L-arginine methyl ester (L-NAME) treatment in HIO+ENS (n=7). Values in graphs represent mean±s.e.m.; * $P<0.05$, ** $P<0.01$; Mann & Whitney test.

Figure 20:
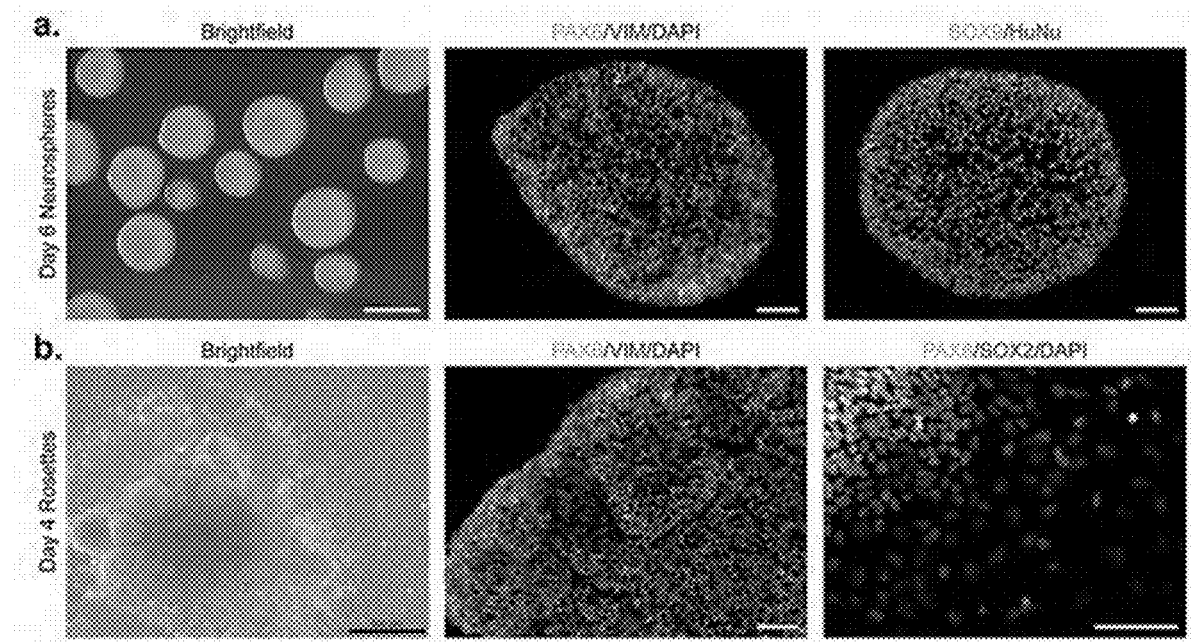

FIG. 20. Characterization of developing neural crest cells. FIG. 20A. Day 6 free-floating neurospheres are roughly 500 μm in diameter and positive for PAX6, Vimentin, and SOX9; characteristic of neural stem cells and the lateral neural plate where neural crest cells form. FIG. 20B. Neurospheres attached to a fibronectin substrate and formed neural rosettes visible with bright field microscopy. Attached neurospheres broadly expressed PAX6 whereas Vimentin staining was observed at the edge of neural rosettes where NCCs were delaminating. As NCCs migrated away from rosettes, PAX6 was down regulated whereas SOX2 expression was maintained.

Figure 21:
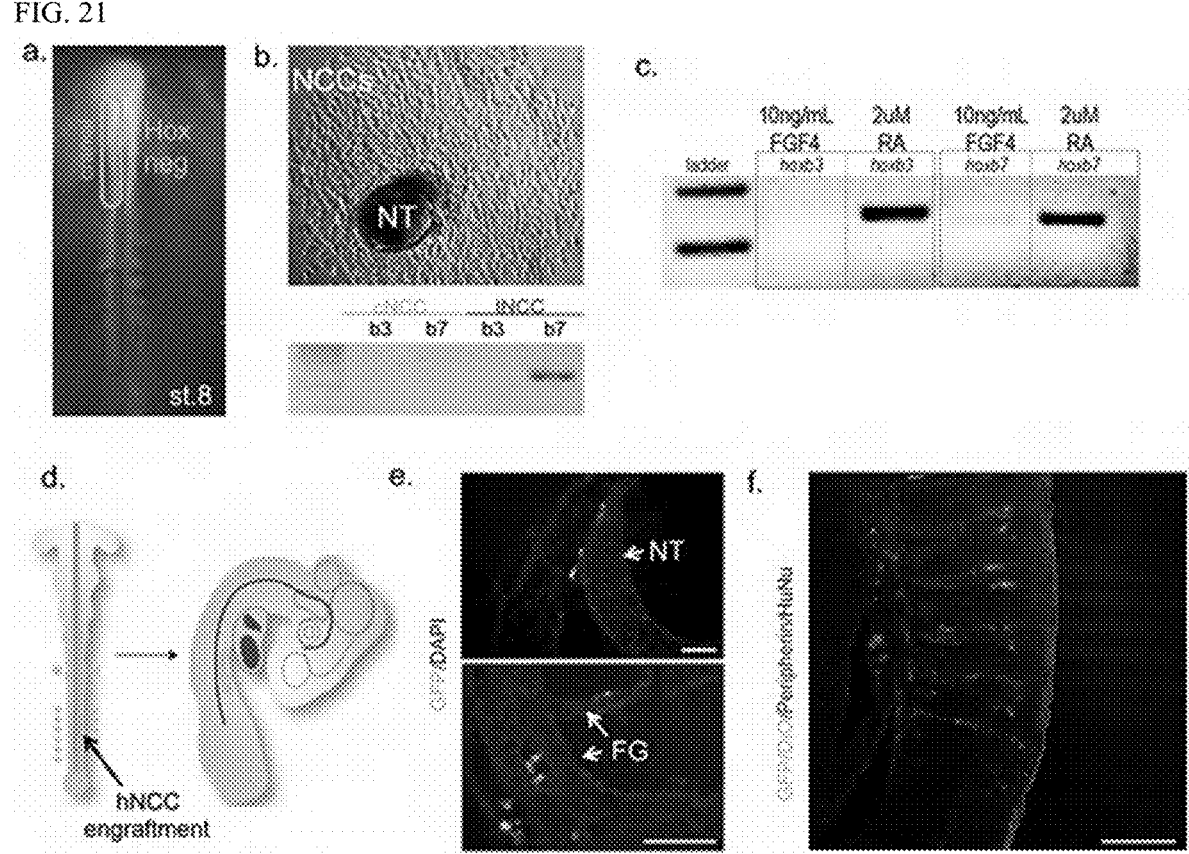

FIG. 21. Comparison of human and chick NCC behavior. (FIG. 21A and FIG. 21B) Isolation and culturing of cranial (Hox-negative) and trunk (Hox-positive) NCCs from chick embryos and analysis of Hox gene expression. NCCs isolated from anterior chicken neural tube do not express Hox genes while those isolated from posterior neural tube are HoxB7 positive. (FIG. 21C) Chicken cranial NCCs express vagal-level Hox genes HoxB3 and HoxB7 when treated with 2 μM RA for 48 hours. A different posterizing factor, FGF4, had no effect on Hox gene expression. (FIG. 21D) Schematic describing engraftment of human PSC-derived NCCs into chicken embryos. GFP-labeled human NCCs were injected intersomitically into HH10-12 chick embryos in ovo. (FIG. 21E) Embryos were analyzed at ~HH38. GFP-labeled cells had migrated laterally along the neural tube (NT) and could be found colonizing the foregut (FG). (FIG. 21F) Differentiation of GFP-labeled cells into peripheral neurons (peripherin) (dorsal, right; anterior, up).

Figure 22:
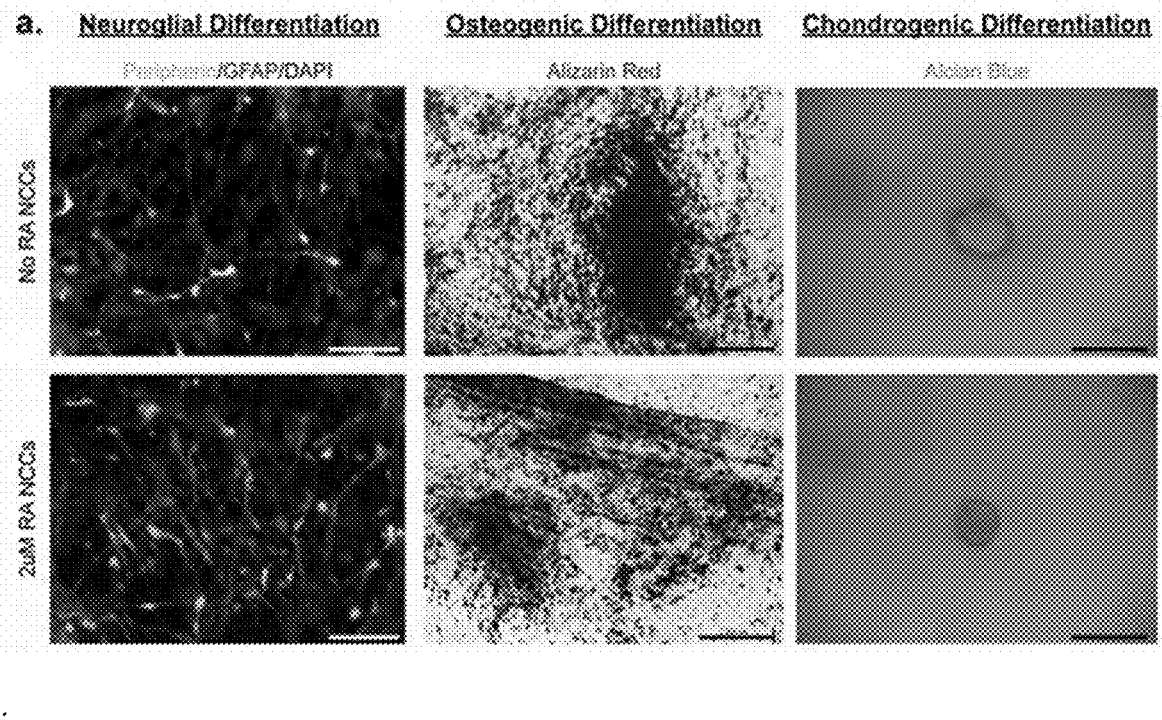
Figure 22:
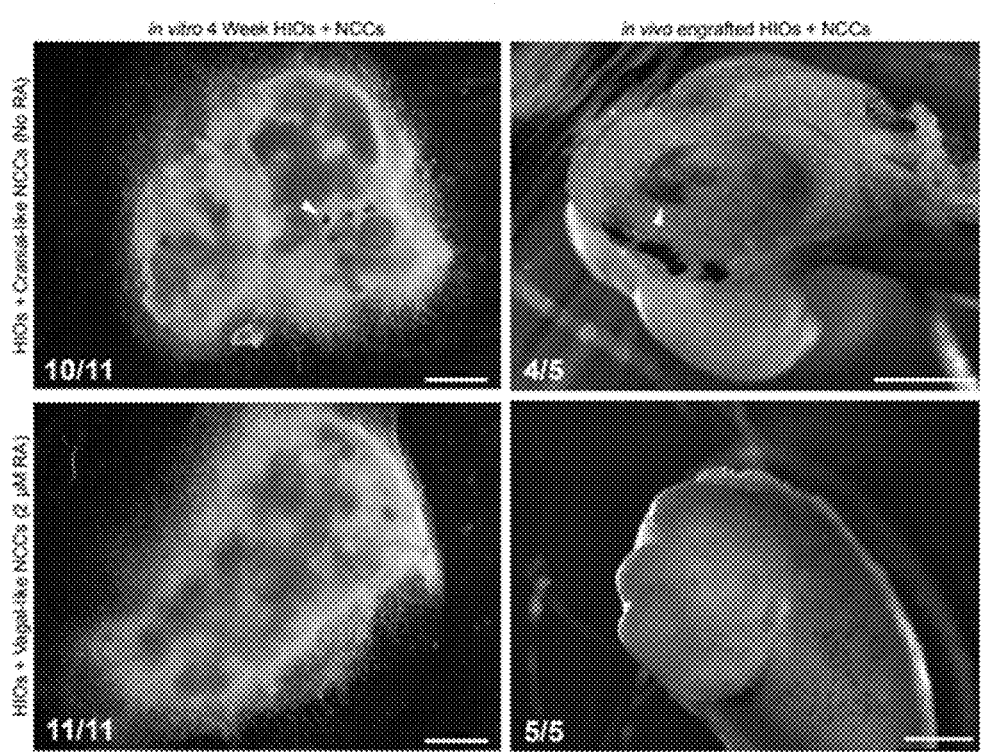

FIG. 22. Differentiation potential of cranial and RA-treated NCCs. FIG. 22A. In vitro differentiation of human PSC-derived NCCs into neuroglia lineages and mesenchymal lineages (osteocytes and chondrocytes). Cranial and RA-treated NCCs were equally competent to form neuroglial lineages (peripherin and GFAP), osteocytes (alizarin red) and chondrocytes (alcian blue) in vitro. FIG. 22b. Cranial-like NCCs formed pigmented epithelium (arrowhead) in vitro and in vivo, suggesting a retained competence to form neuroepithelium.

Figure 23:
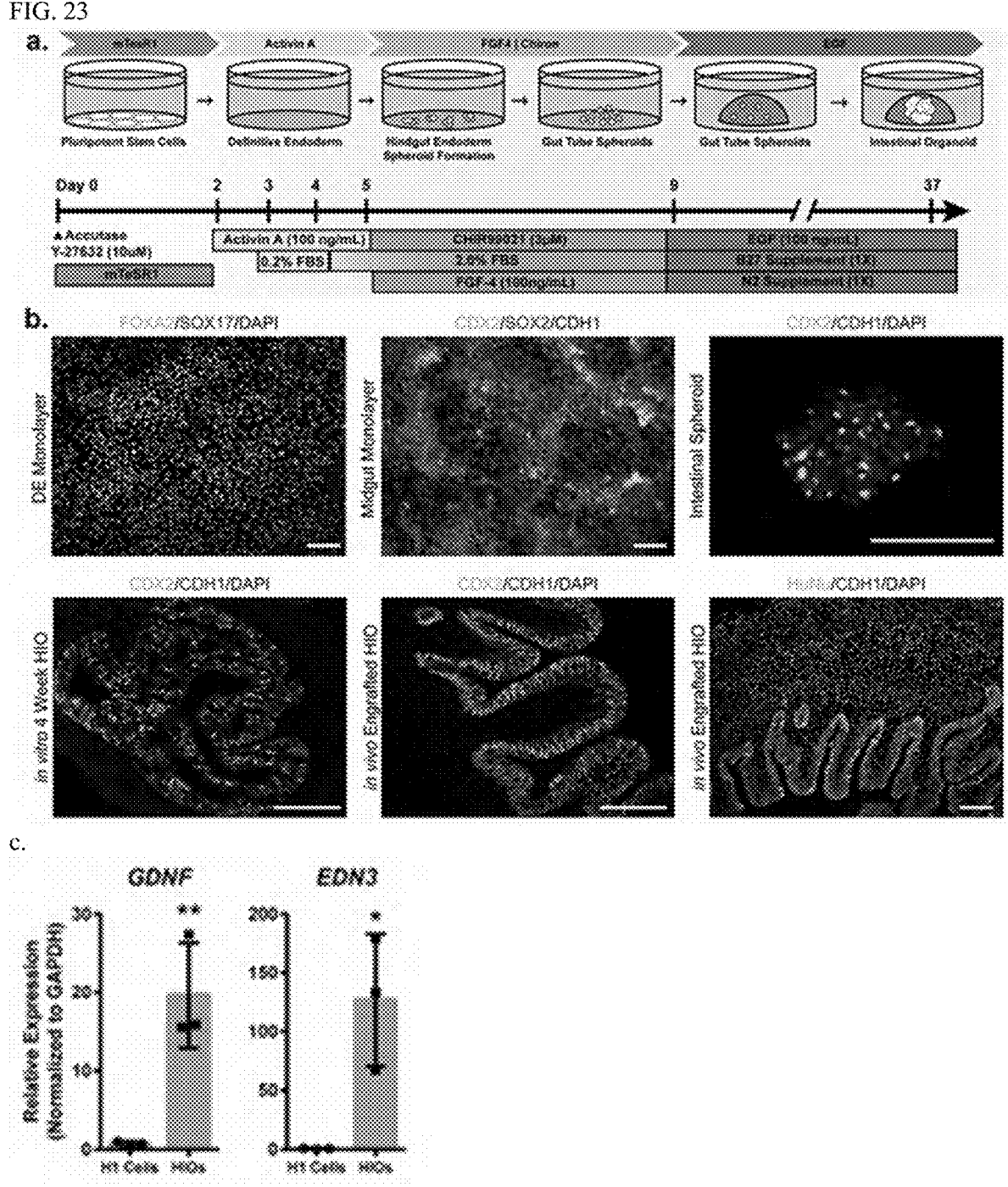

FIG. 23. Generation of Human Intestinal Organoids (HIOs) and expression of NCC migratory cues. FIG. 23A. Method for generating HIOs through directed differentiation of human pluripotent stem cells. FIG. 23B. Temporal expression of differentiation markers at each stage of HIO development. Activin A mediated efficient differentiation into definitive endoderm (FOXA2 and SOX17), WNT activation in combination with FGF4 induced CDX2 expression in monolayers and free-floating spheroids. Growth of spheroids in Matrigel for 4 weeks resulted in the formation of HIOs expressing CDX2. HIOs were engrafted into the subcapsular space of mice, where after 6 weeks they grew and matured to form intestinal tissue with crypts and villi. The human-specific antibody HuNu shows that intestinal epithelium and mesenchyme are human in origin. FIG. 23C. HIOs formed in vitro expressed GDNF and EDN3. Values in graphs represent mean±s.e.m.; * $P<0.05$, ** $P<0.01$; t-test (two-tailed, unpaired); n=3 (biological replicates); data representative of 2 independent experiments.

Figure 24:
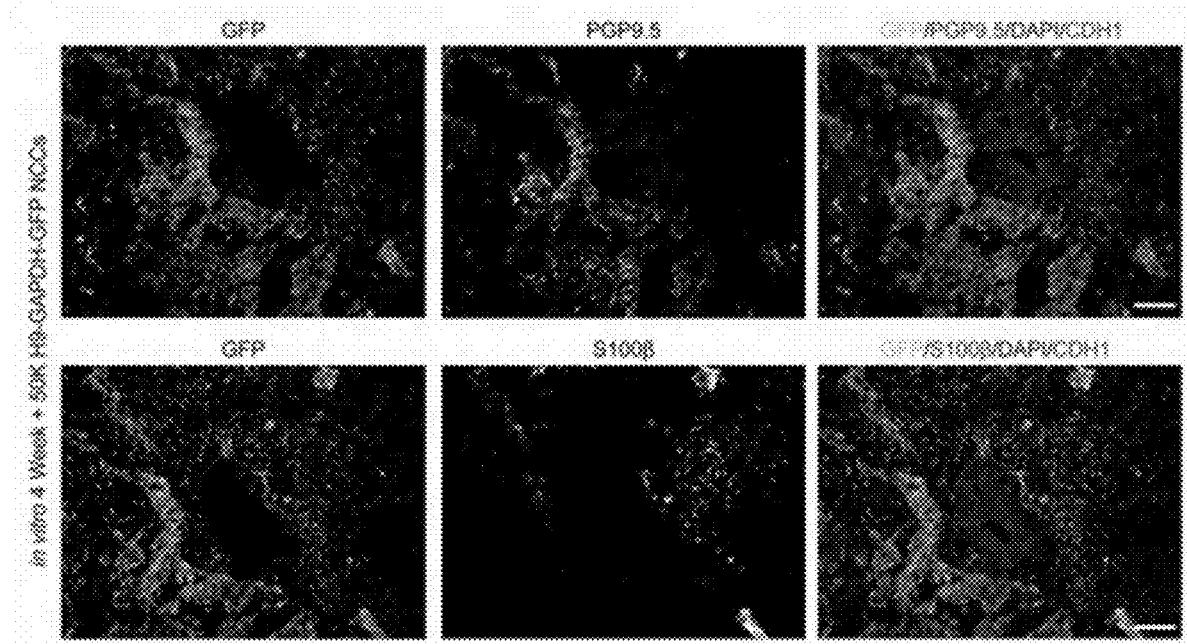

FIG. 24. Neurons and glia in HIOs+NCC cultures are NCC-derived. NCCs were generated from H9-GAPDH-GFP human embryonic stem cells, which ubiquitously express GFP, and combined with HIOs generated from H1 HESCs. HIOs were co-stained for GFP and pan-neuronal marker PGP9.5 or the glial marker S100. Neuroglial cells in HIOs+NCCs are NCC-derived as is evidenced by co-expression of GFP and neuroglial markers.

Figure 25:
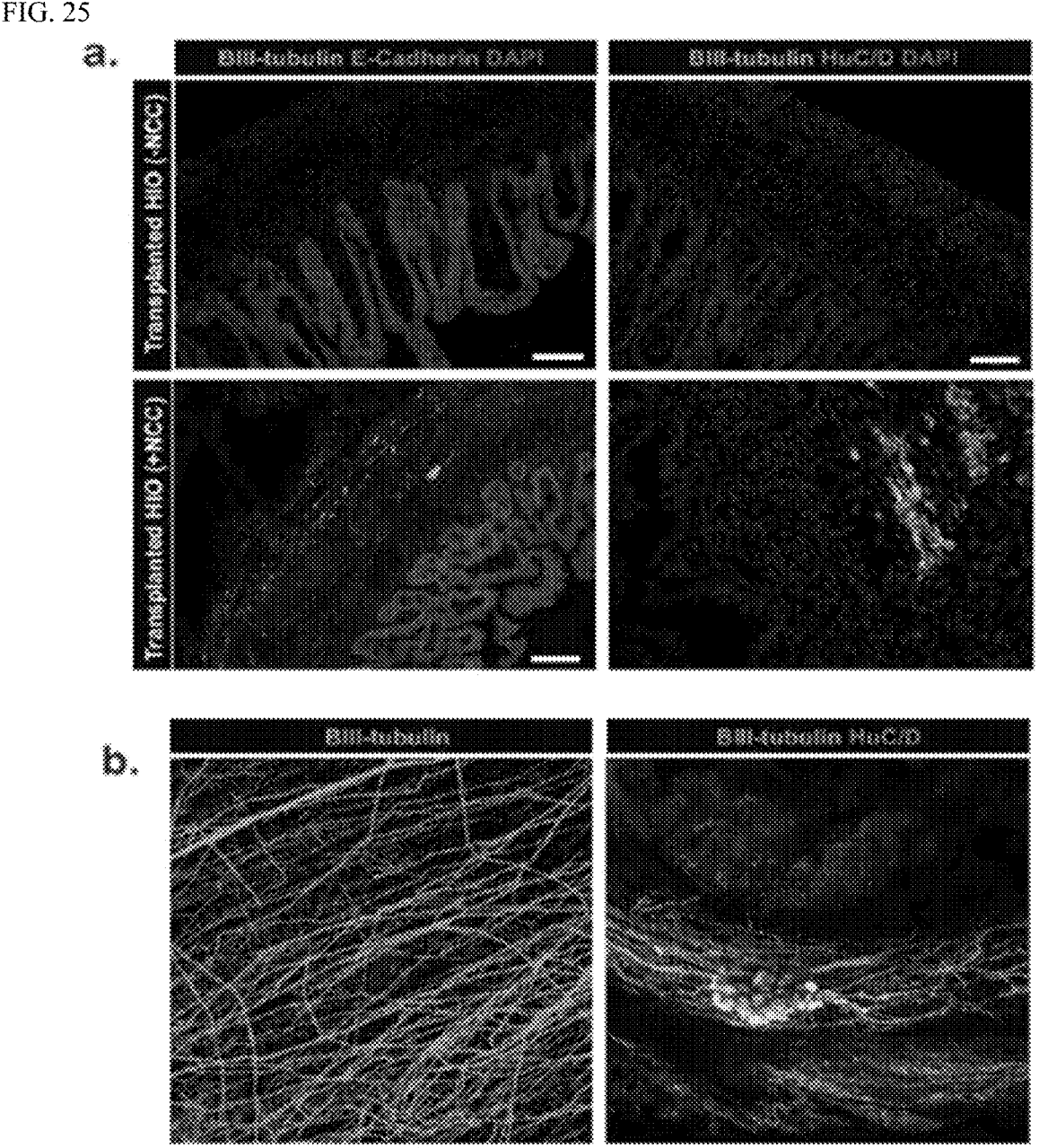

FIG. 25. Ganglia-like structures form in HIOs+NCCs grown in vivo. (FIG. 24A) In immunostained sections, Neurons (BIII-tubulin) were spread throughout the myenteric plexus and Applicant observed neuronal cell bodies (HuC/D) in clusters, similar to ganglia. (FIG. 24B) Whole mount immunostaining for neurons (BIII-tubulin, en face view) and neural cell bodies (HuC/D, lateral view) shows neuronal cell bodies organized into a ganglion-like clusters in HIOs+NCCs.

Figure 26:
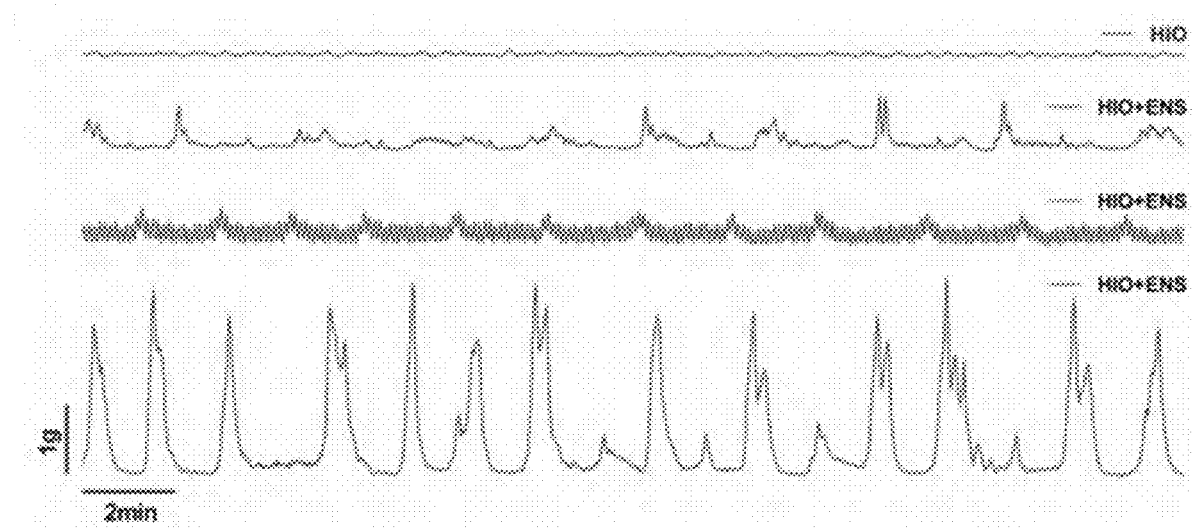

FIG. 26. Recordings of spontaneous contractions in transplanted HIOs and HIO+NCC tissues.

Figure 27:
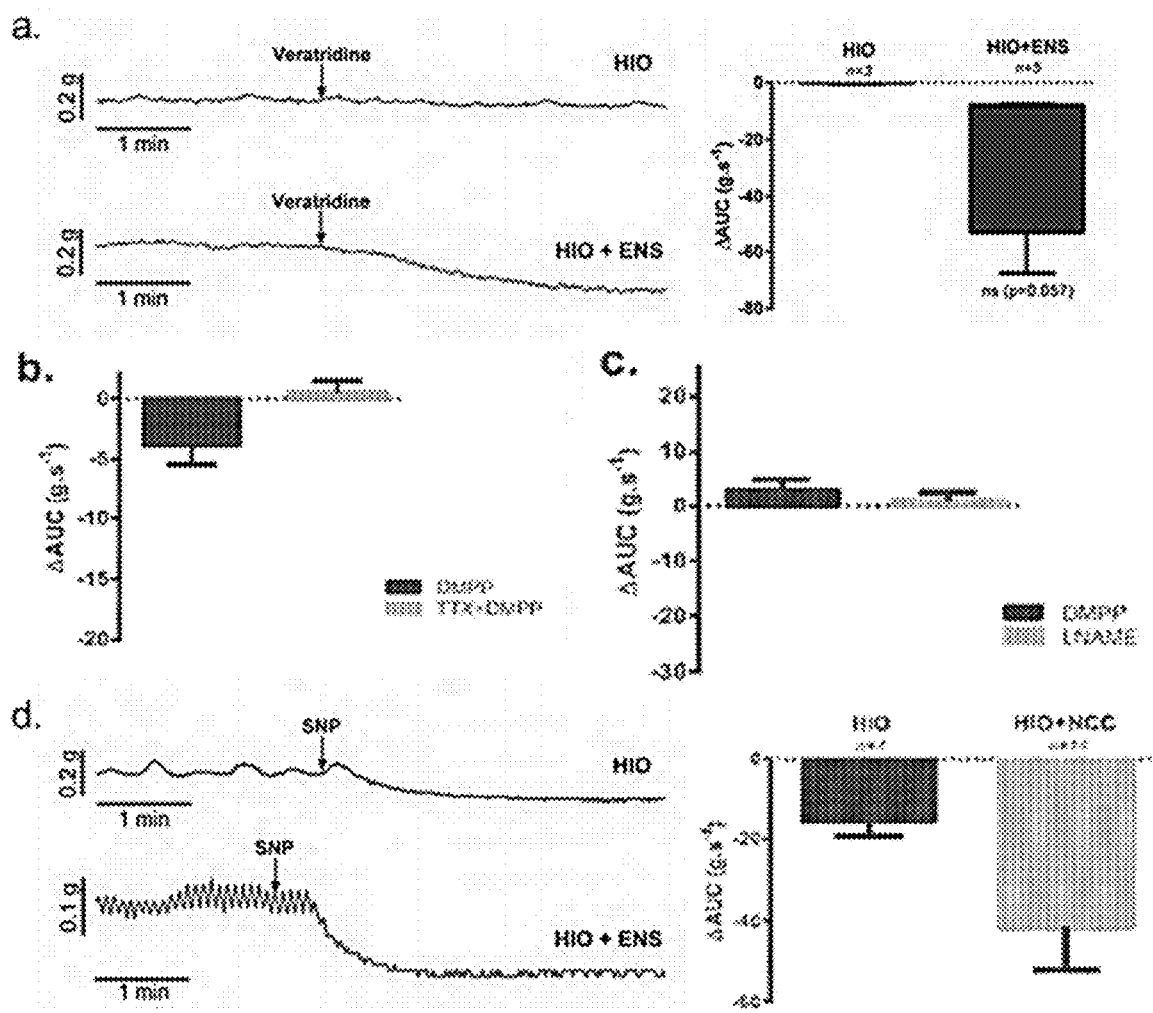

FIG. 27. (FIG. 27A) Left panel shows representative recording of Veratridine stimulation in HIO and HIO+NCC. Right panel represents area under the curve (AUC) during Veratridine (3 μM) stimulation measured for 2 minutes before and after stimulation (n=5). (FIG. 27B) Area under the curve during Dimethylphenylpiperazinium (DMPP; 10 μM) stimulation measured for 2 minutes before and after stimulation, followed by tetrodotoxin (TTX; 10 μM) treatment (n=3). (FIG. 27C) Area under the curve during DMPP stimulation measured for 2 minutes after stimulation, followed by NG-nitro-L-arginine methyl ester (L-NAME) treatment (n=3). (d) Left Panel representative recordings following Sodium Nitroprusside (SNP) stimulation of both HIO (n=4) and HIO+NCC tissues (n=14). Right Panel area under the curve during SNP stimulation measured for 2 minutes before and after stimulation. Values in graphs represent mean±s.e.m; Mann & Whitney test.

DETAILED DESCRIPTION OF THE INVENTION

The enteric nervous system (ENS) of the gastrointestinal (GI) tract controls motility, epithelial permeability and fluid exchange. Perturbations in ENS development or function are common, yet a human model to study ENS-intestinal biology is lacking.

Applicant has generated human intestinal organoids (HIOs) produced in vitro from human embryonic stem cells (ESCs) or induced pluripotent stem cells (iPSCs) that can engraft in vivo. These HIOs form mature intestinal epithelium with intestinal stem cells contributing to the cryvillus architecture and a laminated human mesenchyme, both supported by mouse vasculature ingrowth. Applicant has shown that in vivo transplantation resulted in marked expansion and maturation of the epithelium and mesenchyme, as demonstrated by different intestinal cell lineages (enterocytes, goblet cells, Paneth cells, tuft cells, and enteroendocrine cells) presence of functional brush-border enzymes (lactase, sucrose-isomaltase and diptidyl peptidase 4), and visible subepithelial and smooth muscle layers when compared with HIOs in vitro. Applicant has further shown that transplanted intestinal tissues demonstrated digestive functions as shown by permeability and peptide uptake studies. Transplanted HIO-derived tissue was found to be responsive to systemic signals from the host mouse following ileocecal resection, suggesting a role for circulating factors in the intestinal adaptive response.

Applicant further has developed a human PSC-derived intestinal tissue with a functional ENS. Using a tissue engineering approach with pluripotent stem cells (PSCs) to generate human intestinal tissue containing a functional ENS, Applicant has recapitulated normal intestinal ENS development by combining PSC-derived neural crest cells (NCCs) with developing human intestinal organoids (HIOs). When cultured alone, Applicant has found that NCCs had full differentiation potential in vitro, however when recombined with HIOs they differentiated into neurons and glial cells. NCC-derived ENS neurons were found to self-assemble within the developing intestinal mesenchyme and exhibited neuronal activity as measured by rhythmic waves of calcium transients. ENS-containing HIOs grown in vivo formed neuroglial structures similar to a myenteric and submucosal plexus, formed interstitial cells of Cajal, and had an electro-mechanical coupling that regulated waves of propagating contraction. This is the first demonstration of a human PSC-derived intestinal tissue with a functional ENS.

The enteric nervous system (ENS) is essential for GI motility, secretion, blood flow, epithelial barrier permeability and fluid exchange. Developmentally, the majority of the ENS arises from vagal neural crest cells (NCCs) that derive from the dorsal neural tube and migrate ventrally to colonize the foregut around embryonic week 4 in humans. Subsequently, the NCCs extensively proliferate and migrate caudally to colonize the entire GI tract by 7 weeks of human gestation. When enteric NCCs fail to properly migrate, proliferate, survive, and/or differentiate in the GI tract, defects in the structure and function of the ENS result and patients present with a spectrum of enteric neuropathies. In addition enteric neuropathies are common in digestive diseases such as inflammatory bowel disease and often occur secondarily in diseases such as Parkinson's disease, diabetes mellitus and age-related degeneration. The lack of human ENS model systems for studying physiopathological processes of enteric neuropathies may account for the surprisingly slow progress in their diagnosis and treatment. The long-standing treatment of patients with congenital lack of enteric ganglia, Hirschsprung's disease (1:5000 births), involves surgical resection of the aganglionic gut segment leaving a greatly reduced normal bowel. Although the remaining bowel contains ganglia, it remains unclear why many of these patients suffer from recurrent bouts of enterocolitis and dysmotily. Enteric neurons derived from pluripotent stem cells (PSCs), enteric progenitors, or even CNS neural stem cells have been shown to incorporate and function in aganglionic chick and murine GI explants, suggesting that a similar approach might work therapeutically in humans.

Despite the progress towards cell-based clinical treatments much work remains to be done regarding our understanding of human ENS development and disease. Very little is known about the etiology of enteric neuropathies, and mechanisms driving various aspects of human ENS development such as formation of neuronal diversity remain unclear. Although there is currently no way to functionally study human ENS development, recent progress using the directed differentiation of human pluripotent stem cells has resulted in the formation of complex and physiological 3D human organ cultures called organoids. Organoid models have been developed for intestine, liver, stomach, CNS, thyroid, and lung, to name a few, and have allowed for unprecedented studies of human developmental biology and disease. Despite the remarkable complexity of organoids, they lack cell and tissue types that are required for full organ function. For example, none of the organoid systems contain an integrated peripheral nervous system.

As disclosed herein, Applicant has demonstrated the development of 3D human intestinal organoids (HIOs) containing a functional eteric nervous system. PSCs were first differentiated into vagal-like neural crest cells (NCCs) and then introduced into developing intestinal cultures at the stage corresponding to gut tube formation to approximate normal colonization of the embryonic intestine by the ENS. The resulting HIOs could be grown in vitro >8 weeks, and resembled developing fetal intestine, with a diverse set of neurons capable of rhythmic and stimulated waves of calcium transients. When transplanted in vivo, HIOs formed complex, mature intestinal epithelium with crypts and villi surrounded by submucosal and myenteric smooth muscle layers. HIOs with an ENS formed both a submucosal and myenteric neuroglial plexus. The plexus contained bundles of neural cell bodies with a network of interganglionated fibers that integrated into the layers of smooth muscle. Electrical field stimulation of in vivo grown HIOs with an ENS elicited waves of propagating motility that were blocked with the neurotoxin tetrodotoxin. Organ-bath studies of tissue strips further demonstrated a functional nitrergic neuro-muscular coupling in HIOs with ENS. Thus, Applicant's invention is believed to be the first evidence for in vitro generation of human intestinal tissue with a functional enteric neural system fully derived from human pluripotent stem cells.

In one aspect, a method of making a vascularized hollow organ is disclosed. In this aspect, the method may comprise the steps of a) engrafting a human intestinal organoid (HIO) into an immune compromised organism, for example a mammal, for example a mammal having no immune response, for example a mammal having severe combined immunodeficiency disorder (SCID). The HIO may be obtained from human embryonic stem cells (ESCs) and/or induced pluripotent stem cells (iPSCs). In one aspect, during the engrafting step, the HIO forms mature intestinal tissue.

In one aspect, the human intestinal organoid (HIO) may be embedded in collagen. In one aspect, the collagen may be type I collagen.

The engrafting step may include transplantation of the HIO into a kidney capsule of an immune compromised organism. The engrafting step may be carried out for a period of at least about three weeks, or at least about four weeks, or at least about five weeks, or at least about six weeks. The duration of time with regard to this step may be determined by one of ordinary skill in the art. The engraftment step may be carried out, for example, until the intestinal tissue meets one or more criteria. Such criteria may include, for example, having a columnar intestinal epithelium surrounded by a supporting mesenchyme, growth of 1-3 cm in diameter, the formation of villi and crypts containing functional intestinal cells, having submucosal and myenteric layers of smooth muscle fibers, or a combinations thereof.

In one aspect, a method of making a human intestinal tissue containing a functional enteric nervous system (ENS) is disclosed. In this aspect, the method may comprise the steps of a) contacting vagal-like neural crest cells (NCCs) derived from human ES cells and/or iPS cells (IPCs) with a three dimensional human intestinal organoid (HIO); and c) transplanting said HIO in vivo. In one aspect, the NCCs may be obtained by contacting human ES cells and/or iPS cells with retinoic acid. In this aspect, the retinoic acid may be contacted with the human ES cells and/or iPS cells in an amount sufficient to cause posteriorization. In some aspects, the retinoic acid may be contacted with the human ES cells and/or iPS cells for a period of about 1 to about 2 days, or in some aspects, about 2 days. The retinoic acid contacting step may be carried out for a period of about two days at the neurosphere stage, or until substantial expression of HOXB3, HOXb5, and/or HOXb7 is observed.

In one aspect, the transplanting step may be carried out for a period of time sufficient to allow detection of neurons and/or glia. In one aspect, the neurons may comprise BIII-tubulin. In a further aspect, the glia comprise S100. In a yet further aspect, the neurons and glia may integrate into smooth muscle layers (desmin+cells). In one aspect, the transplanting step may be carried out for a period of time sufficient to allow formation of nNOS+ inhibitory neurons.

In one aspect, the human intestinal tissue containing a functional enteric nervous system (ENS) as described herein may be capable of contractile activity.

Further disclosed is a method of treating a patient requiring replacement of a portion of a gastrointestinal tract, which may comprise the step of replacing a portion of the patient's gastrointestinal tract with a human intestinal tissue manufactured according the methods as described herein. In a further aspect, disclosed is a method of determining the effect of a treatment on a human intestinal tract, comprising the step of contacting the treatment of interest with a human intestinal tissue manufactured according the methods as described herein. The model provided by Applicant may be useful for studies of intestinal physiology, disease, and/or translational studies.

EXAMPLE

Figure 1:
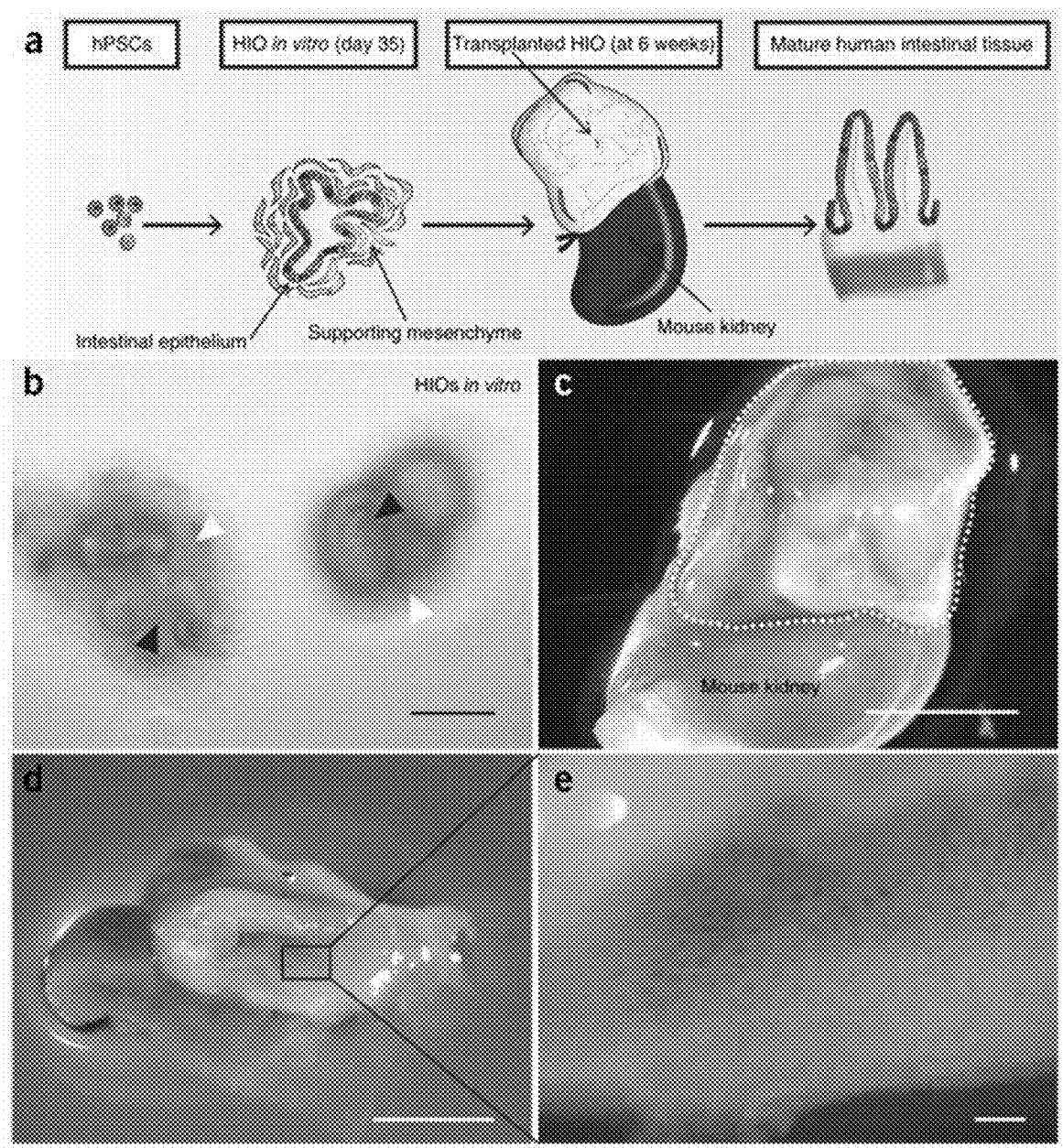
FIGS. 1A-E. HIOs engraft in vivo to form mature intestinal tissue.
Figure 2:
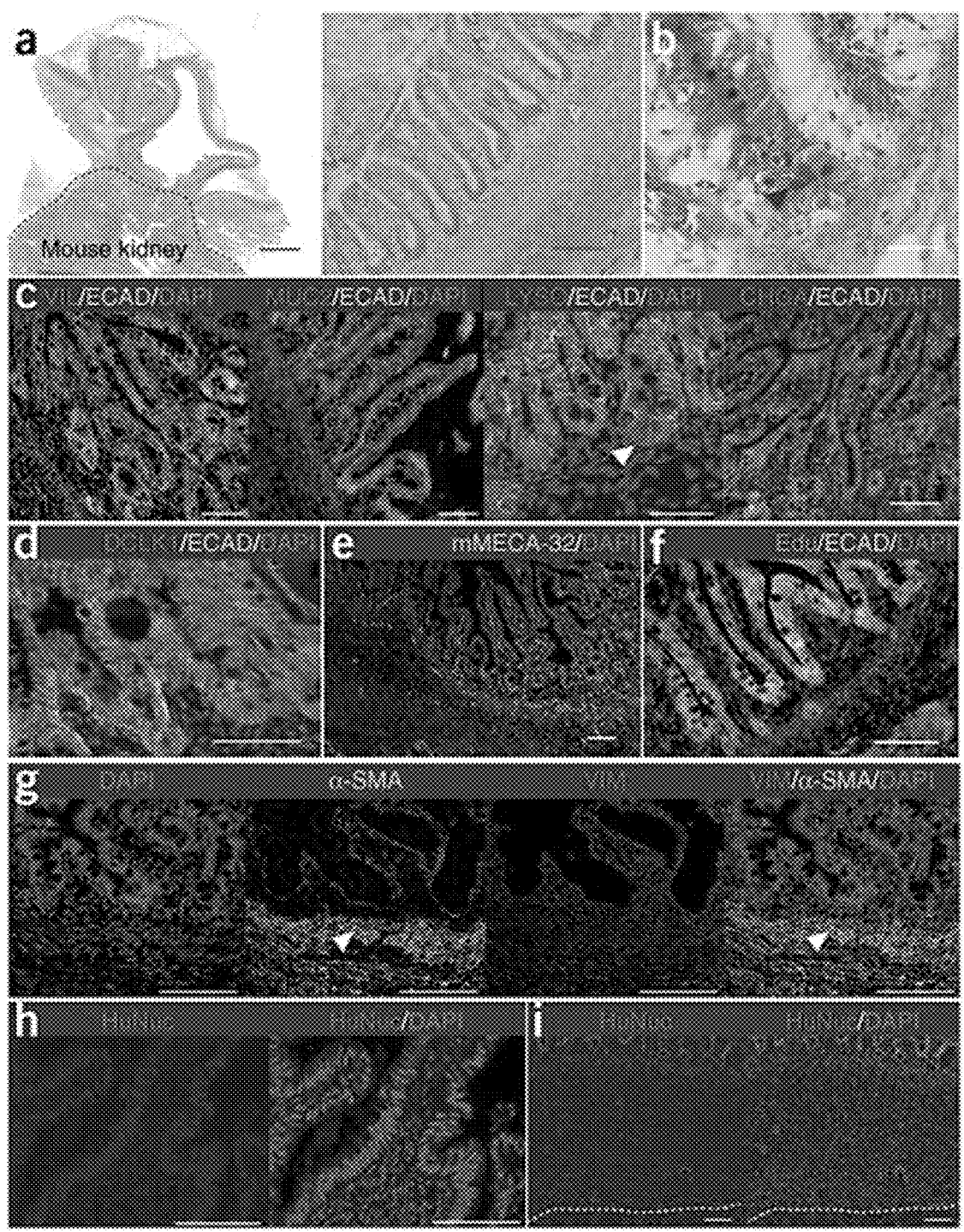
FIGS. 2A-2I. Engrafted intestinal tissue resembles adult intestine and is almost entirely of human origin.

Development of an in Vivo Model of Human Small Intestine Using Pluripotent Stem Cells To establish an in vivo HIO model, Applicant generated HIOs from human ESCs or iPSCs as previous described (Spence, et al, Nature 2011; McCracken et al, Nat. Protoc. 2011). The differentiation process took approximately 35 days. (FIG. 1A and FIG. 5A) and produced HIOs with columnar intestinal epithelium surrounded by a supporting mesenchyme (FIG. 1B and FIG. 5B). Applicant then embedded the HIOs into type I collagen and transplanted them under the kidney capsule of immunocompromised nonobese diabetic severe combined immunodeficiency interleukin-$2R\gamma^{null}$ (NSG) mice and allowed to mature and grow for six weeks (FIG. 1A and FIGS. 5D, 1E). At the time of harvest, the HIOs had grown considerably in size, upwards of 50- to 100-fold larger in volume (FIG. 1C, FIG. 1D and FIG. 5C and FIG. 6A) and were highly vascularized (FIG. 1C). Of note, 92.4% of the transplanted HIOs successfully engrafted under the kidney capsule (FIG. 5F). Visual inspection of tissues revealed intestinal morphology (FIG. 1D) with mucous-filled lumens and well-developed sheets of villi, each with its own central capillary network (FIG. 1E)). Histologically, this engrafted tissue resembled native human intestine with crypt-villus architecture and underlying laminated submucosal layers including lamina propria, muscularis mucosa, and submucosal and outer smooth muscle layers (FIG. 2A and FIG. 6C). When compared with their in vitro counterparts (data not shown), the engrafted tissue in vivo appeared more mature and differentiated, with all major intestinal cell lineages, including enterocytes, goblet cells, Paneth cells, eneroendocrine cells and tuft cells, located within appropriate regions of the crypt-villus axis (FIGS. 2B-D) and FIGS. 6D-G). Paneth cells were located within crypt bases as expected rather than scattered throughout the epithelium (FIGS. 2B, 2C). Transmission electron microscopy (TEM) revealed a brush border with well-developed tight junctions similar to that of HIOs in vitro (FIG. 7A); however, mature goblet cells and enteroendocrine cells, as seen within the epithelium of engraftments (FIGS. 7B,C), were not present in TEM of HIOs in vitro (data not shown). Within the epithelium, Applicant observed increased relative expression of genes characteristic of the epithelia cell types when comparing engraftments to HIOs in vitro (FIGS. 8A-G). Applicant found that blood vessels within the engraftment stained positive for mouse-specific panedothelial cell antigen (mMECA-32) (FIG. 2E). The engrafted tissue was also actively proliferating within discreet crypts, as revealed by incorporation of 5-ethanyl-2'-deoxyuridine (Edu) (FIG. 2F). Using transgenic human LGR5 reporter HIOs to trace intestinal stem cells, Applicant found that actively proliferating labeled stem cells were present within the HIOs and localized to the base of the crypts in the engraftment (FIGS. 9A-D). Additionally, the engrafted tissue expressed the stem cell marker ASCL2 (FIGS. 9E-F), and Applicant was able to generate enteroids derived from the epithelium of engraftments, further demonstrating the existence of an intestinal stem cell pool (FIGS. 9G-K). These data suggest that HIOs undergo considerable maturation into mature intestinal tissue following engraftment in vivo.

Cross-talk between the adjacent mesenchyme and intestinal epithelium is known to play a major role during GI development. It was previously shown that the supporting mesenchyme develops alongside the intestinal epithelium of HIOs in vitro and contains immature populations of subepithelial myofibroblasts, fibroblasts and smooth muscle cells. Applicant investigated whether HIO mesenchyme also developed into more mature, differentiated cell types following engraftment in vivo. The non-epithelial regions of the engrafted tissue stained positive for the mesenchymal marker vimentin (VIM) and included several laminated subepithelial layers, including distinct smooth muscle layers positive for α-smooth muscle actin (α-SMA), revealing the mesenchymal contribution of the engraftment (FIG. 2G). Additionally, dual staining for α-SMA and VIM revealed a pericryptal sheath (FIG. 2G) of intestinal subepithelial myofibroblasts (ISEMFs) which are known to support in vitro and in vivo growth of human small intestinal epithelial stem cells. Likewise, the intestinal epithelium has been shown to contribute appropriate signals for the development of the subepithelial mesenchymal layers including lamina propria, ISEMFs and muscularis mucosa leading to appropriate laminations of the subepithelium (FIGS. 2A,2G). In addition to the maturity of smooth muscle layers histologically, relative expression of desmin and α-SMA was increased in HIOs engrafted in vivo as compared to HIOs in vitro (FIGS. 8H, 8I). TEM of the engraftments revealed smooth muscle cells with parallel orientation similar to that of adult intestine (FIG. 7D). These data are consistent with published reports that successful engraftment and maturation of human intestinal tissues requires the presence of a mesenchymal niche. For example, lack of a mesenchymal component has resulted in failure of engraftment, whereas including mesenchymal cells along with epithelium resulted in successful engraftment.

As our engraftments contained a variety of mesenchymal cell types, including endothelial cells, Applicant next investigated which components were of human origin and which were from the host. As expected, HIO epithelium was completely of human origin and stained positive for a human nuclear antigen (HuNuc) (FIG. 2H). In addition, the majority of tissue of mesenchymal origin, including lamina propria, muscularis mucosa, submucosa and smooth muscle layers, also stained positive for HuNuc (FIG. 2I). In contrast, the majority of blood vessels were of mouse origin as they stained positive for mMECA-32 (FIG. 2E). The blood supply of the engrafted HIO was supported by mouse vasculature, as demonstrated by positive labeling of endothelium with FITC-conjugated tomato lectin tail vein injection (FIGS. 10A-10D). Few blood vessels of human origin were positive for human-specific panendothelial cell antigen in the engraftment, and these were not connected to the mouse vasculature (FIGS. 10E, 10F). Lymphatic vessels were of mouse origin and stained positive for mouse-specific lymphatic vessel endothelial hyaluronan receptor 1 (LYVE-1) (FIG. 10G).

Engraftment of PSC-derived pancreatic progenitor cells has been shown to enhance development of islet cells in vivo. Applicant analyzed the impact of in vivo growth on the maturity of our engraftments at 6 weeks as compared to HIOs in vitro at a similar time point (35 d plus 6 weeks in vitro) by determining the expression of several markers of mature epithelium at both the mRNA and protein levels. Applicant observed marked increases in mRNA and/or protein expression of markers characteristic of differentiated enterocytes, including dipeptidyl peptidase 4 (DPPIV), glucose transporter type 2 (GLUT2), sucrose-isomaltase (SIM) and villin (VIL), compared to HIOs in vitro (FIGS. 3A, 3B, 3E, 3F, 3A and FIGS. 8B, 8G). Additionally, Applicant also looked at the brush border enzymes alkaline phosphatase (ALPI) and lactase (LCT), as well as markers of secretory cell types, including enteroendocrine (gastric inhibitory peptide (GIP) and chromogranin A (CHGA)), goblet (mucin 2 (MUC2)) and Paneth cells (lysozyme (LYSO)). For each of these markers, there were also marked increases in mRNA and protein expression in engrafted HIOs (FIGS. 3C, 3D, 3G and FIGS. 8C-8F). Therefore, Applicant concluded that in vivo growth promotes maturation of the intestinal tissue.

Given the mature phenotype of engrafted HIOs in vivo, Applicant postulated that these tissues might represent a new model to study in vivo physiology of the human gut. Applicant therefore investigated whether engrafted HIOs could respond to physiologic cues elicited by intestinal resection. Humoral factors have been suggested to be involved in the intestinal adaptive response. In rats connected in a parabiotic relationship via vascular anastomosis, surgical resection in one rat led to increased intestinal proliferation in the parabiotic partner[7]. However, there is no model available to investigate this phenomenon with human intestine. Here, Applicant used a model of ileocecal resection (ICR) in the transplanted mice to investigate whether circulating humoral factors that are stimulated in response to intestinal resection could affect engrafted human intestinal tissues in the kidney. Applicant randomized mice with HIO engraftments at our 6-week time point following transplant to sham (transection and reanastomosis) or ICR groups and quantified morphometric factors associated with intestinal adaptation including crypt depth, villus height, epithelial proliferation, crypt fission and thickness of the circular and longitudinal smooth muscle layers (tunica muscularis) (FIG. 4A). Adaptation in NSG mice was confirmed with significant differences between sham and ICR groups for villus height, crypt fission (FIGS. 4B-4D), crypt depth and smooth muscle layer thickness (FIGS. 11A-11D), whereas there was no difference in proliferative index between sham and ICR groups (data not shown). In engrafted HIOs, ICR increased villus height, crypt fission (FIGS. 4E-4G and FIGS. 11E, 11F) and proliferative index (FIGS. 4H, I) compared to sham-operated groups. These findings support the hypothesis that engrafted HIOs respond to humoral factors. In addition, this model may provide insights into the humoral adaptive response following intestinal resection. Functionally, engrafted HIOs expressed active brush border enzymes and exhibited a functional intestinal epithelial barrier, as shown by a permeability assay with FITC-dextran (FIGS. 12A, 12B). The engrafted HIO epithelium was also capable of peptide uptake, reflecting the existence of absorptive functions (FIG. 12C).

To our knowledge, this is the first report of the development of a functional model for human small intestine in vivo derived from hPSCs. Our study highlights the potential of both ESCs and iPSCs to produce diverse cell types and tissue layers that mature following engraftment. Furthermore, the adaptive response seen in our human grafts following surgical resection in mouse hosts supports the role of humoral factors in this adaptive response and validates the use of our model for further in vivo studies of human small intestine. HIOs may also serve, through further translational research, as a means for the eventual treatment of short bowel syndrome and other gastrointestinal diseases, as they serve as a way to 'personalize' and bioengineer functional human intestine.

Methods

Animals

Immune-deficient NOD-SCID IL-2Rγnull (NSG) mice, 8-16 weeks old, were used in all experiments (obtained from the Comprehensive Mouse and Cancer Core Facility, Cincinnati, Ohio). All mice were housed in the animal facility at the Cincinnati Children's Hospital Medical Center (CCHMC). All experiments were performed with the approval of the Institutional Animal Care and Use Committee of CCHMC.

Generation and Maintenance of Human Intestinal Organoids

Human intestinal organoids were generated and maintained as previously described (Spence et al, Nature 2011 and McCracken et al. Nat. Protoc. 2011). Human embryonic stem cells and induced pluripotent stem cells were grown in feeder-free conditions in six-well Nunclon surface plates (Nunc) coated with Matrigel (BD Biosciences) and maintained in mTESR1 media (Stem Cell Technologies). For induction of definitive endoderm (DE), human ES or iPS cells were passaged with Dispase or Accutase (Invitrogen) and plated at a density of 100,000 cells per well in a Matrigel-coated, Nunclon surface 24-well plate. For Accutase split cells, 10 µM Y27632 compound (Sigma) was added to the media for the first day. Cells were allowed to grow until they reached 80-95% confluence. Cells were then treated with 100 ng ml-1 of Activin A for 3 d as previously described (D'Amour et al. Nat. Biotechnol. 2005). DE was then treated with hindgut induction medium (RPMI 1640, 2 mM L-glutamine, 2% decomplemented FBS, penicillin-streptomycin and 100 ng ml-1 Activin A) for 4 d with 500 ng mL-1 FGF4 (R&D) and 3 µM Chiron 99021 (Tocris) to induce formation of mid-hindgut spheroids. Spheroids were then plated in Matrigel (BD) and maintained in intestinal growth medium (Advanced DMEM/F-12, N2, B27, 15 mM HEPES, 2 mM L-glutamine, penicillin-streptomycin) supplemented with 100 ng ml-1 EGF (R&D) and 100 ng ml-1 Noggin (R&D) to generate human intestinal organoids (HIOs). Media was changed at 3 d with Noggin removed and then changed twice weekly thereafter. HIOs were replated in fresh Matrigel every 14 d.

Generation and Characterization of Induced Pluripotent Stem Cell Lines

For iPSC generation, fibroblasts were transduced with recombinant VSV-G—pseudotyped polycistronic lentiviral particles co-expressing reprogramming factors Oct4, Klf4, Sox2, cMyc and dTomato28. Nucleofected fibroblasts were then plated on hESC-qualified Matrigel, and 3-5 d post transduction, MEF media was replaced with mTeSR1, and cultures were subsequently fed daily with mTeSR1. After ~3 weeks, putative iPSC colonies were identified and exposed to dispase for 5 min. Discrete colonies were manually excised and replated in mTeSR1 on Matrigel-coated dishes. Several lines with typical hESC-like morphology were then expanded independently in mTeSR1 on Matrigel-coated dishes. For passaging, iPSCs were exposed to dispase for 5 min, washed, and gently triturated before replating. iPSC lines were cryopreserved in mFreSR (StemCell Technologies). All cultures were maintained in a 5% CO2/air environment. All the experiments with iPSCs in this study were approved by institutional Embryonic Stem Cell Research Oversight (ESCRO).

For analysis of pluripotency marker expression, iPSC cultures were fixed for 10 min at room temperature with 3.7% paraformaldehyde in PBS. Cells were then permeabilized for 10 min with PBS containing 0.5% Triton X-100 and incubated for 30 min at room temperature in blocking buffer (10% normal donkey serum in PBS). Antibodies to human Oct4 (Santa Cruz, sc-5279) and Nanog (Abcam, ab21624) were diluted in blocking buffer at 1:500 and incubated with cells overnight at 4° C. After incubation with fluorescent-labeled secondary antibodies, cultures were visualized using fluorescent microscopy. 4',6-diamidino-2-phenylindole (DAPI) was used for nuclear counterstaining (FIGS. 13A, 13B). Standard G-banded karyotype analyses of iPSCs was performed by the Cytogenetics Laboratory at Cincinnati Children's Hospital Medical Center. At least 20 metaphases were analyzed (FIG. 13C). Analysis of in vivo differentiation capacity was assessed with teratoma assays. Undifferentiated iPSCs were injected subcutaneously into immune compromised NOD/SCID GAMMA C$^{-/-}$ mice. Teratomas formed within 6-12 weeks. Teratomas were excised, fixed, embedded in paraffin, sectioned and stained with H&E for histological examination (FIG. 13D).

Generation of LGR5:eGFP BAC Transgenic Reporter hESC Line

The LGR5: eGFP bacterial artificial chromosome (BAC) transgenic reporter hESC line was generated. In summary, the BAC RP11-59F15 was obtained from the Children's Hospital Oakland Research Institute (http://bacpac.chori.org/) and grown in SW10535 cells. A single colony was expanded in LB+cam at 32° C., and recombineering proteins were induced by incubation at 42° C. for 20 min. The recombination cassette consisted of eGFP-FRT-PGKgb2-neo/kan-FRT, 50-bp homology region in LGR5, and a 20-bp homology region to peGFP-PGKneo. The homology regions were selected to replace the initiator methionine of LGR5 with that of eGFP followed by a bovine growth hormone polyadenylation signal and FRT-flanked bifunctional kanamycin/G418 resistance cassette. The recombination cassette was electroporated into SW105 cells, and cells were selected on plates with cam and kanamycin (kan; 50 µg ml-1). Clones were analyzed for properly targeted LGR5 BAC by PCR and confirmed by sequencing and nucleofected into single-cell suspensions of H9 hESCs using the Amaxa Human Stem Cell Nucleofector Starter Kit. Cells were selected in G418 (200 ng ml-1) for 2 weeks. G418-resistant cells were maintained in antibiotic indefinitely.

Transplantation of Human Intestinal Organoids

NSG mice were kept on antibiotic chow (275 p.p.m. Sulfamethoxazole and 1,365 p.p.m. Trimethoprim; Test Diet). Food and water was provided ad libitum before and after surgeries. A single HIO, matured in vitro for 35 d, was removed from Matrigel, washed with cold phosphate-buffered saline (DPBS; Gibco), and embedded into purified type I collagen (rat tail collagen; BD Biosciences) 12 h before surgery to allow for formation of a solidified gel plug. These plugs were then placed into standard growth media overnight in intestinal growth medium (Advanced DMEM/F-12, B27, 15 mM HEPES, 2 mM L-glutamine, penicillin-streptomycin) supplemented with 100 ng ml-1 EGF (R&D). HIOs were then transplanted under the kidney capsule. Briefly, the mice were anesthetized with 2% inhaled isoflurane (Butler Schein), and the left side of the mouse was then prepped in sterile fashion with isopropyl alcohol and povidine-iodine. A small left-posterior subcostal incision was made to expose the kidney. A subcapsular pocket was created and the collagen-embedded HIO was then placed into the pocket. The kidney was then returned to the peritoneal cavity and the mice were given an IP flush of Zosyn (100 mg/kg; Pfizer Inc.). The skin was closed in a double layer and the mice were given a subcutaneous injection with Buprenex (0.05 mg/kg; Midwest Veterinary Supply). At 6 weeks following engraftment, the mice were then humanely euthanized or subjected to further experimentation.

Intestinal Resections in Transplanted Mice

Male NSG mice that have previously been transplanted with HIOs 6 weeks prior were randomized to ileocecal resection (ICR) or sham operation. Mice were placed on liquid diet (Jevity 1Cal; Abbott) 24-48 h before surgery and were changed from antibiotic chow to liquid antibiotic (200 mg Sulfamethoxazole and 40 mg Trimethoprim oral suspension 5 mL-1; Hi-Tech Pharmacal) in their drinking water (0.3 mg mL-1 Trimethoprim) for the remainder of the experiment. Surgeries were completed under anesthesia as described above, and the abdomen of the mouse was opened anteriorly to expose the intestine. An average of 13.6 cm of distal-most small intestine was removed in addition to the cecum as previously described 26. Mice were kept in an incubator at 30° C. for 48 h after surgery and were then euthanized on post-operative day 7.

Culture of Transplant-Derived Enteroids

Human enteroids were generated as previously described 12,29. Briefly, engraftments were harvested and opened and pinned with mucosa facing upwards and then rinsed in cold PBS (Gibco). The tissues were then transferred to 2 mM EDTA (EDTA; Sigma-Aldrich) in PBS and rocked for 30 min on ice. After EDTA chelation, tissues were again washed in cold PBS, and crypts were manually removed from underlying submucosa and then filtered through a 100-μm cell strainer (Fisher Scientific). Crypts were then pelleted and resuspended in Matrigel (BD Biosciences) and overlaid with intestinal growth medium (Advanced DMEM/F-12, N2, B27, 15 mM HEPES, 2 mM L-glutamine, penicillin-streptomycin) supplemented with EGF (50 ng mL-1), Noggin (100 ng mL-1), R-spondin 1 (1 μg mL-1) (R&D Systems), 50% Wnt3a conditioned medium, 1 mM N-acetylcysteine, 10 nM (Leu15)-Gastrin, 10 mM Nicotinamide, 10 μM SB202190 (Sigma-Aldrich), 500 nM A-83-01 (Tocris). 2.5 μM Thiazovivin and 2.5 μM CHIR99021 (Stemgent) were added to the medium for the first 2 d. Medium was changed every 3 d. Established enteroids were passaged over time by enzymatic (TrypLE Express, Life Technologies) and mechanical dissociation through an 18-gauge needle after 7 d in culture. Dissociated enteroids were then resuspended in PBS and pelleted before resuspension in Matrigel and culture conditions as above.

Intestinal Alkaline Phosphatase Activity

Frozen sections were washed in PBS and blocked using donkey serum. Sections were incubated with Permanent Red working solution (Permanent Red substrate+Permanent Red chromogen; Dako) for 30 min at room temperature. Sections were then washed in PBS and mounted for imaging.

In Vivo FD4 Permeability Assay

FITC-conjugated dextran (FD4; 4,400 MW; Sigma) was dissolved in sterile water at a final concentration of 20 mg ml-1. Mice with previous transplants 8 weeks prior were then anesthetized as described above, and a left, posterior subcostal incision was made to expose the left kidney and engrafted intestinal tissue. Human engraftments were then injected each with 100 μL of FD4. Whole blood was then collected using heparinized hematocrit capillary tubes at time points 30 min and 4 h post-injection, and fluorescence intensity in murine sera was analyzed using a fluorescent plate reader. The concentration of FITC-dextran was then determined by comparison to the FITC-dextran standard curve dissolved in water.

In Vivo Tomato Lectin Injections

Fluorescein Lycopersicon esculentum (tomato) lectin (Vector laboratories) was resuspended in PBS at a final concentration of 2 mg ml-1. 8 weeks after HIO transplantation, mice were placed under anesthesia as described above and were each injected with 200 μl of the tomato lectin via the tail vein. Mice were then humanely euthanized 30 min following injection, and tissues were collected for imaging.

In Vivo D-Ala-Leu-Lys-AMCA Uptake Study

D-Ala-Leu-Lys-7-amido-4-methylcoumarin (D-Ala-Leu-Lys-AMCA; Sigma) was prepared as previously described 30 with modification for a final concentration of 25 μM solution in DMEM (Dulbecco's Modified Eagle Medium; Gibco). Mice were anesthetized as described above and a left posterior subcostal incision was created to expose the engraftment. The engraftment lumen was then injected with 100 μL of D-Ala-Leu-Lys-AMCA, and mice were closed in a double-layer fashion. Mice were euthanized 30 min post-injection, and tissue was collected for analysis. For comparison, engraftments were also injected with vehicle (DMEM solution) alone or with peptide solution mixed with 1 mM Captopril (Sigma), a competitive inhibitor of peptide uptake.

Tissue Processing, Immunofluorescence and Microscopy

Tissues were fixed for 2 h to overnight in 4% paraformaldehyde (PFA). Organoid engraftments were frozen in OCT, whereas mouse intestinal tissues were embedded in paraffin. OCT sections were blocked using donkey serum (10% serum in 1×PBS plus 0.5% Triton-X) for 30 min and incubated with primary antibody overnight at 4° C. Slides were then washed and incubated in secondary antibody in blocking buffer for 2 h at room temperature (23° C.). Paraffin sections were deparaffinized, subjected to antigen retrieval, and stained in a similar fashion to OCT sections. Please see Table 1 for a list of antibodies and respective dilutions. Slides were then washed and mounted using ProLong Gold antifade reagent with DAPI (Life Technologies). Images were captured on a Nikon Eclipse Ti and analyzed using Nikon Elements Imaging Software (Nikon). For transmission electron microscopy (TEM), tissues were fixed overnight in 3% glutaraldehyde in 0.175 M sodium cacodylate buffer pH 7.4. Samples were then post fixed in 1% Osmium tetroxide in 0.175 M cacodylate buffer for 1 h at 4° C. Samples were washed and put through a series of graded ethanol (25, 50, 75, 95, 2×100%). Infiltration was performed with 2× Propylene Oxide followed by graded infiltration with LX-112. Samples were placed in polymerization oven at 37° C. overnight and then kept at 60° C. for 3 d. A Hitachi H7600 transmission electron microscope was used to image TEM sections. For whole-mount staining, tissues were processed similarly as above and then cleared in Murray's solution. Imaging was performed with a Nikon A1 confocal microscope.

TABLE 1

List of primary and secondary antibodies used for immunostaining.

| Provider | Label | Host | Reactivity | Name | Cat. Number | Dilution |
|---|---|---|---|---|---|---|
| Primary Ab | | | | | | |
| Abcam | | Goat | Mouse, Human | Vimentin (VIM) | ab11256 | 1:500 |
| Sigma | | Mouse | Human | aplha SMA (α-SMA) | Ab8207 | Prediluted |
| R&D | | Goat | Mouse, Human | E-cadherin (Ecad) | AF648 | 1:500 |

TABLE 1-continued

List of primary and secondary antibodies used for immunostaining.

| Provider | Label | Host | Reactivity | Name | Cat. Number | Dilution |
|---|---|---|---|---|---|---|
| R&D | | Rat | Mouse, Human | E-cadherin (Ecad) | MAB 7481 | 1:500 |
| Dako | | Rabbit | Human | Lysozyme (Lyz) | A0099 | 1:1000 |
| Immunostar | | Rabbit | Mouse, Human | Chromogranin A (ChgA) | 20085 | 1:500 |
| Santa-Cruz | | Rabbit | Mouse, Human | Mucin 2 (MUC2) | sc-15334 | 1:200 |
| Millipore | Cy 3 | Mouse | Human | Human Nuclear (HuNuc) | MAB 1281C3 | 1:500 |
| Biogenex | | Mouse | Human | CDX2-88 (CDX2) | AM392 | 1:300 |
| Sigma | | Rabbit | Human | Lactase-gycosylceramidase (LCT) | HPA007408 | 1:500 |
| Novus Biologicals | | Rat | Mouse | MECA-32 | NB100- | 1:500 |
| Santa-Cruz | | Goat | Mouse, Human | Gastric Inhibitory Peptide (GIP) | 77668 | 1:500 |
| Santa-Cruz | | Goat | Mouse, Human | Villin | sc-23554 | 1:100 |
| R&D | | Goat | Mouse, Human | DPPIV | sc-7672 | 1:500 |
| DSHB | | Mouse | Human | Sucrase-Isomaltase (SIM) | AF954 | 1:500 |
| eBioscience | eF 660 | Rat | Mouse | Lyve-1 | HBB2/614/88 | 1:500 |
| Santa-Cruz | | Rabbit | Mouse, Human, Rat | Peptide Transporter 1 (Pept1) | 50-0443 | 1:500 |
| Millipore | FITC | Mouse | Human | Achaete Scute homolog 2 (ASCL2) | Sc-20653 | 1:20 |
| Pierce Thermo | | Mouse | Human | CD31/PECAM-1 | FCMAB285F | 1:500 |
| Secondary Ab | | | | | MA5-15336 | |
| Invitrogen | AF488 | Donkey | Goat | Goat IgG | | 1:500 |
| Invitrogen | AF555 | Goat | Rabbit | Rabbit IgG | A11055 | 1:500 |
| Invitrogen | AF488 | Donkey | Rat | Rat IgG | A21428 | 1:500 |
| Invitrogen | AF488 | Donkey | Rabbit | Rabbit IgG | A21208 | 1:500 |
| Invitrogen | AF546 | Donkey | Mouse | Mouse IgG | A21206 | 1:500 |
| Invitrogen | AF647 | Donkey | Goat | Goat IgG | A10036 | 1:500 |
| Invitrogen | AF555 | Goat | Mouse | Mouse IgG2a | A21447 | 1:500 |
| Invitrogen | AF546 | Donkey | Rabbit | Rabbit IgG | A21137 | 1:500 |
| Invitrogen | AF555 | Donkey | Goat | Goat IgG | A10040 | 1:500 |
| Invitrogen | AF488 | Rabbit | Goat | Goat IgG | A21432 | 1:500 |
| Invitrogen | AF488 | Donkey | Mouse | Mouse IgG | A11078 | 1:500 |
| Invitrogen | AF568 | Donkey | Mouse | Mouse IgG | A21202 | 1:500 |
| Jackson-Imm. | Cy5 | Goat | Rat | Rat IgG | A10037 | 1:500 |

RNA Isolation and RT-qPCR

RNA was extracted using RNeasy Plus Mini Kit (Qiagen) according to manufacturer's protocols. A cDNA reverse transcription kit (Applied Biosystems) was used to synthesize cDNA. Taqman (Applied Biosystems) gene expression assays were then performed on triplicate samples using a OneStep cycler (Applied Biosystems). See Table 2 for a list of Taqman probes used.

TABLE 2

List of Human Taqman ® Probes used for RT-PCR.

| Human TaqMan ® Probes | | Gene ID | TaqMAN # | Accession # | Amplicon Length (bp) | Maker type |
|---|---|---|---|---|---|---|
| Gene | Gene Name | | | | | |
| ALPI | Alkaline Phosphatase, intestinal | 248 | Hs00357579_g1 | NM_001631.3 | 56 | Enterocyte |
| CHGA | Chromogranin A | 1113 | Hs00900375_m1 | NM_001275.3 | 88 | Enteroendocrine cell |
| LYZ | Lysozyme | 4069 | Hs00426232_m1 | NM_000239.2 | 67 | Paneth cell |
| MUC2 | Mucin 2 | 4583 | Hs03005103_g1 | NM_002457.2 | 53 | Goblet cell |
| EpCAM | Epithelial Cell Adhesion Molecule | 4072 | Hs00901885_m1 | NM_002354.2 | 95 | Epithelium/ Enterocyte |

TABLE 2-continued

List of Human Taqman ® Probes used for RT-PCR.

| Human TaqMan ® Probes | | | | | Amplicon Length | |
|---|---|---|---|---|---|---|
| Gene | Gene Name | Gene ID | TaqMAN # | Accession # | (bp) | Maker type |
| VIM | Vimentin | 7431 | Hs00185584_m1 | NM_003380.3 | 73 | Mesenchyme/ Fibroblast |
| ACTA2 | alpha-2, Smooth muscle actin | 59 | Hs00426835_g1 | NM_001141945.1 | 105 | Smooth Muscle |
| DES | Desmin | 1674 | Hs00157258_m1 | NM_001927.3 | 83 | Fibroblasts/ Smooth |
| SI | Sucrase-Isomaltase (alpha-glucosidase) | 6467 | Hs00356112_m1 | NM_001041.3 | 64 | Enterocyte |
| VILL | Villin-like | 50853 | Hs00210626_m1 | NM_015873.3 | 74 | Enterocyte |
| DPP4 | Dipeptidyl-peptidase 4 | 1803 | Hs00175210_m1 | NM_001935.3 | 90 | Enterocyte |
| SLC2A2 | Facilitated Glucose Transporter 2 (GLUT 2) | 6514 | Hs01096908_m1 | NM_000340.1 | 65 | Enterocyte |
| GIP | Gastric Inhibitory Polypeptide | 2695 | Hs00175030_m1 | NM_004123.2 | 78 | Proximal |
| LCT | Lactase | 3938 | Hs00158722_m1 | NM_002299.2 | 79 | Enterocyte |

Morphometric and Statistical Analyses

Histological sections were stained with hematoxylin and eosin or subjected to immunohistochemistry (as described above). All histological samples were counted in a blinded manner. Crypt depth, villus height, and smooth muscle layer (tunica muscularis) thickness were measured for a minimum of 100 well-oriented crypt-villus units or smooth muscle layer segments per mouse and then averaged using Nikon NIS imaging software. Crypt fission was also calculated in a similar manner using longitudinal sections to determine the percentage of fissioning crypts from at least 100 intact crypts per animal. A fissioning crypt is defined as a bifurcating crypt with a bisecting fissure creating two (or sometimes more) flask-shaped bases with a shared single crypt-villus junction (FIGS. 23 A, F). Proliferative index was determined by injecting mice with 5-ethynyl-2'-deoxyuridine (Edu) 2 h before killing, and then, following routine Edu immunohistochemistry according to manufacturer's instructions, proliferative index was determined by calculating the ratio of Edu-positive cells to total cells within at least 10 intact crypts. All data are represented as mean±s.e.m. t-tests and two-way analysis of variance were completed using Prism (GraphPad). The determined significance cutoff was $P<0.05$. No statistical method was used to predetermine sample size.

The experiments were not randomized except ICR experiments, where transplanted animals were randomly assigned to a sham or an ICR group. The investigators were not blinded to allocation during experiments and outcome assessment except for the morphometric analysis for the ICR experiments.

Example

Development of Tissues with a Functional Enteric System

Generation of Vagal Neural Crest Cells

Cranial and trunk (both vagal and sacral) NCCs emanate from discrete regions along the A-P axis, and colonize different regions of the developing embryo. The ENS, for example, derives from vagal NCCs. Therefore, to generate human intestinal organoids with an ENS, Applicant hypothesized that vagal NCCs would be a more appropriate starting source. Given that numerous methods have been reported to direct the differentiation of PSCs into cranial NCCs 9,10, Applicant first started by generating cranial NCCs in stepwise manner that mimics normal NCC development (FIG. 1, FIG. 20). As previously reported, cranial NCCs derived from PSCs expressed stage-specific molecular markers in a manner similar to cranial NCCs during embryonic development including Sox2, Pax3, and Pax7 at early neuroepithelial stages and HNK-1, Sox10, Snail2 and vimentin in migrating neural crest cells.

To generate vagal NCCs, which come from more posterior regions of the neural tube, Applicant manipulated signaling pathways that are known to promote a posterior fate at early stages during the differentiation process. Applicant found that retinoic acid (RA), but not FGF4 (data not shown), for two days at the neurosphere stage resulted in the robust expression of the vagal-level Hox genes HOXB3, HOXB5, and HOXB7 (FIG. 14D), similar to the observations by Mica et al. Applicant confirmed that the posterior Hox gene hoxb7 was expressed in trunk/vagal NCCs isolated from chick embryos (FIGS. 21A and 21B). Moreover, RA was able to induce vagal Hox gene expression in chick cranial NCCs (FIG. 21C), consistent with the known role of RA in patterning of vagal NCCs during vertebrate development.

Differentiation Potential of Neural Crest Cells

Multipotent NCCs can form ectoderm derivatives including neurons, glia, and melanocytes as well as cranial mesodermal lineages including osteocytes and chondrocytes. To test whether NCCs retained multipotent differentiation potential, Applicant directed differentiations of NCCs towards various ectomesenchymal lineages in vitro (FIG. 22A). NCCs were able to differentiate into Peripherin+ neurons and GFAP+ glial cells in vitro upon growth factor withdraw. PSC-derived NCCs could also be differentiated into mesoderm lineages including osteocytes and chondrocytes as indicated by positive staining for alizarin red and alcian blue, respectively. Applicant did not observe any gross differences of RA treatment on the in vitro differentiation potential of NCCs suggesting that the mulitpotency of PSC-derived cranial and vagal/Hox-positive NCC populations had been maintained. Applicant further tested if PSC-derived NCCs had neural crest cell behaviors in an embryonic context by injecting them into chick embryos. PSC-derived NCCs followed a migratory path similar to endogenous NCCs and differentiated into neurons (FIGS. 21D-21F).

Generating Human Intestinal Organoids (HIOs) with NCC-Derived Neuroglial Cells in Vitro Applicant previously developed a method to differentiate human PSCs into intestinal organoids following a stepwise differentiation first into definitive endoderm, then into mid/hindgut tube spheroids that are expanded into 3D intestinal tissue (Spence et al., McCracken et al. (FIG. 23). In vitro, HIOs contain all major intestinal epithelial cells types, as well as a stratified mesenchyme containing subepithelial myofibroblasts and smooth muscle cells. When HIOs are engrafted into the kidney subcapsular space they continue to develop and form highly differentiated intestinal tissue with crypts and villi, functional intestinal stem cells, and layers of smooth muscle (FIG. 23B).

While HIOs contained most of the epithelial and mesenchymal cell types found in the developing gut, they did not contain an ENS. To incorporate NCCs/ENS precursors into developing HIOs, Applicant mechanically aggregated mid/hindgut spheroids with PSC-derived NCCs by low speed centrifugation and transferred aggregates to 3 dimensional growth conditions for 28 days (FIG. 15A). HIOs with and without NCCs were comparable in size (1-2 mm in diameter), however Applicant detected an abundance of βIII-tubulin (TUJ1)+ neurons and S100+ glia embedded within the mesenchyme of HIOs combined with NCCs (FIG. 15B). Applicant rarely detected neurons and never glia in HIOs without NCCs in vitro. Moreover Applicant confirmed the NCC origin of neuroglial cells by using NCCs that were derived from a PSC line that constitutively expressed GFP (FIG. 24). The spatial relationship between the epithelium, mesenchyme and neuroglial cells in HIOs+NCCs closely resembled that of human fetal intestine and E11.5 mouse small intestine (data not shown), suggesting that intrinsic cues in HIOs help organize the developing ENS cells. Consistent with this, HIOs expressed both GDNF and EDN3, two critical chemoattractants known to regulate NCC migration into the gut mesenchyme (FIG. 23C), suggesting that incorporation of PSC-derived NCCs into HIO mesenchyme may have utilized normal developmental pathways.

Maturation of the ENS Following in Vivo Growth

Our previous studies have demonstrated that HIOs that are engrafted into mice and allowed to grow for 6-10 weeks in vivo become vascularized, grow to 1-3 cm in diameter, and form highly mature intestinal tissues with villi and crypts containing functional intestinal stem cells as described above and in Watson et al 2011 (FIG. 17B). Moreover the HIO mesenchyme matures into submucosal and myenteric layers of smooth muscle fibers (FIG. 15C). Analysis of transplanted HIOs+PSC-derived NCCs revealed that neurons (βIII-tubulin) and glia (S100) were organized into multiple layers in proximity to the submucosal and myenteric layers of smooth muscle (FIG. 15C). Applicant did not detect neurons or glia in transplanted HIOs without NCCs. While these experiments were performed with vagal/HOX-positive NCC populations, PSC-derived cranial/HOX-negative NCCs were also competent to engraft and form ENS neuroglial cells. However cranial NCCs also formed pigmented epithelial cells (FIG. 22B) and cartilage (not shown) consistent with them having a broader multipotency.

Neuronal Diversity and Function in HIOs+NCCs

Figure 3:
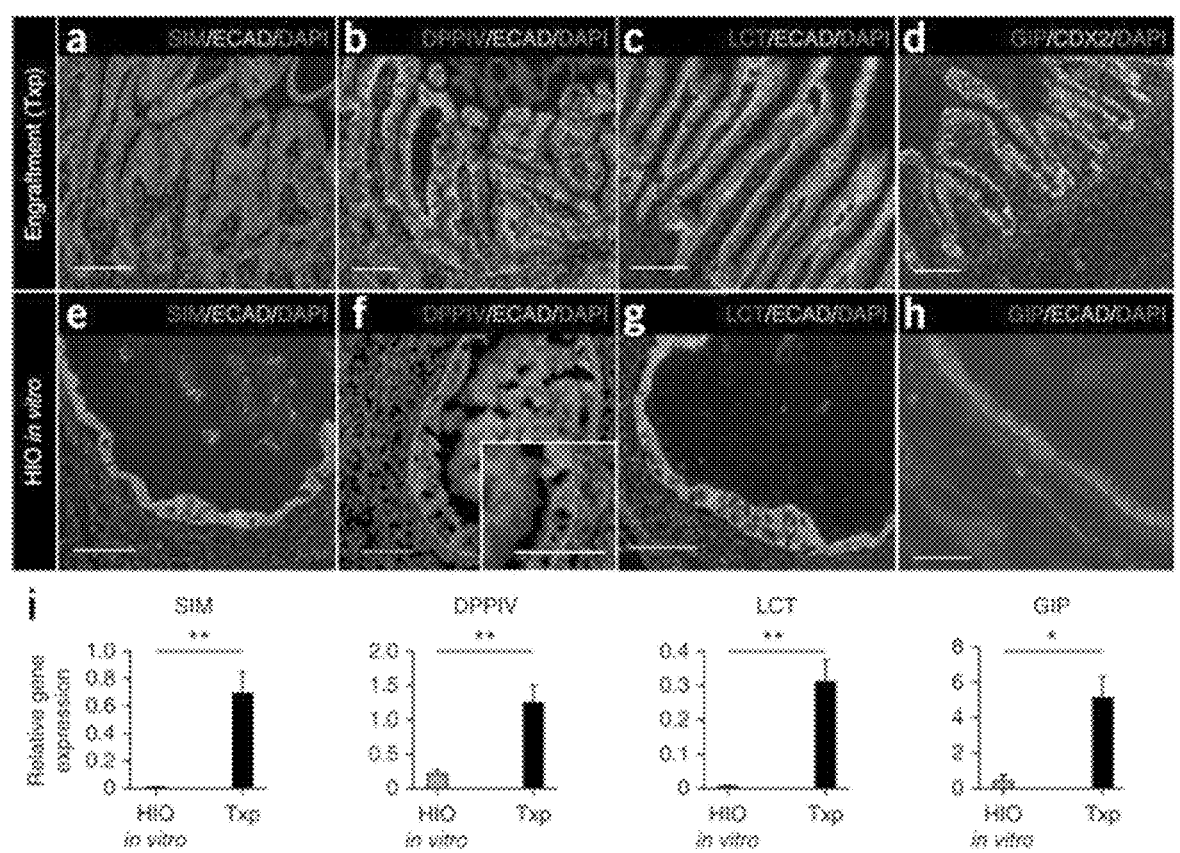
FIGS. 3A-I. Engrafted tissue matures in vivo and resembles mature small intestine.

The ENS is a complex network of excitatory and inhibitory neuronal subtypes, as well as interneurons. Examination of neural markers in HIOs+NCCs cultured in vitro for four weeks suggested a significant degree of neuronal diversity. Applicant observed tyrosine hydroxylase (TH), calbindin, calretinin, and serotonin (5-HT) positive cells, which are expressed by dopaminergic, excitatory and interneurons (FIG. 3A). However Applicant did not detect nNOS positive neurons in vitro. In contrast, in vivo transplanted HIOs+NCCs had an abundance nNOS+ neurons suggesting that the ENS matured during the period of in vivo growth. Many neurons appear to be associated with smooth muscle in transplanted HIOs+NCCs. Moreover, ENS neurons were associated with cells expressing CD117, a marker of interstitial cells of Cajal (ICCs) (FIG. 16B). While ICCs were present in HIOs lacking an ENS, there appeared to be fewer clusters of CD117-expressing cells in HIO−NCCs (data not shown), suggesting a developmental interaction between ENS cells and ICCs.

The accessibility of in vitro grown HIOs allowed us to test the functionality of neurons using live imaging with the Ca2+ sensor GCaMP6f19. To do this, Applicant generated HIOs and incorporated into them NCCs that were derived from a PSC line containing GCaMP6 (FIG. 17A). Imaging of neural activity in HIOs grown for 8 weeks in vitro detected broad, spontaneous, and rapid calcium transients within neurons. When individual neurons were monitored there was an obvious periodicity of calcium efflux in the range of 3-4 seconds/neuron (FIGS. 17B and 17C). To test if neurons were capable of undergoing coordinated activity Applicant exposed HIOs+GCaMP6 expressing NCCs to KCl (30 mM) and observed a large wave of neuronal calcium efflux (FIG. 17D).

Neuroglial Plexus Formation in HIO+NCCs Grown In Vivo.

Figure 18:
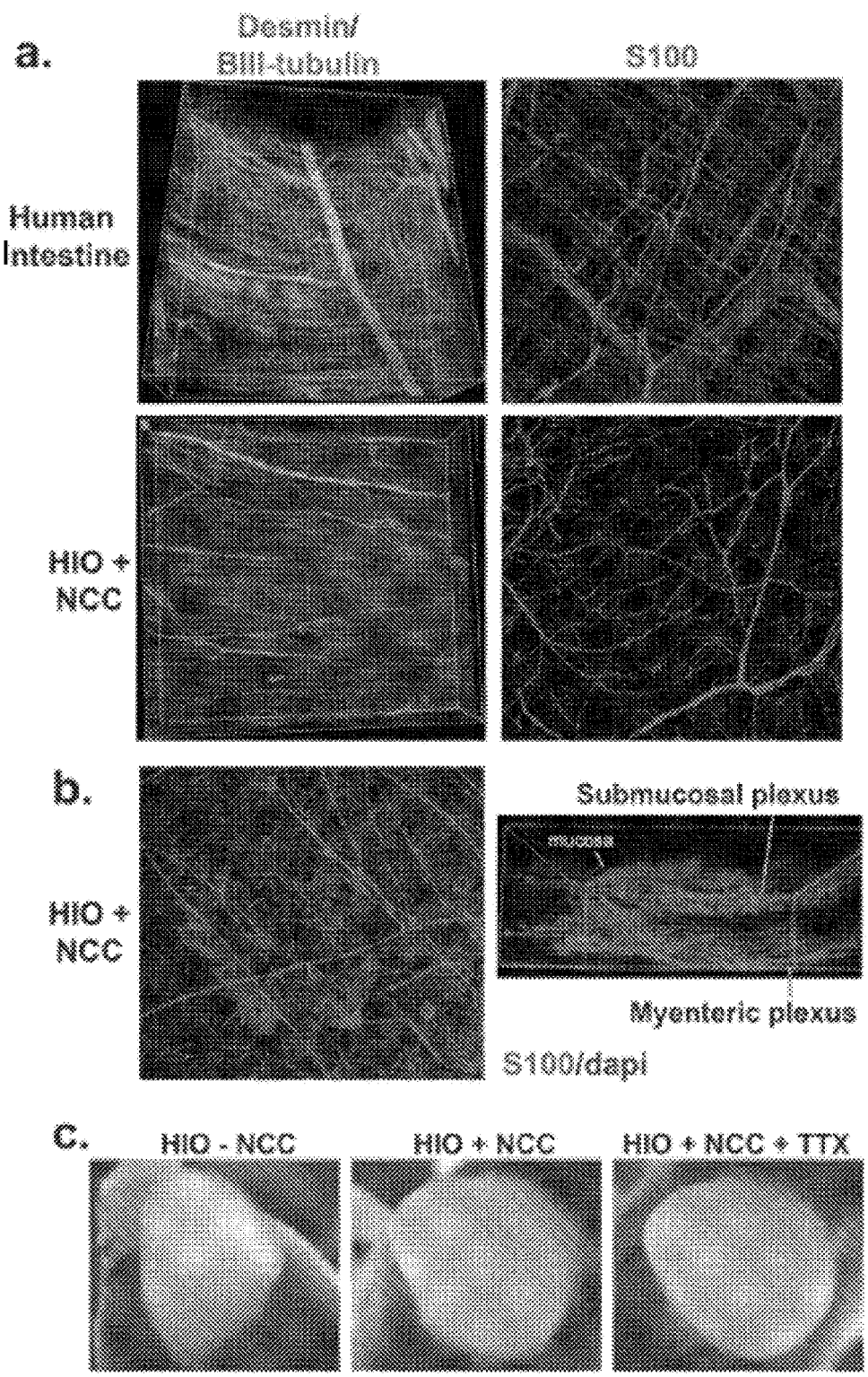

Histological analysis of ENS neurons and glia suggested that they were forming a neural plexus within the smooth muscle layers of the HIOs. However this conclusion is difficult given the 2-dimensional nature of sectioned tissues. Applicant therefore performed 3 dimensional imaging of tissue from an HIOs+NCC matured in vivo via whole mount immunofluorescence using neuronal, glial and smooth muscle markers and compared these to human small intestine (FIG. 18). The ENS of human small bowel contained a network of both neurons (BIII-tubulin) and glia (S100) that integrated into smooth muscle layers (desmin+cells). The ENS that formed within the developing HIO similarly contained a complex neural plexus of neurons and glia that appeared oriented with smooth muscle fibers (FIG. 18A). A lateral view of 3D images of HIO+NCC samples clearly showed evidence of a myenteric plexus (FIG. 18B) as well as a plexus that is located in the submucosa adjacent to the epithelium (blue–dapi). Applicant also observed clusters of neuronal cell bodies, both in sections and 3D imaging (FIG. 25), reminiscent of ganglia. Relative to human intestine, the ganglia in HIOs were smaller and less developed.

ENS-Mediated Contractile Activity.

While the organization of epithelium, smooth muscle, neurons and glia in HIO+ENS tissues were similar to that of human intestine, it was not clear if there existed any neuromuscular communication in HIO+ENS tissues. To determine if the PSC-derived ENS could function in HIO tissues Applicant explanted kidney grafts into Tyrode's solution and subjected them to an electrical field stimulation (FIG. 19C). HIO tissue without an ENS subjected to a single 1 ms pulse at 100V (high voltage) caused a single contraction, suggesting the direct stimulation of smooth muscle contraction. In contrast, HIO tissue containing an ENS subjected to a single 1 ms pulse at 50V (low voltage) triggered a sustained wave of contractions. To determine if contractions were due to the activity of the ENS Applicant blocked neuronal activity with tetrodotoxin (TTX), which binds to voltage-gated Na+channels on nerves, thus inhibiting the firing of action potentials. TTX completely inhibited the ability of low voltage stimulation to trigger motility in HIO+NCC tissue.

Neuromuscular Coupling in HIO+NCC Tissues.

GI motility involves the coordination of ENS-dependent and independent contraction and relaxation of smooth muscle. To better dissect these processes Applicant isolated tissue strips from HIOs and HIO+NCCs and analyzed them using organ chamber experiments. In the absence of neuronal stimulation, Applicant observed spontaneous phasic contractions in both HIO and HIO+NCC tissues (FIG. 19A and FIG. 26A) consistent with the presence of ICCs in both conditions (FIG. 16B). Methylene Blue, which inhibits ICC activity, abolished phasic contractions (FIG. 19B). To identify ENS-dependent roles in contraction and relaxation Applicant activated neurons using a selective α3 nicotinic receptor agonist Dimethylphenylpiperazinium (DMPP) and veratridine, which increases nerve excitability by inhibiting Na+-channels inactivation. Pharmacological activation of the ENS induced a relaxation of the muscle in HIO+NCC tissues but not in HIOs alone (FIG. 6C and FIG. 25A). Applicant confirmed that relaxation was neuron-dependent using TTX, which inhibited the ability of the neurons to induce muscle relaxation in response to DMPP and or veratridine (FIG. 19D and FIG. 27B).

Applicant aimed at identifying a putative neuromediator responsible for the smooth muscle relaxation that was induced by the ENS. As Nitric Oxide (NO) is a well-known enteric inhibitory neuromediator and as nNOS-expressing neurons are abundant in transplanted in HIO+NCC tissues (FIG. 16) Applicant inhibited NO synthesis with NG-nitro-L-arginine methyl ester (L-NAME). L-NAME pretreatment significantly decreased the relaxation after DMPP stimulation thus indicating that NO was produced by the neurons to induce a relaxation (FIG. 19E and FIG. 27C). Applicant further stimulated NO release using Sodium Nitroprusside (SNP), and observed a relaxation of smooth muscle in HIO+NCC tissues (FIG. 27D).

Methods

Cell Lines and Culture Conditions

Human ES and iPS cells, H1 (WA-01), H9 (WA-09) and WTC11 AAVS1-CAG-GCaMP6f, were maintained in an undifferentiated state on Matrigel (BD Biosciences) without feeders. H9-GAPDH-GFP hESCs were generated by targeting sequences encoding GFP to the 3' UTR of the GAPDH gene using standard procedures 33 that incorporated TALEN facilitated homologous recombination 34. GFP is expressed as T2A 35 pseudofusion protein immediately adjoining the c-terminus of GAPDH.

Cells were fed mTeSR1 media and routinely passaged using Dispase II (Gibco). NCCs and HIOs were generated and combined at an early stage of intestinal differentiation to generate HIOs containing ENS. Briefly, for NCC generation (FIG. 1), hPSCs were treated with collagenase IV (500 U/mL) in mTeSR1 for 60 min to detach colonies. Cells were washed to remove collagenase, then gently triturated and resuspended in neural induction media on non-TC treated petri dishes. Neural induction media was changed daily and retinoic acid (2 µM) was added on days 4 and 5 for posteriorization. Day 6 free-floating neurospheres were plated on fibronectin (3 µg/cm2) and fed neural induction media without RA for 4 days. Migrated cells were collected using a brief Accutase treatment (2-3 min) and passaged onto fibronectin or used immediately for combining with HIOs. NCCs were differentiated essentially as described for neuroglial 9 and mesenchymal lineages 36. Applicant generated HIOs in a similar manner to our previous protocols similar to that described above, but most notably used small molecule CHIR99021 in place of WNT3A (FIG. 22). Following the formation of gut tube spheroids, Applicant gently centrifuged spheroids +/−NCCs and embedded them in Matrigel. Cultures were fed a basic gut media (advanced DMEM/F12, 1× B27 supplement, 1× N2 supplement, 10 µM HEPES, 2 mM L-glutamine, 1× Pen-Strep) supplemented with 100 ng EGF mL-1 and maintained in vitro for up to 8 weeks.

In Vivo Transplantation and Electrical Field Stimulation of HIOs.

HIOs+/−NCCs were ectopically transplanted into the kidney capsule of NOD/SCID-gamma (NSG) mice following the protocol described above and in Watson et al. Briefly, 4-6 week HIOs were embedded in collagen and transplanted into the kidney subcapsular space. Engrafted HIOs were harvested 6-10 weeks following transplantation and analyzed for neural and glial markers or used for electrical field stimulation (EFS) experiments. For EFS, HIOs were explanted into Tyrode's solution and equilibrated for approximately 5 min before beginning stimulation. Electric stimulation was applied using a Grass S88 Stimulator (Grass Technologies) with single pulse, 1 ms duration, and 50 or 100 V settings. HIOs were then incubated for 5 min in 10 µM TTX diluted in Tyrode's, rinsed, and placed back in fresh Tyrode's. EFS was then repeated. Movies were recorded on a Leica dissection microscope using Leica Application Suite software and processed with VideoLAN and Handbrake to achieve 16× play speed.

Chick Embryo Manipulation

Chicken eggs were purchased from Charles River and incubated at 39° C. until they reached the desired Hamburger and Hamilton stage. For chicken NCC culture, dorsal neural tubes from cranial or trunk region of HH8 embryos were dissected by Gastromaster and cultured on matrigel-coated tissue culture dish with NCC culture medium (BajPai R et al, 2010) for 24 hours. The neural ectoderm was scrapped off the plate by tungsten needle after NCCs migrated out from the neural tube explants. The NCCs remained on the plate were then treated with 4 ng/mL FGF4 or 2 µM Retinoic acid for 48 hours. For NCCs injection, GFP-labeled human PSC-derived NCCs were collected and injected intersomitically into HH10-12 chicken embryos. The embryos were harvested around HH38 for analysis.

Immunohistochemistry and Microscopy

NCCs, cell monolayers, and day 0 spheroids were fixed with 4% paraformaldehyde (PFA) at 23° C. for 15 min, washed and then stained directly. Four week in vitro HIOs and in vivo transplants were fixed in 4% PFA at 4° C. for 1 hour to overnight. Tissues were processed and embedded in OCT, sectioned at approximately 10 µm, and affixed to Superfrost Plus slides (Fisherbrand). Frozen sections and cells were permeabilized with 0.25% Triton-X100 for 10 min then blocked with 5% Normal Donkey Serum (NDS, Jackson Immunoresearch) in PBS for 30 min at 23° C.

Primary antibodies diluted in PBS were applied to slides and cells overnight at 4° C. followed by washes and incubation with secondary antibodies at 23° C. for 2 hours (See Table 3 for antibodies and dilutions). Slides were mounted using Fluromount-G and images were obtained using a Zeiss ApoTome Imager Z1 or Zeiss LSM510 confocal microscope. Whole mount 3D images were obtained by fixing tissues in 4% PFA overnight at 4° C. then equilibrating in 100% methanol for 1 hour on ice. Tissues were permeabilized with Dent's bleach (4:1:1 MeOH: DMSO: 30% H2O2) for 2 hours at room temp before rehydrating with PBS. Tissues were then blocked with 5% NDS in PBS for 2 hours at room temp, incubated with primary antibodies in PBS overnight at 4° C., washed, and incubated with secondary antibodies in PBS overnight at 4° C. Following staining, tissues were dehydrated through a methanol series and cleared with Murray's Clear (2:1 Benzyl benzoate: Benzyl alcohol) prior to imaging on a Nikon A1 inverted confocal microscope. Images were processed using NIS Elements, Bitplane Imaris, Zeiss Axiovision, and Adobe Photoshop CS7 softwares.

TABLE 3

|  | Source | Dilution |
|---|---|---|
| Primary Antibody |  |  |
| Goat anti-E-Cadherin | R&D #AF648 | 1:250 |
| Rat anti-E-Cadherin | R&D #MAB7481 | 1:1000 |
| Rabbit anti-BIII-tubulin (TUJ1) | Abcam #ab18207 | 1:2000 |
| Chicken anti-BIII-tubulin (TUJ1) | Abcam #ab41489 | 1:1000 |
| Rabbit anti-c-kit/CD117 (YR145) | Abcam #ab32363 | 1:200 |
| Mouse anti-HuC/D | Invitrogen #A21271 | 1:40 |
| Rabbit anti-PGP9.5 | Dako #Z511601 | 1:1000 |
| Mouse anti-HNK-1 | DSHB #1C10 | 1:50 |
| Mouse anti-p75$^{NTR}$ | ATS #AB-N07 | 1:200 |
| Rabbit anti-Ret | Aviva #ARP30878 | 1:200 |
| Goat anti-Peripherin | Santa Cruz #sc-7604 | 1:200 |
| Mouse anti-GFAP | Millipore #MAB360 | 1:500 |
| Rabbit anti-S100 | Dako #Z031129 | 1:1000 |
| Rabbit anti-nNOS | Abcam #ab76067 | 1:1000 |
| Goat anti-Desmin | Santa Cruz #sc-7559 | 1:100 |
| Goat anti-Calretinin | Millipore #Ab1550 | 1:2000 |
| Rabbit anti-Calbindin | Gift from K. Campbell | 1:4000 |
| Chicken anti-TH | Aves #TYH | 1:500 |
| Mouse anti-human Nuclei | Chemicon #MAB1281 | 1:200 |
| Secondary Antibody |  |  |
| Donkey anti-mouse 488 | Jackson Immuno | 1:500 |
| Donkey anti-mouse 546 | Invitrogen | 1:500 |
| Donkey anti-goat 568 | Invitrogen | 1:500 |
| Donkey anti-rabbit 546 | Invitrogen | 1:500 |
| Donkey anti-rabbit 647 | Jackson Immuno | 1:500 |
| Donkey anti-chicken 549 | Invitrogen | 1:500 |

RNA Isolation and Quantitative Real-Time PCR

Total RNA from cells and organoids was isolated using NucleoSpin RNA isolation Kit (Macherey-Nagel). Complementary DNA was generated immediately following RNA isolation using SuperScript VILO cDNA Synthesis Kit (Invitrogen). Both isolation and synthesis were carried out according to the manufacturers' protocols. Applicant performed qPCR using QuantiTect SYBR Green PCR Kit (Qiagen) on a BioRad CFX96 Real-Time PCR Detection System. Primer sequences were generally obtained from qPrimerDepot (http://primerdepot.nci.nih.gov) and can be found in Table 4.

TABLE 4

| Gene | Orientation | Primer Sequence |
|---|---|---|
| AP2α | Sense | ATGCTTTGGAAATTGACGGA |
|  | Anti-sense | ATTGACCTACAGTGCCCAGC |
| Edn3 | Sense | GCACGTGCTTCACCTACAAG |
|  | Anti-sense | GGACAGTCCATAGGGCACC |
| GAPDH | Sense | CCCATCACCATCTTCCAGGAG |
|  | Anti-sense | CTTCTCCATGGTGGTGAAGACG |
| GDNF | Sense | TCCATGACATCATCGAACTGA |
|  | Anti-sense | GTCTGCCTGGTGCTGCTC |
| HoxA2 | Sense | CCAAGAAAACCGCACTTCTG |
|  | Anti-sense | CATCGGCGATTTCCAGG |
| HoxB3 | Sense | CGTCATGAATGGGATCTGC |
|  | Anti-sense | ATATTCACATCGAGCCCCAG |
| HoxB5 | Sense | GGAAGCTTCACATCAGCCAT |
|  | Anti-sense | GGAACTCCTTTTCCAGCTCC |
| HoxB7 | Sense | AACTTCCGGATCTACCCCTG |
|  | Anti-sense | CTTTCTCCAGCTCCAGGGTC |
| Pax3 | Sense | GCCGCATCCTGAGAAGTAAA |
|  | Anti-sense | CTTCATCTGATTGGGGTGCT |
| Pax7 | Sense | CAAACACAGCATCGACGG |
|  | Anti-sense | CTTCAGTGGGAGGTCAGGTT |
| Snai12 | Sense | TGACCTGTCTGCAAATGCTC |
|  | Anti-sense | CAGACCCTGGTTGCTTCAA |
| Sox10 | Sense | AGCTCAGCAAGACGCTGG |
|  | Anti-sense | CTTTCTTGTGCTGCATACGG |
| Sox9 | Sense | GTAATCCGGGTGGTCCTTCT |
|  | Anti-sense | GTACCCGCACTTGCACAAC |
| Zic1 | Sense | AAGATCCACAAAAGGACGCA |
|  | Anti-sense | CACGTGCATGTGCTTCTTG |

Ex-Vivo Intestinal Motility

Engrafted HIO+/−NCCs were harvested and placed in ice-cold HBSS. Muscle strips (4-6 mm in length and 1-2 mm in width) were cut from the engrafted HIO+/−NCC. Preparations were suspended vertically in an organ bath filled with Krebs solution (NaCl, 117 mM; KCl, 4.7 mM; MgCl2, 1.2 mM; NaH2PO4, 1.2 mM; NaHCO3, 25 mM; CaCl2, 2.5 mM and glucose, 11 mM), warmed at 37° C. and gassed with 95% O2+5% CO2. After an equilibration period of 60 min at initial tension of 0.5 g, the contractile response of the muscle was continuously recorded, using 8-chamber tissue-organ bath with isometric force transducers (Radnoti) coupled to a computer equipped with LabChart software (AD Instruments). Muscle preparations were stimulated with dimethylphenylpiperazinium (DMPP; 10 µM; Sigma) and veratridine (3 µM; Sigma). Chemical stimulations were applied at 15 min intervals followed by 3 washes. Tetrodotoxin (TTX; 10 µM; Tocris) or NG-nitro-L-arginine methyl ester (L-NAME; 50 M; Sigma) was applied 5 min before DMPP stimulation. NOS was inhibited with sodium nitroprusside (SNP; 100 µM; Sigma). Methylene Blue (50 µM) was used to inhibit ICC activity. The effects of chemical stimulation on tension were evaluated by measuring the area under the curve (AUC). Data are expressed in ΔΔUC i.e. "Stimulated" AUC measured 120s after stimulation minus "Control" AUC measured 120 s before stimulation.

Discussion

Applicant used principles of embryonic intestinal development to engineer human PSC-derived intestinal tissue containing a functional ENS. Human PSC-derived vagal-like NCCs that were recombined with PSC-derived intestinal organoids in 3 dimensional growth conditions migrated into intestinal mesenchyme, self-organized, and differentiated into an array of neuronal and glial cell types of the ENS. Following engraftment and growth in vivo, NCCs formed complex ganglionic structures and interganglionic fibers, similar to embryonic development of the myenteric and submucosal neural plexus. Applicant further demonstrated that the NCC-derived ENS was functionally integrated into intestinal smooth muscle and drove NO-dependent relaxation. The high degree of tissue organization seen in transplanted HIOs+NCCs suggests that the tissue that Applicant engineered in vitro had the intrinsic information for coordinated cell migration, proliferation, lineage commitment and assembly into a plexus that occurs during embryonic development of the ENS.

Vagal NCCs that give rise to the ENS derive from more posterior, HOX-positive regions of the neural tube. HOXB5, for example, is expressed in human NCCs during colonization of the gut and is required for formation of the ENS in mice. Studies in vertebrate embryos have demonstrated the importance of Wnt, FGF and retinoic acid (RA) signaling in neural patterning and formation of HOX-expressing NCCs. Applicant observed RA-induced expression of vagal HOX genes A2, B3, B5, and B7, whereas treatment with FGF4 had little effect (data not shown). Recent findings have observed that activation of Wnt signaling also promotes formation of NCCs capable of forming melanocytes, which is a hallmark of vagal/trunk NCCs 11, and Applicant also observed that activation of Wnt signaling can promote posterior NCC HOX gene expression, albeit to a lower extent than RA (data not shown). At the functional level, both PSC-derived cranial and vagal NCCs were capable of incorporating into HIOs and forming neuroglial lineages, which is consistent with studies done in chick-quail chimeric embryos where cranial NCCs could efficiently contribute to the ENS. Applicant observed differences in that cranial-like NCCs+HIOs also gave rise to pigmented cells and cartilage, consistent with the broader differentiation potential of cranial NCCs.

Applicant routinely observed the formation of a neuroglial plexus in transplanted HIOs+NCCs in close association with smooth muscle fibers with organization similar to the myenteric plexus. However, several lines of evidence suggest that the NCC-derived ENS was less mature and more fetal in nature. For example, development of a submucosal plexus appeared delayed in HIO+NCC tissues, and this may be similar to development in the human fetal gut, where the submucosal plexus develops 2-3 weeks after the myenteric plexus 26. Another indicator of developmental immaturity is that the neuroglial plexus in HIOs contained smaller nerve bundles than the adult human intestine, more similar to what is observed in the human fetal gut 16. The immature/fetal nature of HIO+NCC tissues may provide an opportunity to identify specific factors that regulate maturation of the fetal gut/ENS. For example it was recently demonstrated that the microbiota of the lumen influence the colonization of the mucosa by glial cells and the HIO+/−ENS model could allow for mechanistic dissection of this process. Factors that promote intestinal maturation could be used clinically with premature infants, who are at heightened risk for intestinal infections due to an immature mucosa.

Applicant observed a substantial degree of neuronal diversity in HIO+NCC tissue in vitro, including excitatory and interneurons that had intrinsic and inducible waves of calcium efflux, suggestive of neuronal activity. HIO+NCC tissues that were grown in vivo acquired additional neuronal diversity with nNOS+inhibitory neurons, which are known to form at later stages in the developing fetal mouse gut. Moreover, neuroglial cells assembled into a myenteric and submucosal plexus that were functionally associated with highly differentiated layers of smooth muscle. Electrical field stimulation (EFS) of these engineered tissues triggered ENS-dependent waves of motility that were qualitatively similar to peristalsis. However, Applicant also observed intrinsic contractile activity that was dependent on resident ICCs that were present in both HIOs and HIO+NCC. Together our data suggest that ICCs were largely driving contraction whereas relaxation of muscle was ENS-dependent and mediated via nNOS+inhibitory neurons present in HIO+NCC tissue. The fact that NOS inhibitory neurons became functional earlier than cholinergic excitatory neurons supports the conclusion the ENS in HIOs is fetal in nature.

There are several pronounced differences between rodents and humans regarding development, physiology and diseases of the intestine. For example, development of crypts occurs in utero in humans whereas it happens postnatally in mice. During ENS development there are differences in the formation of TH neurons between mouse and humans. Given that HIOs+NCCs contain TH positive neurons in vitro and in vivo, this system may be the only means to study the unique developmental properties of these cell types. Moreover, an experimental system to study human TH+dopaminergic ENS neurons may provide insight into GI dysmotility symptoms found in Parkinson's patients 32 that is caused by degeneration of this neuronal subtype. Because of its highly tractable nature, this system should be particularly useful in studying developmental deficits of the ENS, for example Hirschprung's disease. Defects in NCC formation, migration, incorporation into the mesenchyme, and proliferation can all result in aganglionic sections of the intestine. Our ability to study the interactions between NCCs and intestinal organoid in vitro and to monitor and manipulate these interactions during formation of a functional ENS should allow for unprecedented mechanistic dissection of known and novel forms of Hirschprung's disease in humans.

REFERENCES

Cheng, X. et al. Self-renewing endodermal progenitor lines generated from human pluripotent stem cells. Cell Stem Cell 10, 371-384 (2012).

Wells, J. M. & Spence, J. R. How to make an intestine. Development 141, 752-760 (2014).

Lahar, N. et al. Intestinal subepithelial myofibroblasts support in vitro and in vivo growth of human small intestinal epithelium. PLoS ONE 6, e26898 (2011).

Levin, D. E. et al. Human tissue-engineered small intestine forms from postnatal progenitor cells. J. Pediatr. Surg. 48, 129-137 (2013).

Spence, J. R. et al. Directed differentiation of human pluripotent stem cells into intestinal tissue in vitro. Nature 470, 105-109 (2011).

McCracken, K. W., Howell, J. C., Wells, J. M. & Spence, J. R. Generating human intestinal tissue from pluripotent stem cells in vitro. Nat. Protoc. 6, 1920-1928 (2011).

Williamson, R. C., Buchholtz, T. W. & Malt, R. A. Humoral stimulation of cell proliferation in small bowel after transection and resection in rats. Gastroenterology 75, 249-254 (1978).

Juno, R. J. et al. A serum factor after intestinal resection stimulates epidermal growth factor receptor signaling and proliferation in intestinal epithelial cells. Surgery 132, 377-383 (2002).

Juno, R. J., Knott, A. W., Erwin, C. R. & Warner, B. W. A serum factor(s) after small bowel resection induces intestinal epithelial cell proliferation: effects of timing, site, and extent of resection. J. Pediatr. Surg. 38, 868-874 (2003).

Simon-Assmann, P., Turck, N., Sidhoum-Jenny, M., Gradwohl, G. & Kedinger, M. In vitro models of intestinal epithelial cell differentiation. Cell Biol. Toxicol. 23, 241-256 (2007).

Jung, P. et al. Isolation and in vitro expansion of human colonic stem cells. Nat. Med. 17, 1225-1227 (2011).

Sato, T. et al. Long-term expansion of epithelial organoids from human colon, adenoma, adenocarcinoma, and Barrett's epithelium. Gastroenterology 141, 1762-1772 (2011).

Campbell, F. C., Tait, I. S., Flint, N. & Evans, G. S. Transplantation of cultured small bowel enterocytes. Gut 34, 1153-1155 (1993).

Agopian, V. G., Chen, D. C., Avansino, J. R. & Stelzner, M. Intestinal stem cell organoid transplantation generates neomucosa in dogs. J. Gastrointest. Surg. 13, 971-982 (2009).

Avansino, J. R., Chen, D. C., Hoagland, V. D., Woolman, J. D. & Stelzner, M. Orthotopic transplantation of intestinal mucosal organoids in rodents. Surgery 140, 423-434 (2006).

Tait, I. S., Evans, G. S., Flint, N. & Campbell, F. C. Colonic mucosal replacement by syngeneic small intestinal stem cell transplantation. Am. J. Surg. 167, 67-72 (1994).

Tait, I. S., Flint, N., Campbell, F. C. & Evans, G. S. Generation of neomucosa in vivo by transplantation of dissociated rat postnatal small intestinal epithelium. Differentiation 56, 91-100 (1994).

Fordham, R. P. et al. Transplantation of expanded fetal intestinal progenitors contributes to colon regeneration after injury. Cell Stem Cell 13, 734-744 (2013).

Yui, S. et al. Functional engraftment of colon epithelium expanded in vitro from a single adult Lgr5(+) stem cell. Nat. Med. 18, 618-623 (2012).

Kosinski, C. et al. Indian hedgehog regulates intestinal stem cell fate through epithelial-mesenchymal interactions during development. Gastroenterology 139, 893-903 (2010).

McLin, V. A., Henning, S. J. & Jamrich, M. The role of the visceral mesoderm in the development of the gastrointestinal tract. Gastroenterology 136, 2074-2091 (2009).

Zorn, A. M. & Wells, J. M. Vertebrate endoderm development and organ formation. Annu. Rev. Cell Dev. Biol. 25, 221-251 (2009).

Gracz, A. D. et al. Brief report: CD24 and CD44 mark human intestinal epithelial cell populations with characteristics of active and facultative stem cells. Stem Cells 31, 2024-2030 (2013).

Kroon, E. et al. Pancreatic endoderm derived from human embryonic stem cells generates glucose-responsive insulin-secreting cells in vivo. Nat. Biotechnol. 26, 443-452 (2008).

Kovalenko, P. L. & Basson, M. D. The correlation between the expression of differentiation markers in rat small intestinal mucosa and the transcript levels of schlafen 3. JAMA Surg. 148, 1013-1019 (2013).

Dekaney, C. M. et al. Expansion of intestinal stem cells associated with long-term adaptation following ileocecal resection in mice. Am. J. Physiol. Gastrointest. Liver Physiol. 293, G1013-G1022 (2007).

D'Amour, K. A. et al. Efficient differentiation of human embryonic stem cells to definitive endoderm. Nat. Biotechnol. 23, 1534-1541 (2005).

Warlich, E. et al. Lentiviral vector design and imaging approaches to visualize the early stages of cellular reprogramming Mol. Ther. 19, 782-789 (2011).

Wang, F. et al. Isolation and characterization of intestinal stem cells based on surface marker combinations and colony-formation assay. Gastroenterology 145, 383-395.e1-e21 (2013).

Groneberg, D. A. et al. Intestinal peptide transport: ex vivo uptake studies and localization of peptide carrier PEPT1. Am. J. Physiol. Gastrointest. Liver Physiol. 281, G697-G704 (2001).

Furness, J. B. The enteric nervous system and neurogastroenterology. Nature reviews. Gastroenterology & hepatology 9, 286-294 (2012).

Sasselli, V., Pachnis, V. & Burns, A. J. The enteric nervous system. Developmental biology 366, 64-73 (2012).

Obermayr, F., Hotta, R., Enomoto, H. & Young, H. M. Development and developmental disorders of the enteric nervous system. Nature reviews. Gastroenterology & hepatology 10, 43-57 (2013).

Saffrey, M. J. Cellular changes in the enteric nervous system during ageing. Developmental biology 382, 344-355 (2013).

McKeown, S. J., Stamp, L., Hao, M. M. & Young, H. M. Hirschsprung disease: a developmental disorder of the enteric nervous system. Wiley interdisciplinary reviews. Developmental biology 2, 113-129 (2013).

Burns, A. J. & Thapar, N. Neural stem cell therapies for enteric nervous system disorders. Nature reviews. Gastroenterology & hepatology 11, 317-328 (2014).

Hao, M. M. & Young, H. M. Development of enteric neuron diversity. Journal of cellular and molecular medicine 13, 1193-1210 (2009).

Lancaster, M. A. & Knoblich, J. A. Organogenesis in a dish: modeling development and disease using organoid technologies. Science 345, 1247125 (2014).

Bajpai, R., et al. CHD7 cooperates with PBAF to control multipotent neural crest formation. Nature 463, 958-962 (2010).

Curchoe, C. L., et al. Early acquisition of neural crest competence during hESCs neuralization. PloS one 5, e13890 (2010).

Mica, Y., Lee, G., Chambers, S. M., Tomishima, M. J. & Studer, L. Modeling neural crest induction, melanocyte specification, and disease-related pigmentation defects in hESCs and patient-specific iPSCs. Cell reports 3, 1140-1152 (2013).

Kudoh, T., Wilson, S. W. & Dawid, I. B. Distinct roles for Fgf, Wnt and retinoic acid in posteriorizing the neural ectoderm. Development 129, 4335-4346 (2002).

Watson, C. L., et al. An in vivo model of human small intestine using pluripotent stem cells. Nature medicine 20, 1310-1314 (2014).

Fu, M., Tam, P. K., Sham, M. H. & Lui, V. C. Embryonic development of the ganglion plexuses and the concentric layer structure of human gut: a topographical study. Anatomy and embryology 208, 33-41 (2004).

Young, H. M., Ciampoli, D., Hsuan, J. & Canty, A. J. Expression of Ret-, p75(NTR)-, Phox2a-, Phox2b-, and tyrosine hydroxylase-immunoreactivity by undifferentiated neural crest-derived cells and different classes of enteric neurons in the embryonic mouse gut. Dev Dyn 216, 137-152 (1999).

Young, H. M., et al. GDNF is a chemoattractant for enteric neural cells. Developmental biology 229, 503-516 (2001).

Chen, T. W., et al. Ultrasensitive fluorescent proteins for imaging neuronal activity. Nature 499, 295-300 (2013).

Huebsch, N., et al. Automated Video-Based Analysis of Contractility and Calcium Flux in Human-Induced Pluripotent Stem Cell-Derived Cardiomyocytes Cultured over Different Spatial Scales. Tissue engineering. Part C, Methods 21, 467-479 (2015).

Fu, M., Lui, V. C., Sham, M. H., Cheung, A. N. & Tam, P. K. HOXB5 expression is spatially and temporarily regulated in human embryonic gut during neural crest cell colonization and differentiation of enteric neuroblasts. Dev Dyn 228, 1-10 (2003).

Lui, V. C., et al. Perturbation of hoxb5 signaling in vagal neural crests down-regulates ret leading to intestinal hypoganglionosis in mice. Gastroenterology 134, 1104-1115 (2008).

Denham, M., et al. Multipotent caudal neural progenitors derived from human pluripotent stem cells that give rise to lineages of the central and peripheral nervous system. Stem cells 33, 1759-1770 (2015).

Le Douarin, N. M., Creuzet, S., Couly, G. & Dupin, E. Neural crest cell plasticity and its limits. Development 131, 4637-4650 (2004).

Zhang, D., Brinas, I. M., Binder, B. J., Landman, K. A. & Newgreen, D. F. Neural crest regionalisation for enteric nervous system formation: implications for Hirschsprung's disease and stem cell therapy. Developmental biology 339, 280-294 (2010).

Wallace, A. S. & Burns, A. J. Development of the enteric nervous system, smooth muscle and interstitial cells of Cajal in the human gastrointestinal tract. Cell and tissue research 319, 367-382 (2005).

Kabouridis, P. S., et al. Microbiota controls the homeostasis of glial cells in the gut lamina propria. Neuron 85, 289-295 (2015).

Bergner, A. J., et al. Birthdating of myenteric neuron subtypes in the small intestine of the mouse. The Journal of comparative neurology 522, 514-527 (2014).

Baetge, G. & Gershon, M. D. Transient catecholaminergic (TC) cells in the vagus nerves and bowel of fetal mice: relationship to the development of enteric neurons. Developmental biology 132, 189-211 (1989).

Blaugrund, E., et al. Distinct subpopulations of enteric neuronal progenitors defined by time of development, sympathoadrenal lineage markers and Mash-1-dependence. Development 122, 309-320 (1996).

Anlauf, M., Schafer, M. K., Eiden, L. & Weihe, E. Chemical coding of the human gastrointestinal nervous system: cholinergic, VlPergic, and catecholaminergic phenotypes. The Journal of comparative neurology 459, 90-111 (2003).

Anderson, G., et al. Loss of enteric dopaminergic neurons and associated changes in colon motility in an MPTP mouse model of Parkinson's disease. Experimental neurology 207, 4-12 (2007).

Costa, M., et al. A method for genetic modification of human embryonic stem cells using electroporation. Nature protocols 2, 792-796 (2007).

Hockemeyer, D., et al. Genetic engineering of human pluripotent cells using TALE nucleases. Nature biotechnology 29, 731-734 (2011).

Tang, W., et al. Faithful expression of multiple proteins via 2A-peptide self-processing: a versatile and reliable method for manipulating brain circuits. The Journal of neuroscience: the official journal of the Society for Neuroscience 29, 8621-8629 (2009).

Lee, G., et al. Isolation and directed differentiation of neural crest stem cells derived from human embryonic stem cells. Nature biotechnology 25, 1468-1475 (2007).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an intestinal organoid having enteric neuronal and glial cell types, comprising the steps of:
   a) providing a mid/hindgut spheroid;
   b) providing vagal neural crest cells;
   c) combining and mechanically aggregating the mid/hindgut spheroid together with the vagal neural crest cells to form a mid/hindgut spheroid-neural crest cell aggregate; and
   d) maintaining said mid/hindgut spheroid-neural crest cell aggregate in a growth media to form an intestinal organoid, wherein said intestinal organoid comprises neuronal cell types and glial cell types;
   wherein the neuronal cell types express tyrosine hydroxylase (TH), calbindin, calretinin, and serotonin (5-HT),
   wherein the mid/hindgut spheroid is derived from definitive endoderm;
   wherein the vagal neural crest cells express Hoxb3, Hoxb5, or Hoxb7 and are derived from a neurosphere, wherein said neurosphere is derived from a human precursor cell selected from one or both of an embryonic stem cell (ESC) or an induced Pluripotent Stem Cell (IPSC); and
   wherein the enteric neuronal cell types exhibit neuronal activity as measured by rhythmic waves of calcium transients.

2. The method of claim 1 wherein said neuronal cell types comprise βIII-tubulin.

3. The method of claim 1, further comprising the step of transplanting said intestinal organoid in vivo into an intestinal vasculature of a mammal for a period of time sufficient to mature into an intestinal organoid comprising nNOS+ inhibitory neurons.

4. The method of claim 3 wherein said intestinal organoid comprises a functional enteric nervous system (ENS) and is capable of contractile activity.

5. The method of claim 1, further comprising the step of transplanting said intestinal organoid in vivo into an intestinal vasculature of a mammal for a period of time sufficient to mature into an intestinal organoid comprising neurons, wherein said neurons are embedded within desmin+ smooth muscle layers.

6. The method of claim 1, further comprising the step of transplanting said intestinal organoid in vivo into an intestinal vasculature of a mammal for a period of time sufficient to mature into an intestinal organoid comprising glial cells embedded within a mesenchymal layer of said intestinal organoids.

7. The method of claim 1, further comprising the step of transplanting said intestinal organoid in vivo into an intestinal vasculature of a mammal for a period of time sufficient to mature into an intestinal organoid comprising dopaminergic neurons, interneurons, sensory neurons, excitatory neurons, and inhibitory neurons.

8. The method of claim 1, wherein the mid/hindgut spheroid and vagal neural crest cells are mechanically aggregated by low speed centrifugation.

9. The method of claim 1, wherein the enteric neuronal cell types are positive for the pan-neuronal marker PGP9.5 and βIII-tubulin, and comprise: dopaminergic neurons expressing TH, interneurons expressing 5-HT and ChAT, sensory neurons expressing calbindin, and/or excitatory neurons expressing calretinin; wherein the glial cell types are positive for the glial marker S100; and wherein the enteric neuronal and glial cell types are embedded in the mesenchyme of the intestinal organoid.

\* \* \* \* \*